(12) United States Patent
Neev

(10) Patent No.: US 10,588,694 B1
(45) Date of Patent: Mar. 17, 2020

(54) DEVICES AND METHODS FOR GENERATION OF SUBSURFACE MICRO-DISRUPTIONS FOR BIOMEDICAL APPLICATIONS

(71) Applicant: Joseph Neev, Laguna Beach, CA (US)

(72) Inventor: Joseph Neev, Laguna Beach, CA (US)

(*) Notice: Subject to any disclaimer, the term of this patent is extended or adjusted under 35 U.S.C. 154(b) by 761 days.

(21) Appl. No.: 14/016,892

(22) Filed: Sep. 3, 2013

Related U.S. Application Data

(63) Continuation-in-part of application No. 12/448,987, filed as application No. PCT/US2008/051337 on Jan. 17, 2008, now Pat. No. 8,523,926, application No. 14/016,892, which is a continuation-in-part of application No. 13/248,001, filed on Sep. 28, 2011, now abandoned.

(60) Provisional application No. 60/885,852, filed on Jan. 19, 2007, provisional application No. 60/888,258, filed on Feb. 5, 2007, provisional application No. 60/901,950, filed on Feb. 17, 2007, provisional application No. 60/904,247, filed on Feb. 28, 2007, provisional application No. 60/904,415, filed on Mar. 2, 2007, provisional application No. 60/946,944, filed on Jun. 28, 2007, provisional application No. 60/978,189, filed on Oct. 8, 2007, provisional application No. 61/387,010, filed on Sep. 28, 2010.

(51) Int. Cl.
  *A61B 18/20* (2006.01)

(52) U.S. Cl.
  CPC ................. *A61B 18/203* (2013.01)

(58) Field of Classification Search
  CPC ....... A61F 9/008; A61B 18/203; A61B 18/20; A61B 18/18

USPC ............................................ 606/4–6; 607/89
See application file for complete search history.

(56) References Cited

U.S. PATENT DOCUMENTS

| | | |
|---|---|---|
| 4,907,586 A | 3/1990 | Bille |
| 5,383,118 A | 1/1995 | Nguyen |
| 5,549,632 A | 8/1996 | Lai |
| 5,656,186 A | 8/1997 | Mourou |
| 5,720,894 A | 2/1998 | Neev |
| 5,879,346 A | 3/1999 | Waldman |
| 5,993,438 A | 11/1999 | Juhasz |
| 6,149,644 A | 11/2000 | Xie |

(Continued)

FOREIGN PATENT DOCUMENTS

| | | |
|---|---|---|
| WO | WO 87/07265 | 12/1987 |
| WO | WO 97/06856 | 2/1997 |

(Continued)

OTHER PUBLICATIONS

PCT Search Report for PCT/US2008/051337.

(Continued)

*Primary Examiner* — Scott M. Getzow
(74) *Attorney, Agent, or Firm* — Richard B. Cates

(57) ABSTRACT

A device comprises an energy source capable of generating short bursts of energy at a variable pulse repetition rates. The repetition rates range from a single shot to several hundred Mega-Hertzs so that selective, three dimensional interactions with a volumetric zone of skin or issue can be created substantially without damage or substantial changes to overlying or underlying or surrounding tissue or skin. A method and a device for treating targeted material and targeted tissue are described.

27 Claims, 23 Drawing Sheets

(56) References Cited

U.S. PATENT DOCUMENTS

| | | |
|---|---|---|
| 6,325,792 B1 | 12/2001 | Swinger |
| 6,482,199 B1 | 11/2002 | Neev |
| 2002/0169394 A1 | 11/2002 | Eppstein |
| 2003/0052102 A1 | 3/2003 | Amako |
| 2003/0135201 A1 | 7/2003 | Gonnelli |
| 2005/0010198 A1 | 1/2005 | Marchitto |
| 2005/0143719 A1 | 6/2005 | Sink |
| 2005/0189329 A1 | 9/2005 | Talwar |
| 2006/0007965 A1 | 1/2006 | Tankovich |
| 2006/0047243 A1 | 3/2006 | Rosenberg |
| 2006/0195076 A1* | 8/2006 | Blumenkranz ..... A61F 9/00736 606/4 |
| 2006/0217636 A1 | 9/2006 | Braig |
| 2006/0217690 A1 | 9/2006 | Bastin |
| 2006/0241585 A1 | 10/2006 | Silberberg |
| 2008/0015553 A1* | 1/2008 | Zacharias ............... A61F 9/008 606/4 |

FOREIGN PATENT DOCUMENTS

| | | |
|---|---|---|
| WO | WO 02/05889 | 1/2002 |
| WO | 02/053050 | 7/2002 |
| WO | WO 2004/000389 | 12/2003 |
| WO | WO 2006/111201 | 10/2006 |

OTHER PUBLICATIONS

PCT Written Opinion for PCT/US2008/051337.

Mark H Niemz et al. "Plasma-Mediated Ablation of Corneal Tissue at 1053 nm Using an Nd: YLF Oscillator/Regenerative Amplifier Laser," Lasers in Surgery and Medicine, 1991. p. 426. vol. II. Wiley-Liss, Inc., USA.

Steven L. Jacques. "Laser Tissue Interactions-Photochemical, Photothermal, Photomechanical," Lasers in General Surgery, Jun. 1992, p. 531, vol. 72. No. 3, General Biology Research Laboratory, Houston. TX.

Du et al. "Laser-Induced Breakdown by Impact Ionization in SiO2 with Pulse Widths from 7ns to 150 fs," Appl. Phys. Lett, 64 (23), Jun. 6, 1994.

Tibor Juhasz et al., "Time Resolved Observations of Shock Waves and Cavitation Bubbles Generated by Femtosecond Laser Pulses in Cornea Tissue and Water," Lasers in Surgery and Medicine, 1996, p. 23, vol. 19, Wiley-Liss, Inc., USA.

\* cited by examiner

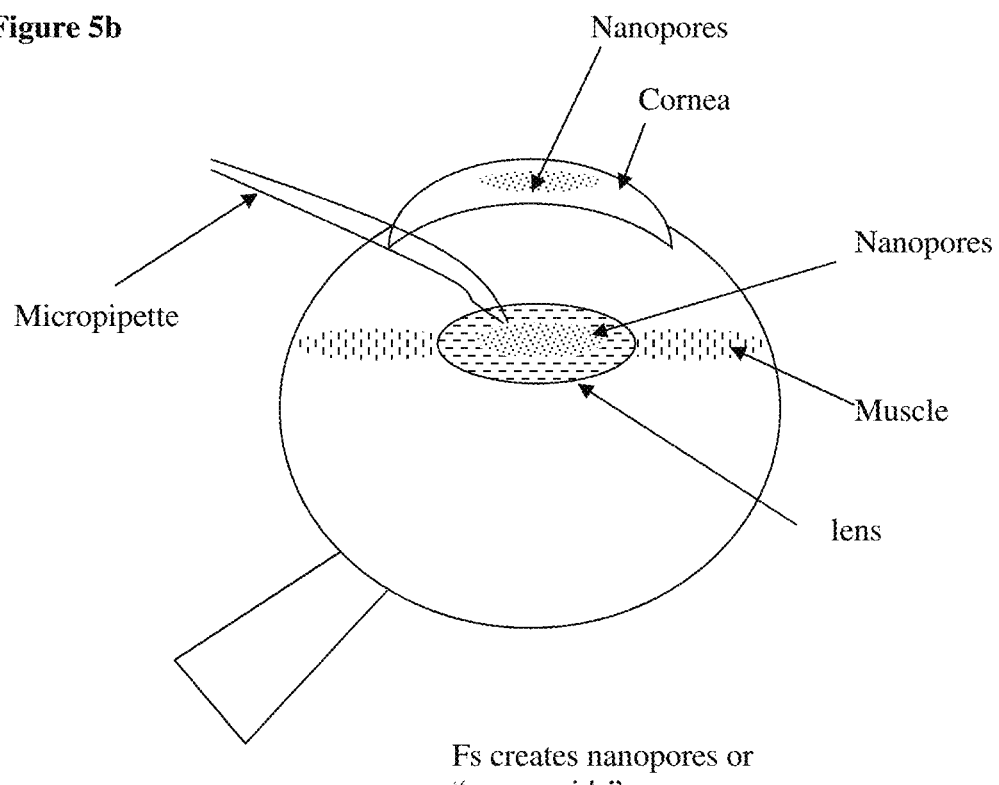

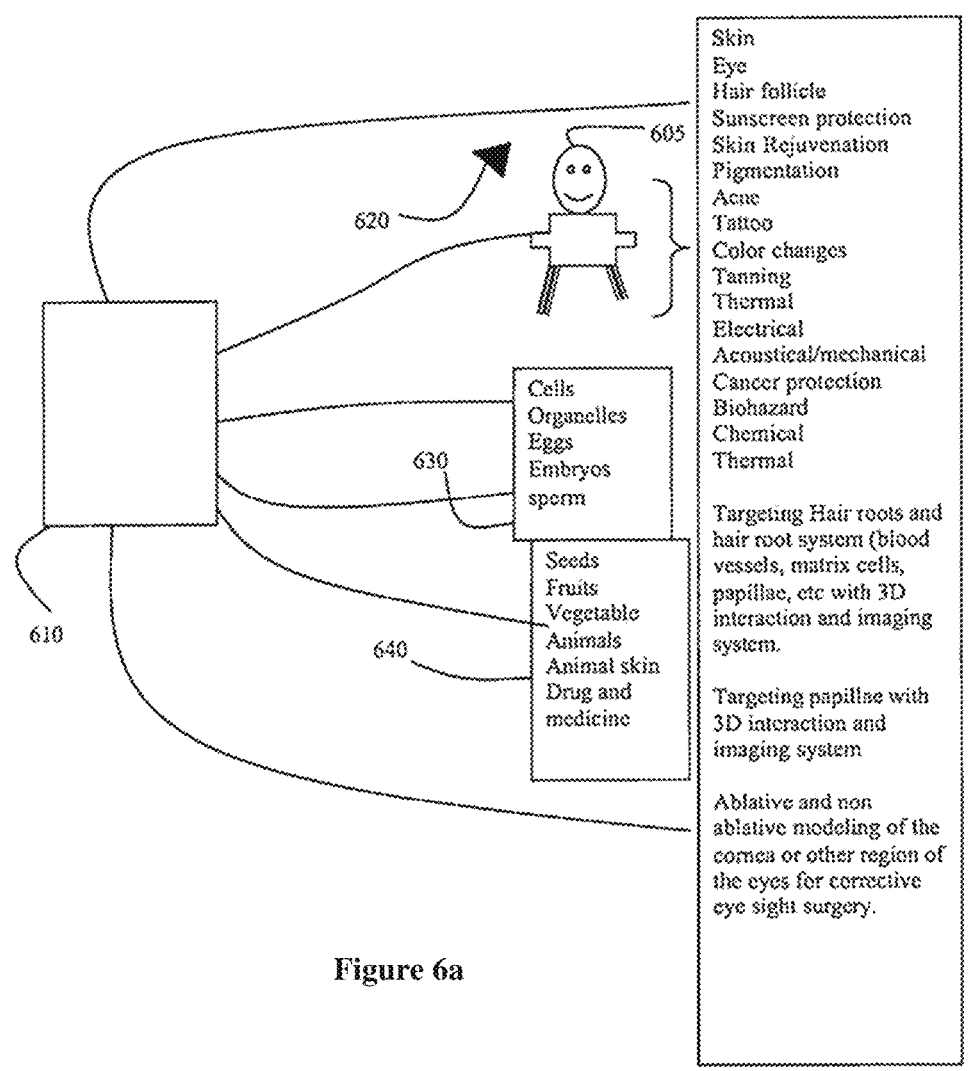
Figure 6a
Figure 6b
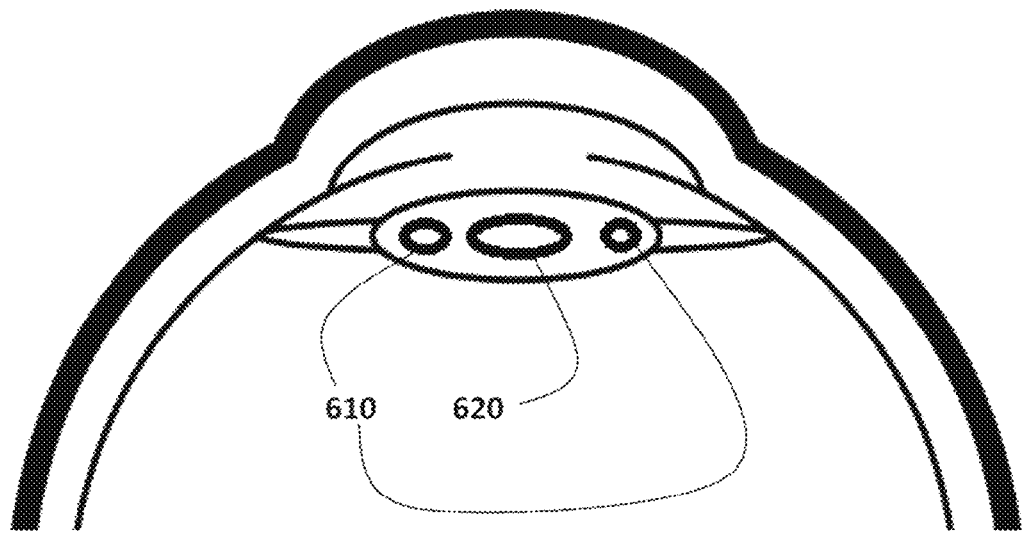

A - Excitation source
720 power source (e.g. AAA batteries)
725 capacitors
730 trigger
735 charge button
755 control board microprocessor
750 lamp/flash lamp
765 window
765 a window
B - breath or bacteria input
C - Breach or blow outlet
D - Sample Chamber
E - Lenses
G - Filters/ band path filters
H - Microprocessors Two Method
1) $E_O \geq E_{O\,Thresh}$
2) $E_O \leq E_{O\,Thresh}$
But $n_{target} > n_{neighboring\,region}$

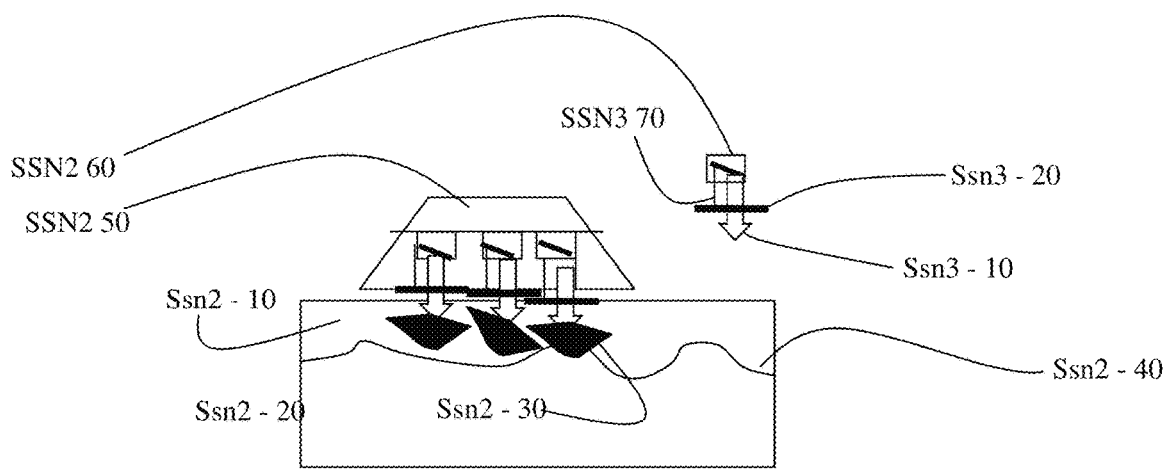
Figure 11C (= SSN2)
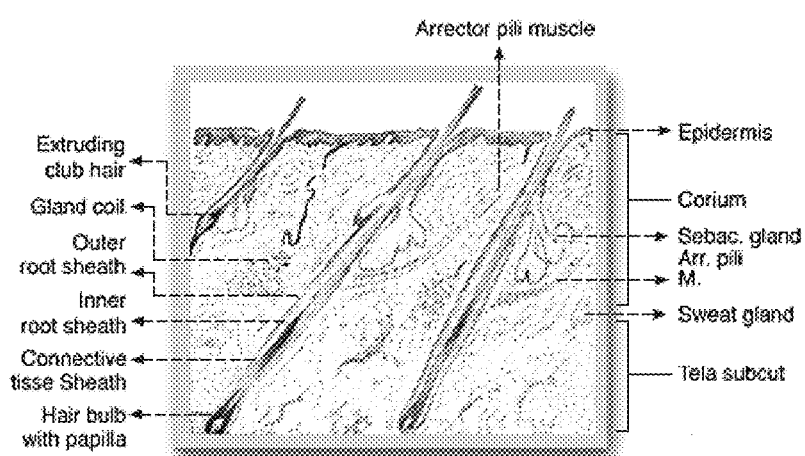
Figure 17 – additional targeted regions (Shown by circles)

(Ultrasound images of follicles)

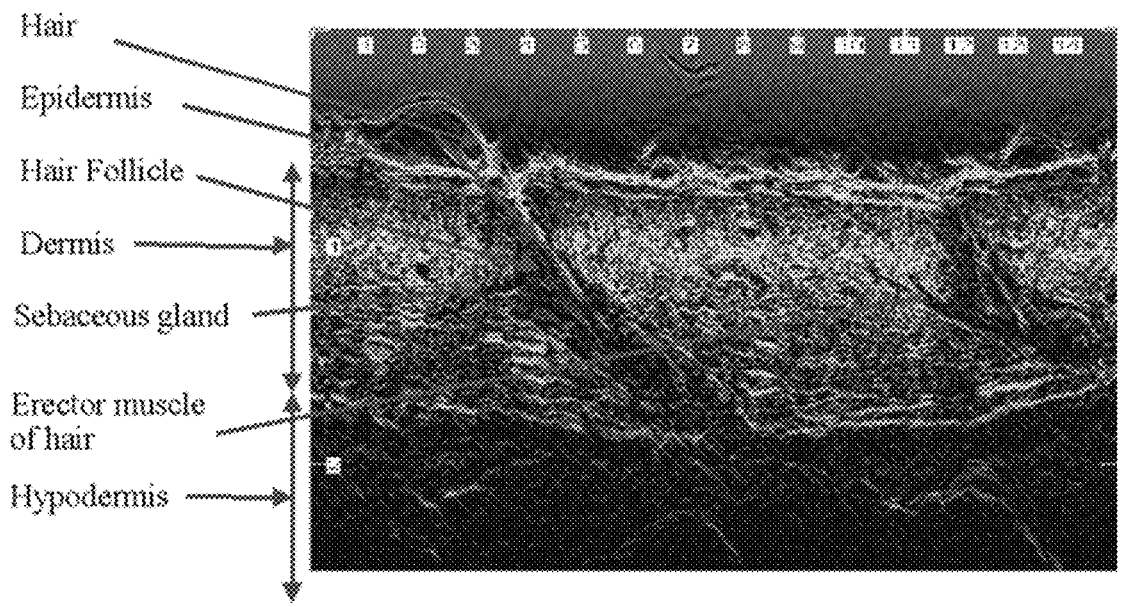
Figure 15 (OCT images of follicles)
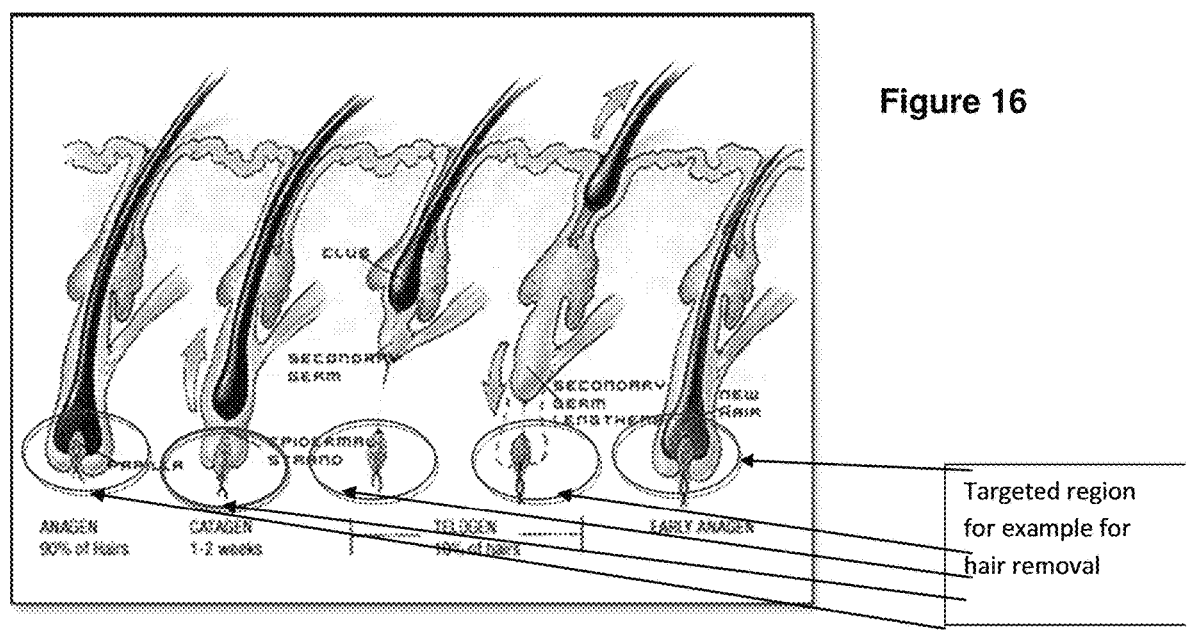
Figure 16

DEVICES AND METHODS FOR GENERATION OF SUBSURFACE MICRO-DISRUPTIONS FOR BIOMEDICAL APPLICATIONS

CROSS-REFERENCE TO RELATED APPLICATIONS

This application is a continuation-in-part of U.S. patent application Ser. No. 12/448,987, filed Jul. 17, 2009, which is a U.S. national stage of PCT/US2008/051337, filed Jan. 17, 2008, which claims priority to U.S. Provisional Application No. 60/885,852, filed Jan. 19, 2007, and U.S. Provisional Application No. 60/888,258, filed Feb. 5, 2007, and U.S. Provisional Application No. 60/901,950, filed Feb. 17, 2007, and U.S. Provisional Application No. 60/904,247, filed Feb. 28, 2007, and U.S. Provisional Application No. 60/904,415, filed May 27, 2007, and U.S. Provisional Application No. 60/946,944, filed Jun. 28, 2007, and U.S. Provisional Application No. 60/978,189, filed Oct. 8, 2007, and this application is a continuation-in-part of U.S. patent application Ser. No. 13/248,001, filed Sep. 28, 2011, which claims priority to U.S. Provisional Patent Application Ser. No. 61/387,010, filed Sep. 28, 2010, all which are hereby incorporated by reference in their entireties.

FIELD OF THE INVENTION

The present invention relates to the field of tissue modifications, imaging, and surgery. More particularly, the invention relates to a device and method for changing the chemical, optical, thermal, mechanical, or other physical properties of a material and interacting underneath a surface of a material.

BACKGROUND OF THE INVENTION

There is a severe and immediate problem in the general public today of acquiring skin cancer such as melanoma and basal cell carcinoma. Nearly 30% of those acquiring melanoma die from the disease. The principal effective prevention of this deadly disease is protective clothing or sunscreen. Nearly everyone is at risk especially people of European decent. While sunscreen provides various degrees of protection, it is difficult to control its application because the application is done by individuals under different conditions. Sunscreens are temporary by nature, and need to be applied in intervals ranging from minutes to hours. Obviously, a device and a method that will provide a more complete, more permanent, and a more uniform method of protection are highly desirable.

Sun light and environmental factors can also be a significant factor in the aging of the skin. Here again, uniform, reliable and permanent protection are very difficult to achieve.

Skin color and tanning are problems for the cosmetics and beauty industry. Methods that would provide safe tanning or other modification of skin color would be of high economic and social importance. Unfortunately, permanent or semi-permanent skin color changes are very difficult to achieve, and in the prior art can be accomplished only at high expense, and with very limited efficacy. Conventional tanning methods are less expensive, are temporary, but carry significant health hazards.

Enhanced insulation of the skin from thermal energy fluctuations is also highly desirable. To date, principally clothing and gloves are used for such protection. In some cases, swimmers may use oils and ointment to enhance insulation. These methods and devices are obviously temporary in nature and provide only external insulation that can be removed by environmental influences and does not change the intrinsic properties of the skin. Certainly, swimmers, sailors, people in cold regions of the country, people who often work outside in extreme temperature and weather conditions, people who need to operate equipment in cold or hot conditions but need to preserve the agility and flexibility of their hands or feet operation (for example, soldiers who need to operate weapons under extreme cold or hot temperatures and are severely restricted by the cover of gloves), could all benefit from such thermal insulation.

Enhanced insulation from electrical influences is also desirable in many circumstances. The only methods or devices presently available that protect a target, and in particular the human body and human or animal or plant skin from external electrical influences are electrical insulating material applied to the surface of the skin or by simply keeping the skin dry from conducting liquid.

Excessive skin sensitivity is yet another condition that affects many people in the United States as well as the rest of the world. People with high skin sensitivity may need to take pain medication that may have harmful side effects and unintended as well as undesired effects on other organs. Again, external insulation that insulated the skin from mechanical, thermal chemical or electrical stimulation can be used to create a vacuum or insulating layers around the skin. But devices and methods that would directly and effectively modify the skin properties are highly desirable. What is needed are ways of permanently or semi-permanently changing the mechanical, thermal and chemical properties of the skin or other targets, such as by placing a layer or subsurface zone between the surface of the skin and the nerve ending to absorb shocks, mechanical pressure stress and strains, or mechanical vibrations. What is also needed are ways of disabling the nerve endings in the skin, which would mechanically, electrically or chemically interfere with the nerve-generated signal, and prevent it from traveling down the nervous system to create the sensation of pain.

Controlled and continuously delivery of drugs, medicines, nutrients, vitamins and other supplements constitute still other areas that are poorly satisfied by prior art methods and apparatuses. For example, patients with type 1 diabetes mellitus depend on external insulin (most commonly injected subcutaneously) for their survival because of an absolute deficiency of the hormone. Patients with type 2 diabetes mellitus have insulin resistance, relatively low insulin production, or both, and some type 2 diabetics eventually require insulin when other medications become insufficient in controlling blood glucose levels. Other than insulin pumps, the most common way for treating diabetes is for insulin to be injected into a patient, which over the long haul can cause all sorts of problems. What is needed is a way to intrinsically and permanently or semi-permanently modify the upper layers of the skin to create a permanent or semi-permanent zone for storage of such medically beneficial substances as insulin.

Considering the above, there is clearly an urgent need for a device and method for modifying a substance, and in particular the skin so it can preventing hazardous and undesirable external influences from entering deeper layers, in particular deeper layers of the skin and body. In particular, there is an urgent need for protection of the skin and body from harmful radiation and damaging sunlight. Such protection would both inhibit premature aging and more importantly, would reduce the risk of contracting skin cancer.

Certain types of skin cancers such as melanoma are especially deadly and have very low survival rates.

In short, there is still a very significant need for safe and effective, long term subsurface skin modifications that have little or no collateral or health repercussions.

SUMMARY OF THE INVENTION

The present invention provides apparatus, systems and methods in which an ultrashort pulse lasers or other device produce patterns of micro-disruptions, while minimizing collateral damage.

In some embodiments, the micro-disruptions comprise a plurality of cavities, voids, discontinuities or disruptions in the skin, which can be left as they are, be filled with air, gas, or other inert material, or be filled with biocompatible material, collagen, derma-filler, or any other substance safe for insertion under the surface of the material. All suitable filler substance are contemplated, including for example, drugs or medicines, vitamins, nutrients The end result is a change in the skin appearance, structure, or function.

Contemplated benefits can include long lasting skin protection from hazardous radiation, sunlight or other external influences. Other benefits can be cosmetic, enhancing natural skin tone, structure, and/or color, all without serious damage or serious risk to the body.

A method and a device for treating targeted material and targeted tissue are described. For Example, said method and device are directed towards the treatment of skin and subsurface structure of skin for removal of hair, skin protection from Sun light and other externally damaging effects, bacteria depositions, and reduction of hair, acne, sweat, wrinkles among other applications in the skin. Additional example of embodiments of the present invention are subsurface and surface treatment of the cornea, crystalline lens, retina and other ophthalmology applications in treatment of the eye.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 5b shows an embodiment for treating targets and ailment of the eye.

FIG. 6a is a schematic showing uses of the device and method to create subsurface disruptions for applications in various targets; and FIG. 6b shows further embodiment for treating targets and ailment of the eye.

FIG. 17 shows additional targets within the skin of ailment or targets that can be treated with the embodiments disclosed herein.

DETAILED DESCRIPTION OF THE INVENTION

Figure 1A:
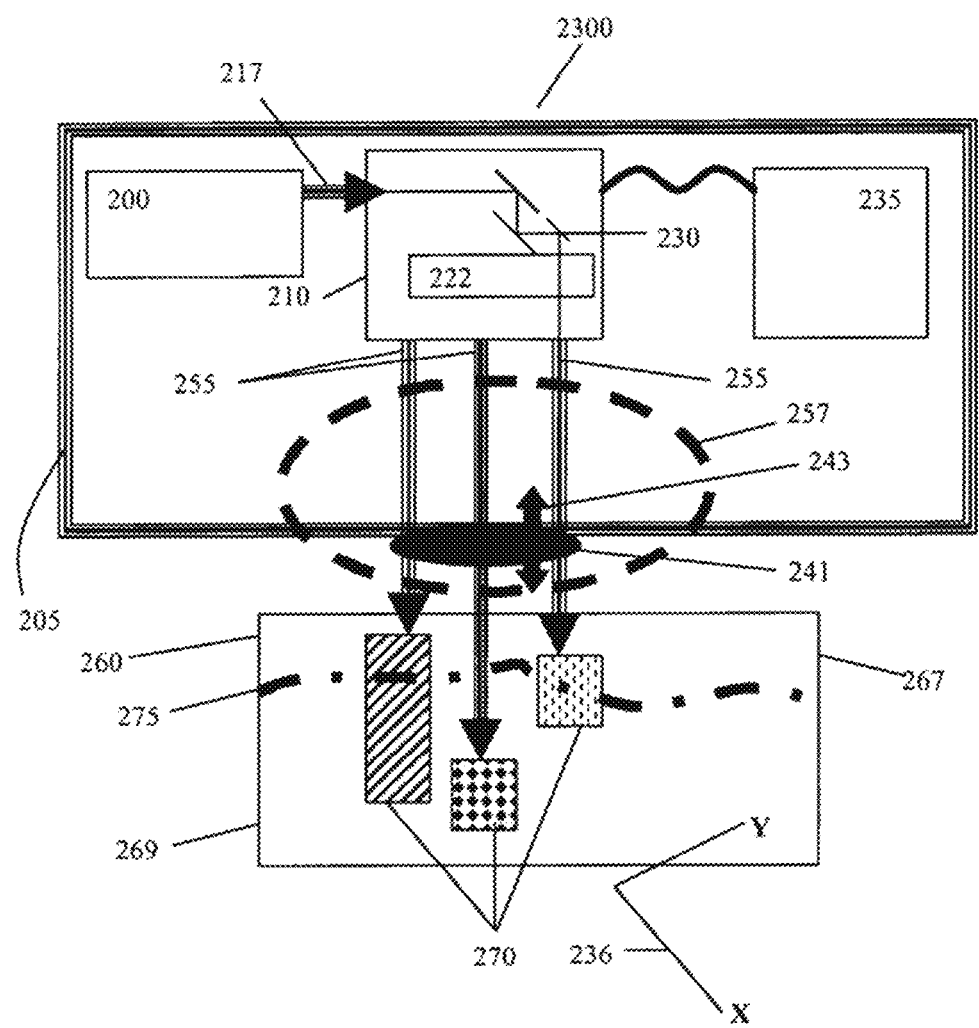
FIG. 1a is a schematic representation of a device that produces a plurality of energy beams using a scanner.

In FIG. 1a, a device 2300 generally includes a beam generator 200, an element, 210 capable of generating an array of beam 255 in an x,y plane 236, a lens 241, and a mechanism 243 that moves the focus of the beams in a z direction. In this particular embodiment, Ti:Sapphire oscillator 200 is used to generate ultrashort pulse of duration of less than about 10 pico-second. The pulses out of the oscillator 200 can be for example of energy ranging from about 0.1 nJ to about 1 mJ, from about 1 nJ to about 0.5 mJ. The pulse repetition rate of this pulse train out of the oscillator 200 can be from about 1 KHz to about 1 GHz, from about 10 MHz to about 100 MHz. These pulses may then be amplified by a light amplifier 210 to an energy range of from about 10 nJ to about 10 Joule, from about a micro joule to about 1 joule and a pulse repetition rate of form about 0.001 Hz to about 1 MHz, from about 1 Hz to about 1000 KHz.

The beams 255 that are produced can then redirected and shaped by optics and scanners assembly, 257. The optics and scanners assembly, 257, may include mirrors, lenses, beam splitters, scanners, motorized and mounted mirrors, rotating mirrors, diffractive optics, Kinofrom phase plates, diffraction gratings, and other optical components. The optics and scanner assembly, 257, then direct a plurality of beams to the targeted tissue or the skin 260. The beams are then focused below the surface of the skin 260, and create a region of a plurality of cavities, or voids or discontinuities in the skin in a plurality of layers. Such a region can be directed to target the epidermis 267 above the epidermal dermal junction 275, the dermis 269, below the epidermal dermal junction 275, or it can be created in both the epidermis and dermis regions of the skin. Some representative examples of possible patterns are shown by 270 in FIG. 1a and in more details in FIG. 2C. The different possible patterns of plurality of cavities, or voids or discontinuities in the skin in a plurality of layers are shown in FIG. 2C where the dark lines or spots or circles represents different cavities or voids or disruptions shapes, patterns, and layers.

Beam Generation & Characteristics

Beam generator 200 is preferably a laser, but can be any generator so long as the beam can be modified to an effective fluence of between about 0.0000001 J/cm$^2$ to about 100 J/cm$^2$. and preferably, between about 0.00001 J/cm$^2$ to about 10 J/cm$^2$ and more preferably between about 0.001 J/cm$^2$ and about 5 J/cm$^2$ and most preferably between about 0.01 J/cm$^2$ and about 2 J/cm$^2$. Many different wavelengths could work depending upon the absorption properties of the target. For example, where the target is human skin, wavelengths from 300 nm to 4 μm would work, more preferably 400 nm and 1.6 μm and most preferably between about 400 nm and 1.2 μm. For example a Ti:Sapphire oscillator with or without a regenerative amplifier can provide for example a train of pulses between about 60 MHz and about 90 MHz and a pulse energy of between 0.01 nJ and about 100 mJ and more preferably between about a nJ and a mJ of pulse energy and wavelength of about 800 nm that can then be frequency doubled or lengthen with an OPO or an OPA. For example lasers such as the Imra, Teem Microchip laser, Clark MXR Impulse™ or the Magellan Femtosecond/Picosecond, or the CPA-2101, or even the CPA-2210 2 mJ Amplified Ti:Sapphire Laser system with frequency doubling optics and OPO.

A preferred laser ultrashort pulse fiber laser from Imra Inc. of An Arbor, Mich. Or ultrashort pulse lasers such as the MaiTai from Newport Corp./Spectra-physics, or Coherent Corporation or a microchip laser nanosecond or sub-nanosecond passive Q-switch lasers from TEEM Corporation, or a micro-laser from ALTOS (Montana, USA).

Beams should have a pulse duration that produces the desired results without significant collateral damage. In most cases this means pulse durations of $\leq 10^{-3}$ seconds, more preferably $\leq 10^{-5}$ seconds, more preferably $\leq 10^{-6}$ seconds, more preferably $\leq 10^{-8}$ seconds, more preferably $\leq 10^{-9}$ seconds, more preferably $\leq 10^{-10}$ seconds, and still more preferably $\leq 10^{-11}$ seconds. Most preferably the beam pulse duration is between $10^{-15}$ second and $10^{-12}$ seconds. Repetition rate is preferably at least 0.5 pulses per sec, more preferably at least about 5 pulses per sec, more preferably yet at least about 50 pulses per sec preferably, and more preferably yet at least about 500 pulses per sec.

The beam intensity, duration and duty cycle will affect the characteristics of the skin disruptions. For example an ultrashort pulse train with pulse duration of about 10 ps or less and a pulse repetition rate of about 100 KHz or more, and energy per pulse of 1 microjoule or less can create disruption to spot sizes of 20 μm and smaller that consists substantially of thermal modifications to the material that change their refractive index. On the other hand, if for example said pulse repetition rate is below 100 KHz and said pulse energy is 50 microjoule and above, and said disruption spot diameters are about 20 μm and smaller (e.g., $\leq 10$ μm, $\leq 1$ μm), the disruption in skin like tissue may consists substantially of bubbles formation, said bubbles and subsequent structural changes in the skin tissue will result in modification to the index of refraction of the target.

Optics and Generation of Multiple Beams

All suitable optics are contemplated, including especially a diffractive element that produces the at least 3 beams. In preferred embodiments the device optic produces at least 10$^3$ or even 10$^4$ beams in the x,y plane. Lenses or other focusing elements are also contemplated, to focus the beams within a 1 mm$^2$ or other suitable treatment area.

The diffractive optics 222 (for example, (grating, Kinofrom Phase Plate (KPP)); generating an array of for example, a 7×7 or 49 beamlets. Kinoform Phase Plates and Multilevel Diffractive Beam Correcting Optics Kinoform phase plates for tailoring the focal plane irradiance profile. However, in another preferred embodiment, the beamlets array can take any shape desired, (for example, a trapezoidal shape or other shapes different than a regular, square dot pattern) and the number of beamlets can vary to any number desired as long as the beamlets spot size and the separation between adjacent beam edges is sufficient to fulfill the desired target or tissue effect. For example, as discussed elsewhere herein, the distance between beamlets edges must be sufficient to avoid separation or cutting of a segment of tissue and should not result in coalesce of more than 100 locations of target modification, for example location of skin tissue photodisruptions (and preferably less than 10 spots should be allowed to coalesce). For example, a pattern of from 3×3 beamlets per mm$^2$ to as many as 103 by 103 (or a total of 106) per mm$^2$ is contemplated herein. More preferably a pattern of about 5×5 per mm$^2$ to about 500×500 per mm$^2$ (or 2.5×105 beamlets per mm$^2$) is contemplated although in the sub-diffraction limit, multi-photon mode of photodisruption, if a focused laser beam used to generate such multi-photon effects in the target or tissue, and photodisruption effects of each beamlet are confined to less than 1 μm, than a limit of greater than 106 per mm$^2$ can be achieved. (For example a pattern bigger than even 9×106 photo-modified spots per mm$^2$ can be achieved).

Kinoform phase plates (KPPs) are beam shaping elements that enable a controlled modification of the focal plane intensity profile. The focal spot produced by the high power laser beams is often severely aberrated because of the optical wave-front errors. The KPPs can be designed to produce an arbitrary shaped intensity envelope in the focal plane. The phase plates are designed using a variant of the iterative Fourier transform algorithm (IFTA). The fine scale speckle superimposed on the intensity envelope can be smoothed using temporal beam smoothing methods known in the art. A preferred Kinoform Phase plate unit from the diffractive optics group at Lawrence Livermore National Labs.

Beams 255 can be for example an array of 7×7 or 49 beamlets each with a pulse repletion rates as described above and a fluence or energy as described above. The diameter of each beam can be for example from about 0.001 μm to about 300 mm, from 0.01 μm to about 300 μm and most preferably from about 0.1 μm to about 50 μm in diameter.

Lens 241 could be combined with the diffractive optics or Kinoform phase plate to generate multiple focused beams. The lens can be moved by an actuator or a motor or other moving element, 243. Alternatively, and lens can be a concave lens with focal length of from about 0.1 mm to about 50 cm, from about 1 mm to about 15 cm and most preferably from about 5 mm to about 5 cm focal length. The lenses diameter can be for example from 0.1 mm to about 1 m and more preferably form about 1 mm to about 10 cm and most preferably from about 5 mm to about 3 cm in diameter. Alternatively said lenses could be just multiple lenses, capable of focusing focuses all of beamlets, focal length 1-20 cm.

Mechanism 243 should be interpreted as including either a piezoelectric transducer, or stepper motor, or a stepper motor or other precise actuator known in the art, for example actuators for optics or precision applications from Newport corporation of Irvine Calif., or Thorlab corporation.

Alternatively, a mask can be used to generate multiple beams. That has the disadvantage that it waste some of the energy of incoming beam but it has the advantages of simplicity and low cost of simply inserting a mask with a hole pattern that blocks some of the incoming light while transmitting the rest to generate the desired pattern.

Mechanical Perforators

It is contemplated that at least some of the desired results can instead be achieved using mechanical perforators. For example, a plurality of needles capable of impinging on the skin with a kinetic energy sufficient to penetrate the top layer of the skin. Such perforators could advantageously create at least 10 perforations per mm$^2$, more preferably 100 perforations per mm$^2$, more preferably at least 500 perforations mm$^2$, and most preferably at least 1000 perforations mm$^2$. Mechanical perforators can be used to inject air, gas, or fluid into the perforations they create. For example, a plurality of hollow tubes, a plurality hollow needles, or a plurality hypodermic needles, can be plunged into the skin to a predetermined depth (for example to a depth above the epidermal dermal junction but below the skin surface), and then used to inject gas or fluid into the targeted dermis. When the needles are withdrawn, they leave behind a hollow spots in the epidermis that are filled with gas or fluid.

Characteristics of Surface Disruptions

Regardless of whether energy beams or mechanical perforators are used, devices contemplated herein can produce at least 10 subsurface disruptions per mm$^3$ in a region of treated skin region. It is especially contemplated that the disruptions can be imparted in a 3-dimensional pattern, for example using a transducer or stepper motor that displaces one or more of the optics by increments of less than 50 μm in a z direction. To that end, devices can include a piezoelectric transducer, for example a P-290 long-range piezo translator, with 1 mm travel from Physik Instruments™. By including a z dimension in operation of the device, multi-layer patterns are contemplated that include ≥100 disruptions per mm$^3$ of the target, more preferably ≥10$^3$ disruptions per mm$^3$ of the target, more preferably ≥10$^4$ disruptions per mm$^3$ of the target, more preferably ≥10$^4$ disruptions per mm$^3$ of the target, more preferably ≥10$^6$ disruptions per mm$^3$ of the target, and even ≥10$^7$ disruptions per mm$^3$ of the target.

Subsurface disruptions produced using devices and methods described herein are preferably at least 90% non-ablative. In progressively less preferred embodiments, the subsurface disruptions are ≥80% non-ablative, ≥60% non-ablative, ≥50% non-ablative, ≥40% non-ablative, and ≥30% non-ablative. As used herein, the term "non-ablative" means that the surface remains substantially intact, and the subsurface disruptions produce little or no thermal damage deeper than 5 μm of at least 80% of the disruptions.

Pattern of voids or micro-photo-disruptions (MPD) can range in size from 0.1 μm to about 20 μm and can be packed a density of up to about 1 million in a volume consisting of an area of 1 cm$^2$ by about 100 μm deep layer, for example of the epidermis. These tiny spaces are equivalent to scattering centers for example in a cloud, giving which prevent light from penetrating deep into the tissue. In addition the short wavelength scatters more by the size of these scattering centers giving rise to additional protection.

In addition to being non-ablative, it is preferred that no more than 100 of the subsurface disruptions coalesce into a structural discontinuity. That restriction is intended to prevent separation or cutting off of a part of the target from the rest of the target material.

The operating values chosen to produce non-ablative skin disruptions will depend upon many factors, including the equipment used and the desired treatment. For example, an ultrashort pulse laser operating with pulse energy below ablation threshold but at power density at a focal point that are sufficient to result in increased absorption in said focal region. The pulse repetition rate is then sufficiently high to result in accumulation of heat substantially mostly in said focal region that thermal energy accumulation yield irreversible changes to the target material, for example skin tissue, so that the index of refraction is changed resulting in a reduced transmission of electromagnetic energy to regions below the zone of target modification. For example, a Ti:Sapphire ultrashort pulse laser (with pulse duration shorter than about 10 ps) operating at a pulse repletion rate of 88 MHz, and with pulse energy of, for example, between about 0.1 nJ (nanoJoule) per pulse to about 500 nJ per pulse, and preferably between 1 nJ per pulse and about 100 nJ per pulse. The energy is preferably focused to one or more regions in the epidermis below the stratum corneum and above the epidermal dermal junction, to a spot size between about 0.1 μm and about 0.5 mm in diameter, between about 1 μm and about 100 μm.

Figure 2A:
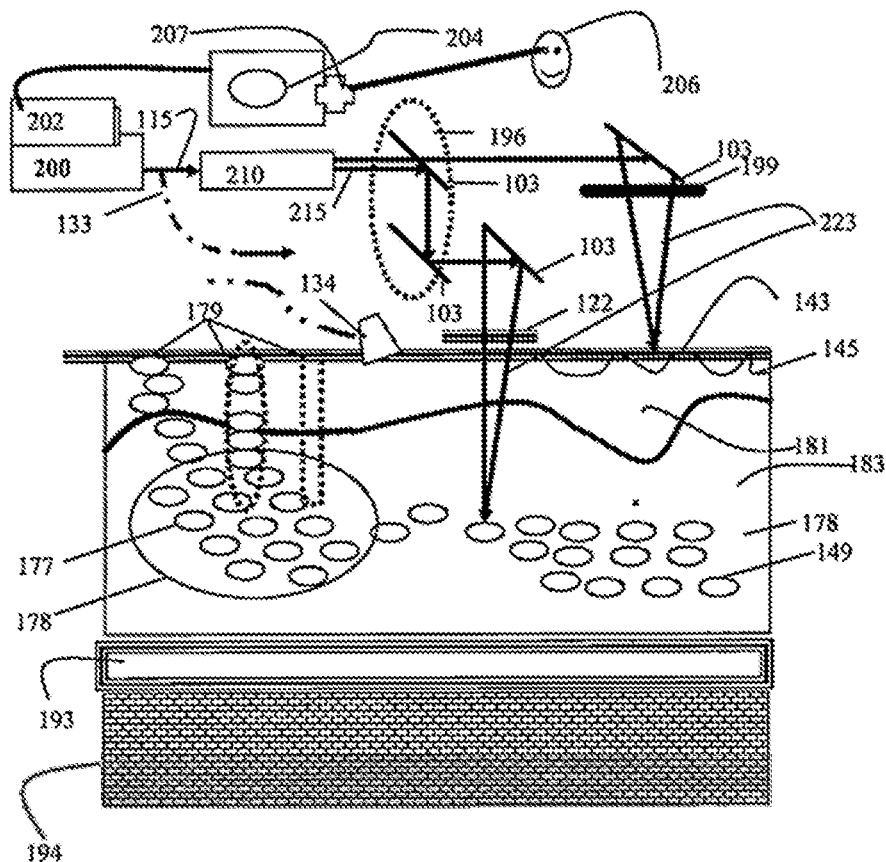
FIG. 2A is a schematic representation of a device that produces a plurality of energy beams using a scanner or a diffractive element.

FIG. 2A shows a device that produces a plurality of energy beams using a scanner, 196. Scanners are devices made of movable mirrors or lenses capable of moving the beam in space. For example, a stepper motors or galvanometers are used to move mirrors or lenses. When two mirrors are mounted on two separated stepper motors, one can move the beam in the x direction and the other in the y-direction to create patterns in the x-y plane. A transducer mounted lens can then move the beam in the z-direction (in and out of the tissue) to create a multiple planes of scanner-generated patterns. All suitable scanners are contemplated, including scanners from the GSI Group Inc. or from Cambridge Technology, Inc. Galvanometer scanners Models: 6200H|6210H|6215H|6220H|6230H|6231HC|6240H.

Figure 2B:
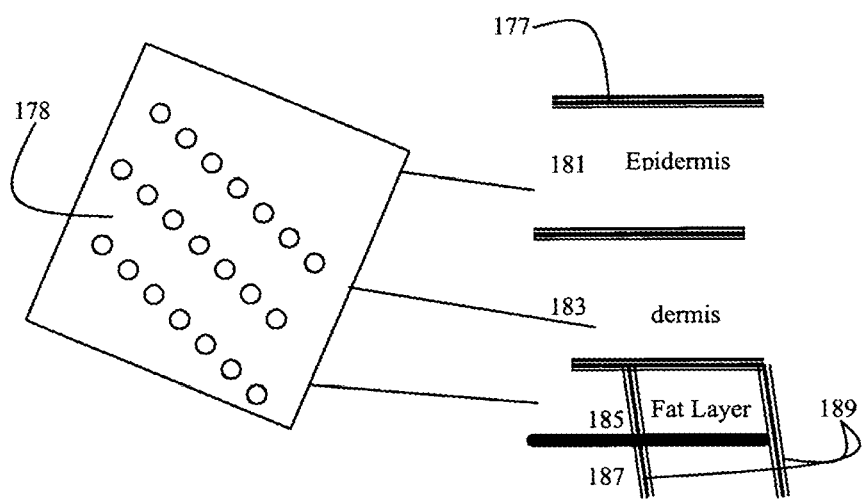
FIG. 2B is another schematic representation of the device of FIG. 2A producing a plurality of energy beams that impact a region of skin.
Figure 2C:
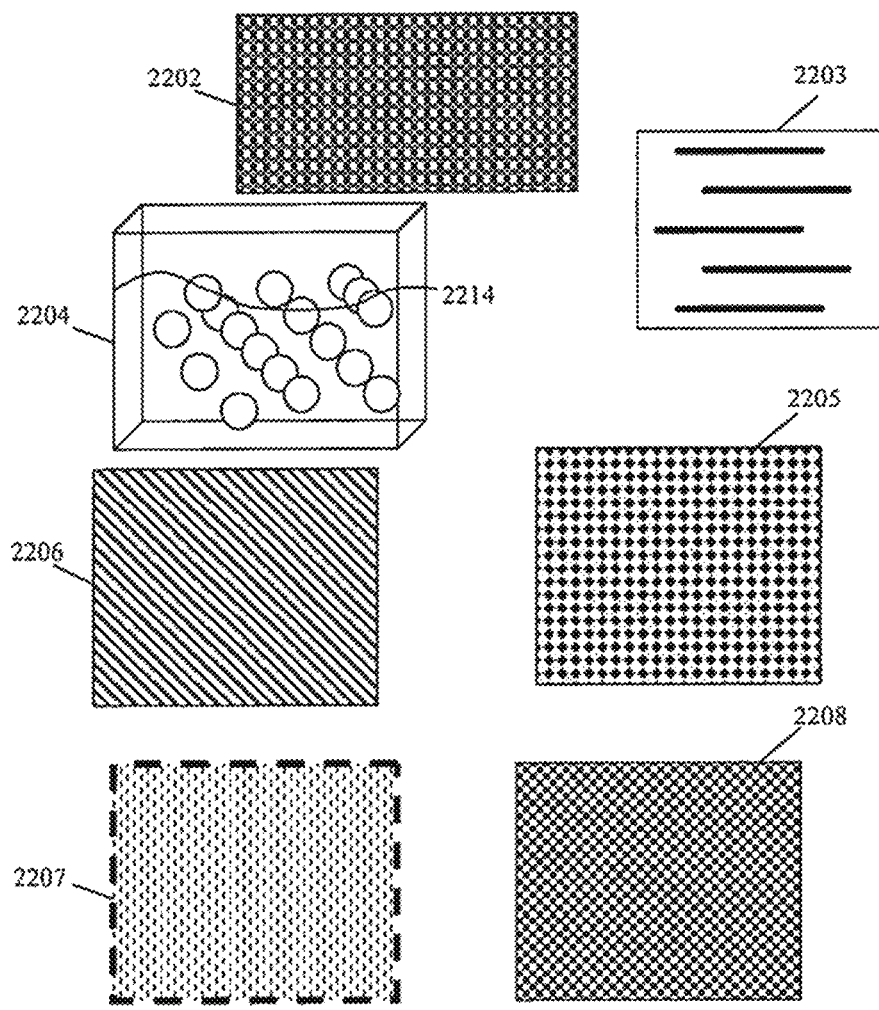
FIG. 2C is a schematic representation of examples of various subsurface patterns of micro-spots and micro-lines that can be generated by the disclosed device and method.

In FIGS. 2A and 2B the energy source 200 generates a beam that may or may not be amplified by the amplifier 103, for example a chirp pulse amplifier for an ultrashort pulse laser oscillator's energy source. The amplified beam then enters into a scanner 196 composed of mirrors 103, for example motorized mirrors mounted on stepper motors or galvanometers or actuators, the mirrors then stir the beam 115 across the focal x-y plane 117. The beam can be focused by the focusing element 122. Alternatively, the beam may not be amplified but take the pass 133.

FIGS. 2A and 2B also show the device utilizing ultrashort pulse lasers (laser generating pulses shorter than about 10 picoseconds) for the creation of such subsurface voids. The device consists of an oscillator 200, from which the beam is directed towards an amplifier (for example) a CPA amplifier) 210 and then through a plurality of mirrors, 103, and a plurality of scanners 196, to a the targeted skin 183 where a pattern of three dimensional voids or cavities 178 are produced in a predetermined manner in the tissue or skin 183. When the targeted tissue is a skin the components of a skin are the surface with the stratum corneum 177, the epidermis 181, the dermis 183, the fat layer below the dermis 185, or even preferably the muscle tissue 187 or cellulites 189. The pulses out of the amplifier 210 can be for example in the range of about 800 nm and from about 3 fs to about 10 ps and with energy of from about 50 nJ to 50 mJ, from about 0.5 micro joule to about 5 mJ. The pulse repetition rate can range from single pulses at for example from about 0.01 Hz to as high as 500 KHz, at about 0.5 KHz to about 100 KHz. The wavelength can be chosen such that at the surface where the beam is wider, the linear propagation in the skin or tissue is good e.g. from 1300 nm to 400 nm, while at the focused points the Multi-photon process create a nonlinear interaction and photodisruption that creates the voids or a cavity. Wider range of wavelengths can be used as well as OPO and OPA or non-linear crystals to extend the range of the wavelengths used from the UV to the mid IR. The scanners 196 or an optional diffractive optics 199 or Kinoform plates 199 can be used to create multiple beamlets and pattern of cavities and voids from a single beam.

Alternative embodiments envision envisioned using the oscillator 200 beam 215 at higher pulse energy. Such oscillators often operate at very high pulse repetition rate of from example 50 MHz to about 100 MHz and pulse energy of about 0.1 nJ to about 100 nJ. Most typically oscillator beam 215 has pulse rates form about 60 MHz to about 90 MHz, and pulse energy in the nJ. Such beams will create a selective interaction regions where the at the beam focus below the surface of the skin, 143, the non-linear absorption of the multi-photon create an interaction and absorption but no cavity but rather of selective heating at the target location.

FIG. 2C shows various possible patterns for volumetric patterns of micro zones. 2202 shows a multilevel of crossing lying. 2203 shows a displaced microclines wherein individual spots coalesce to form lines of modified tissue. 2204 shows a pattern of discrete micro zones of modified tissue distributed through the targeted volume (which include both the epidermis and dermis) in a random manner and in pattern resembling diagonal lines. 2205 shows a regular pattern of modified and unmodified spots forming a lattice. Similarly 2208 shows a different spot size and shape than 2205, yet regular pattered of modified and unmodified spots forming a lattice. 2206 shows a pattern of individual micro-zones that coalesce to form a series of diagonal lines of modified zones. 2207 shows a pattern of interrupted dashed lines that form a pattern of short lines of modified micro-zones. Similarly, many other patterns of modified subsurface modified volume that can be created or embodiments envisioned by the present disclosure and the device and method it contemplates.

In conjunction with the current teachings, those skilled in the art should be able to design appropriate patterns to achieve the desired results. For example, if the desired result is to achieve maximum protection from UV and skin cancer-causing radiation, (e.g. radiation in the range of 150 nm to 450 nm), then a pattern can be design to achieve multiple scattering that minimize forward scattering by such wavelength. For example, the molecules and particle in the air upper atmosphere tends to favor lateral scattering of short wavelengths and for this reason we see the sky as blue. On the other hand, a cloud saturated with water droplets tend to scatter all wavelengths and for this reason clouds often appear as white or gray, depending on the amount of light that ends up being absorbed by the water in relation to the light that is scattered. In one case water droplets ranging in size from 1 μm to 20 μm are present to generate the effect of white light scattering. In the other, molecules ranging in size from pico-meters to about 0.01 μm create the enhanced blue to UV light scattering.

Figure 3A:
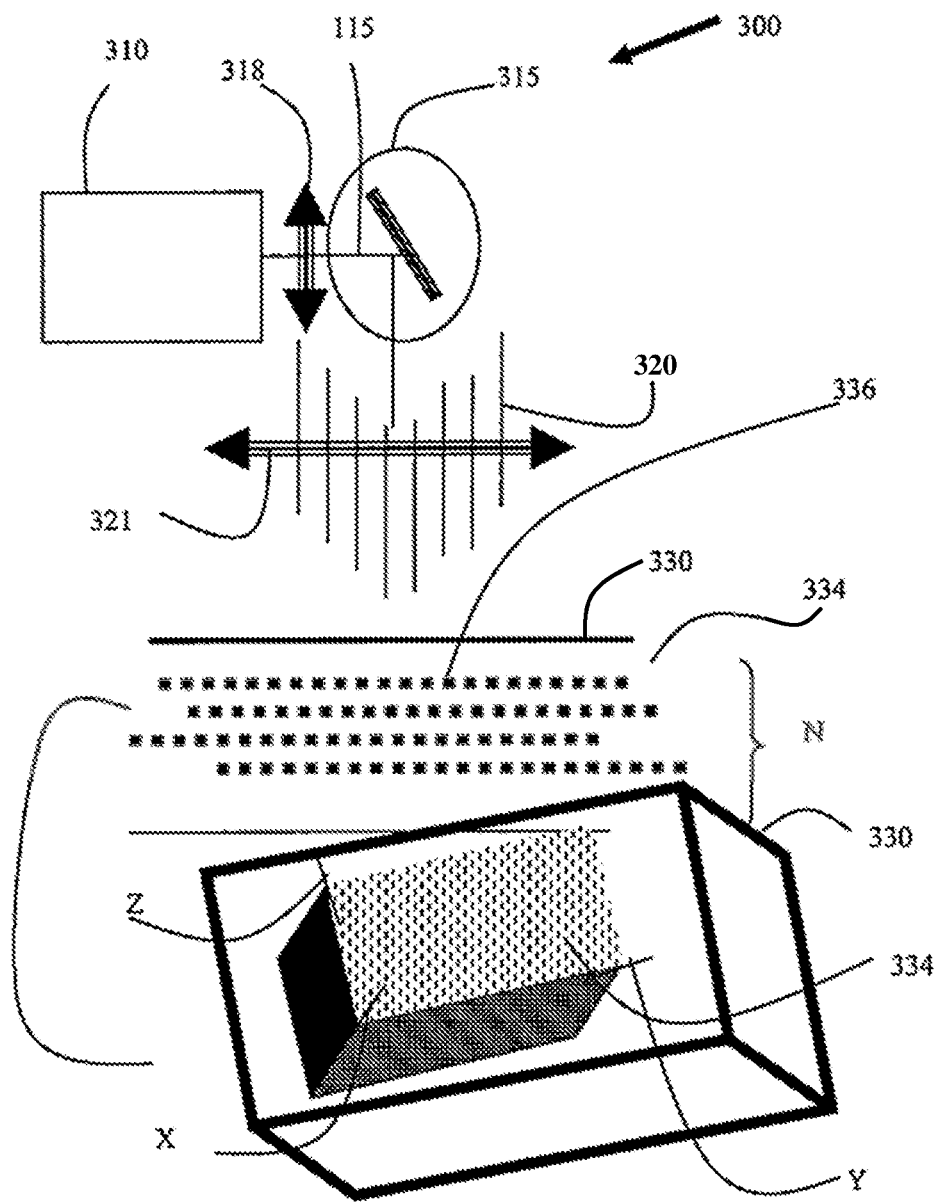
FIG. 3a is a schematic of ways to generate a three dimensional pattern of subsurface disruptions in a target.

In FIG. 3a, an energy source 310 generates a beam 115 that can be modified by a scanner or diffractive optics or a mask with lenses and holes or a pattern of holes, 315 to create an array of multiple beams 320. This array of multiple beam, 320 is then directed toward a surface of a target 330 (the target, 330 can be human skin, animal skin, fruit, vegetable, cell, organelles, or other material to organic or inorganic to be process or protected). The beam 115 can be focused by a focusing element, 318, for example a lens, or a plurality of lenses, to a focal plane 336 underneath the surface 330. Alternatively, in a preferred embodiment, part or all of the array of beamless 320 can be focused to with a focusing element 321. In either case a pattern of modified target material, for example, a pattern of modified spots in the focal plane 336 is generated. By moving the focusing element 318 or 319 a sequence, N, of modified plane consisting of an array of modified spots in the target material, for example, underneath the surface of a human skin, is thus generated. By moving the scanners or mask pattern or diffractive optics so that the patter of modified spots is moved in the x-y plan, and by moving the focusing element so that the focal plane 336 is moved in the –z or +z direction, an entire volume, 334 of the target material, 330, for example, a human skin, is generated.

Those skilled in the art can then design a pattern and density of spots to optimize scattering and backscattering of for example light to block ultraviolet (UV) radiation. For example, one of the most damaging UV radiations is in the range of from about 200 nm to 330 nm. Since the extent of scattering is inversely proportional to the wavelength, shorter wavelength will scatter more strongly. Thus to maximize scattering one should generally reduce the size of the scattering centers. For example if the scattering cavities created by the device are large and few, the light photons will continue in its forward propagation. However, a large number of scatterers introduced in the path of the harmful radiation so that a significant backscatter is created and thus permanent of semi-permanent blocking of the light from propagating into the skin.

It is also possible to introduce a sufficient number of scatterers so that only a given light color back scattering is maximized. This will allow one to "paint" the skin, in effect creating an artificial and very safe tanning effect without the risk of harmful radiation and with the added benefit of creating a layer of protection built into the skin. This tissue or skin engineering can be optimized for color and protection.

One can also micro-sculpture of the skin and present surface. For example ridges in wrinkles can be flatted at least partially by creating physical voids or cavity below their surface. Alternatively, voids and cavities created under the surface or troughs or valleys in wrinkles can be filled with various substances such as derma-filler to create support for overlying layers and thus be pushed up by an injected of fillers. Fine tuning can be achieved by removing or ablating such filler substances with the vaporizing action of the lasers or other light sources.

Scattering centers and scattering patterns can be generated to enhanced desired effects. For example, if a changing the skin color is desired, for example, to create a lighter, whiter color, a pattern similar to water droplet can be generated. Additionally and preferably, if the intent is to reduce transmission of light, a layering similar to the layering of cover slips that creates a diffractive index layering with layers space between a few hundreds nanometer to a few μm to a few tens of μm can be created. In addition, the created spots or material modification can be filled with substance capable of absorbing some or much of the incident radiation or light to enhance even further the effect of blocking or reflecting the incoming light.

If for example a series of tissue modified spots are created, the size of the spots can then vary in diameter from about 0.01 μm to about 5 mm, from about 0.1 μm to about 1 mm and more preferable from about 0.2 μm to about 500 μm and more preferably yet form about 0.2 μm to about 200 μm and more preferably from about 0.3 μm to about 100 μm, and more preferably yet from about 0.4 μm to about 50 μm, and more preferably yet from about 0.5 μm to about 25 μm, and more preferably from about 0.7 μm to about 10 μm, and more preferably from about 1 μm to about 5 μm.

Spacing between the edges of spots can also vary, for example, from about 0.01 μm to about 5 mm, from about 0.1 μm to about 1 mm and more preferable from about 0.2 μm to about 500 μm and more preferably yet form about 0.2 μm to about 200 μm and more preferably from about 0.3 μm to about 100 μm, and more preferably yet from about 0.4 μm to about 50 μm, and more preferably yet from about 0.5 μm to about 25 μm, and more preferably from about 0.7 μm to about 10 μm, and more preferably from about 1 μm to about 5 μm.

Figure 4B:
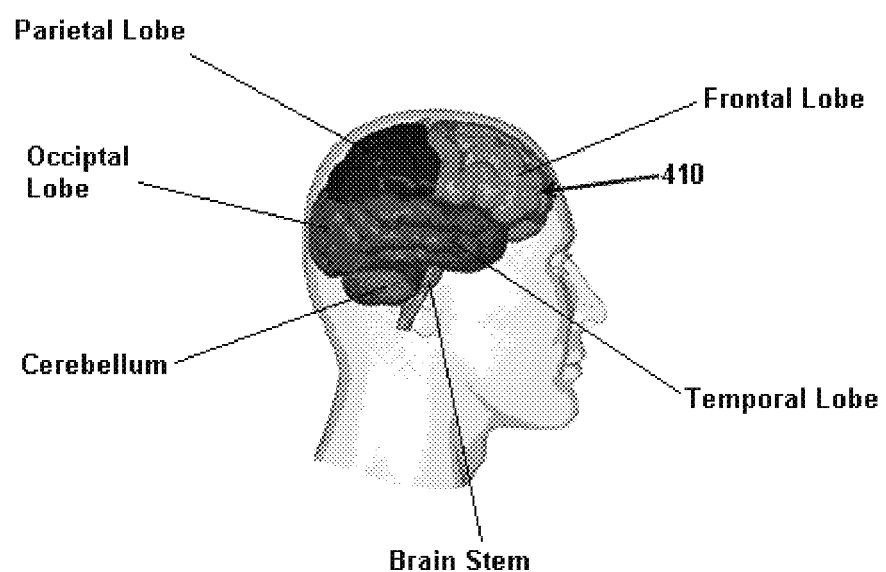
FIG. 4b shows another embodiment for targets of treatment in the skull and brain
Figure 4A:
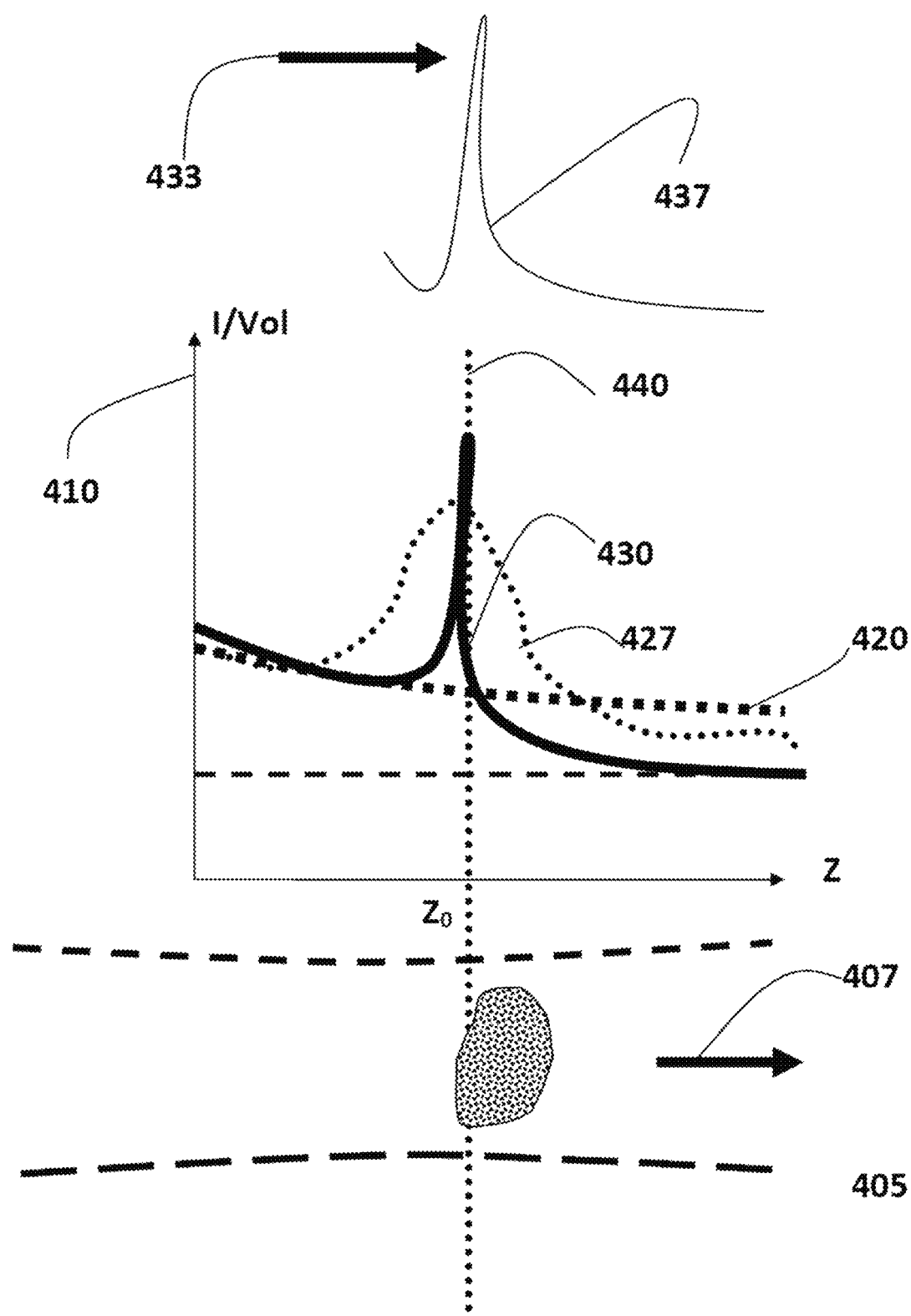
FIG. 4a is a schematic showing the theory behind production of subsurface disruptions including temporal pulse compression, spatial and temporal photon concentration, and absorber-initiated seed electron generation.

FIG. 4a is a schematic showing the theory behind production of subsurface disruptions. A beam 405 is propagating into the material in the z-direction as indicated by the arrow 407. The beam is focused onto a lane indicated by the dotted line 440 at location Z=Z0 below the surface (assuming that the surface of the material is located at position Z=0.

Normal light absorption (linear light absorption, often follows Beer Law of exponential decay in the beam power density as it propagate deeper into the target in the Z direction. However, if the target material is substantially transparent in the wavelength of the light or energy launched into the tissue, or target material (for example 532 nm light propagating through water-like material, then the absorption is very week as shown by the curve 420. Note that the arrow/axis 410 indicates the amount of energy absorbed per unit time per unit volume. However, if the beam is intense, for example an ultrashort pulse beam of pulse duration of about 10 ps or less, then as the beam approach its focal spot position in the medium, for example at point Z0, then multi-photon absorption initiate non-linear absorption and the absorption suddenly increase very rapidly. This process is indicated by the curve 430 and can occur in highly rarefied gases, air, water or glass, medium even for wavelengths that are characterized by low absorption such as light of wavelengths between about 500 nm and 800 nm in water-like media. Note that the amount of energy absorbed per unit time per unit volume significantly drops for points past the interaction point, as much of the beam energy has been absorbed by the volume affected by the non-linear absorption process and little energy remains for absorption in section of the target past the focal point. The absorption and loss at the focal point Z0 are less significant if non-linear heating occurs at lower pulse energies where non-ablative processes occurs without photo-disruption, optical breakdown, ablation, or plasma formation which are the characteristics of high pulse energy interaction.

Figure 5A:
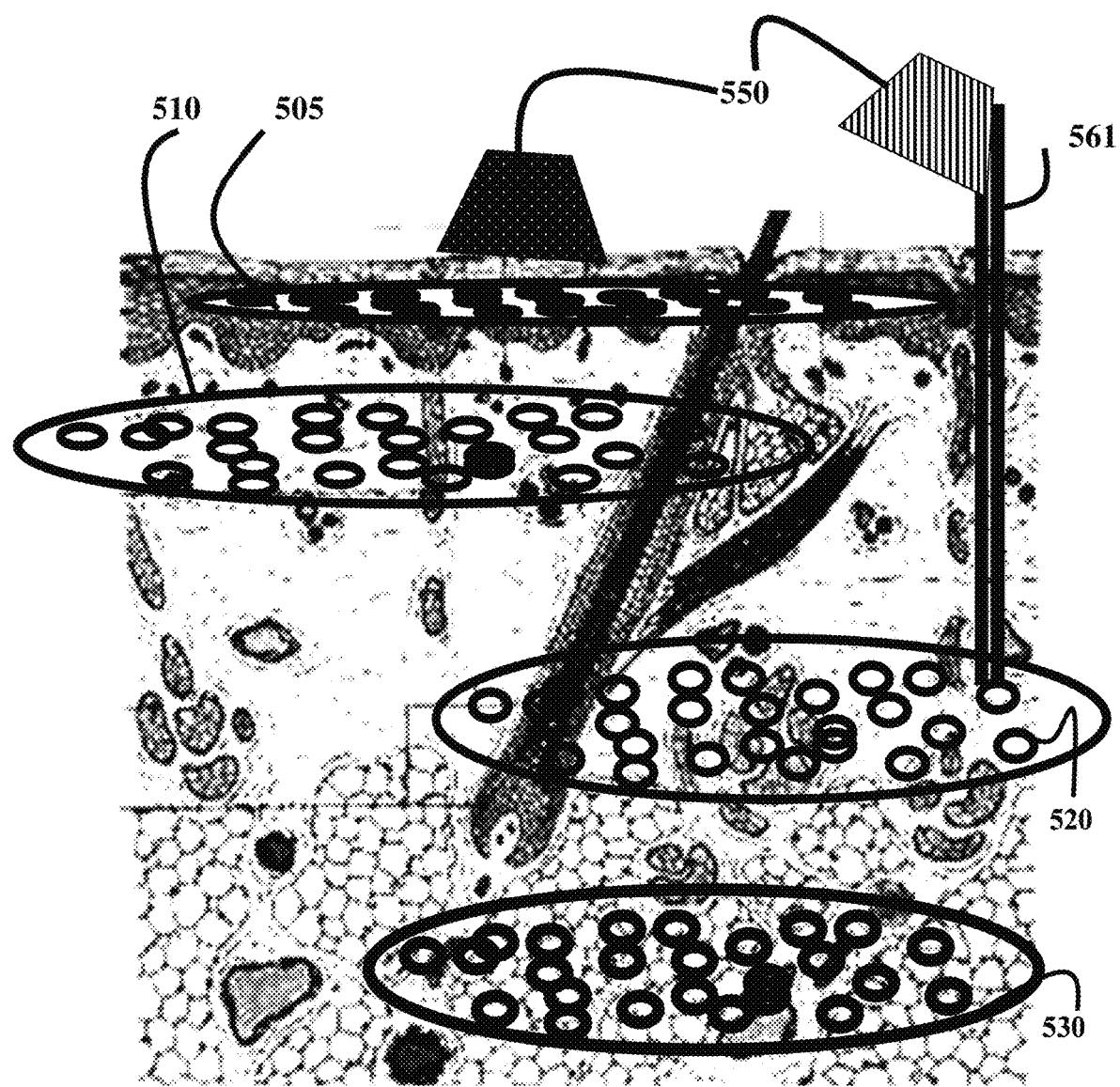
FIG. 5a is a schematic showing the production of subsurface micro-disruption patterns in various targets in the skin and representative detecting and imaging elements to monitor the tissue modification.

FIG. 5a is a schematic of subsurface disruptions generated at various targets depths. For example 510 is a pattern of photodisruption produced in the upper reticular dermis, a destruction patter aimed to disabled the sebaceous gland among other possible targets. The FIG. 5a also shows an imaging head, for example, and ultrasound or OCT imaging heads, 550, aimed to monitor and visualizing the destruction patterns as they occur. Similarly, in another preferred embodiment shown in FIG. 5a, a pattern of modified tissue, 505, 510, 520, or 530 is shown in the epidermis, upper, and lower reticular dermis, or in the adipose layers, respectively, aimed at disabling or damaging the hair root or hair matrix or for the destruction no the fat layer by the pattern 530 in the adipose layer.

FIG. 6a is a schematic showing uses of subsurface disruptions in various targets. For example, in humans a principle surface designated for modification is the surface of the skin. Within the skin, for example, hair follicles can be targeted. As discussed elsewhere herein the targeting of hair follicles can be accomplished in conjunction with monitoring using imaging systems 620 such as optical coherent tomography (OCT), ultrasounds, polarized light or other imagining devices and methods. Such imaging may also be used in any or all of the following:

FIG. 6a also shows the following: Targeting of other skin ailment such as acne, tattoo. color changes, and tanning; Modifying the skin to insulate against thermal, electrical, acoustical/mechanical, cancer protection, biohazard, chemical or thermal intrusions; Targeting hair roots and hair root system (blood vessels, matrix cells, papillae, etc. with 3D interaction and imaging system; Targeting papillae with 3D interaction and imaging system; Ablative and non-ablative modeling of the cornea or other region of the eyes for corrective eye sight surgery; Targeting of eye related ailments in humans; Targeting cells, organelles, eggs, embryos, and sperm; and Targeting of the surface or skin of fruits and vegetables, animal and animal skin, drugs and medicine as well as pills, for example for the modification of drug release rate through the surface of pills or capsule, or for example for the protection of seeds or fruit from diseases, germs, microbes or chemical, physical (e.g. thermal and mechanical) or environmental and biological hazards.

Figure 7A:
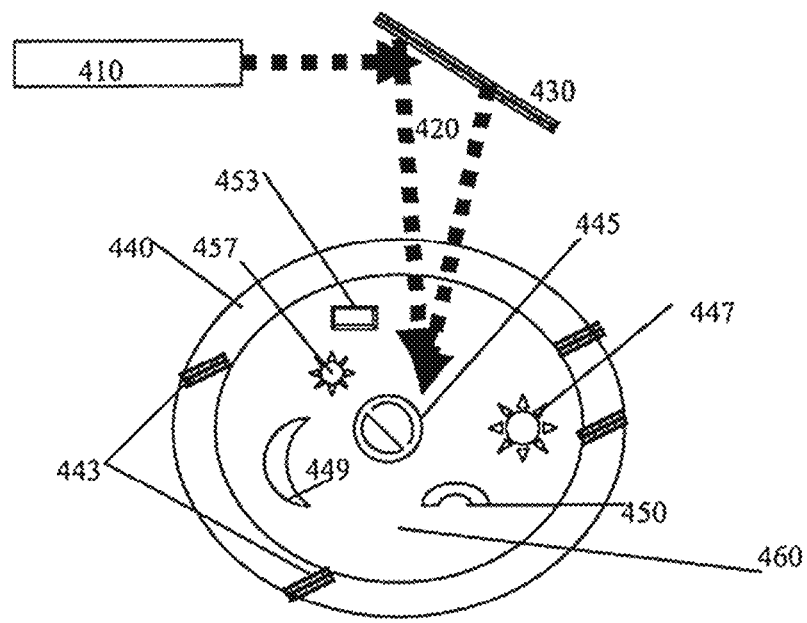
FIG. 7a is a schematic showing multi-photon interaction in selective cell targets and the creation of pattern of modified cells structures for creating enhanced protection or enhanced penetration in cell membrane, cellular components, and the manipulation of cell membrane properties.

FIG. 7a is a schematic showing creation of a subsurface pattern of modified microtones in cell structures. Here, a beam from an ultrashort pulse energy source 410 is focused on the cell membrane 440 for example, to achieve modification of the ion the size or other characteristics of the ion channels 443, or for example, to achieve selective destruction or inactivation of one or more of the following: ribosome 457 mitochondria 449, nucleus 445 or nuclear pore, or nucleolus, or endoplasmic reticulum, or Golgi Apparatus 447, or other organelle in the cell, or simply to achieve localized heating of the liquid inside the cells 460 or achieve chemical or physical changes of the liquids inside the cell 460.

Figure 8A:
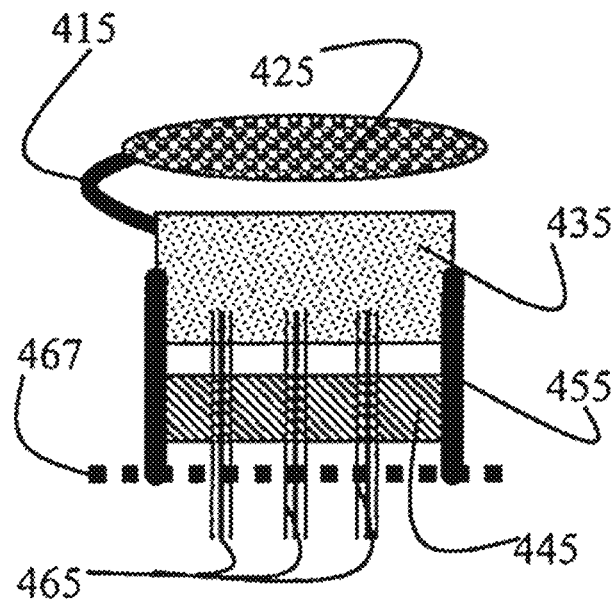
FIG. 8A is a schematic representation showing a mechanical device for the creation of subsurface modifications patterns.

FIG. 8A is a schematic representation showing a device for the creation of subsurface modifications patterns using mechanical penetration of the surface. In this embodiment a plurality of cavities, or discontinuities or disruptions in the continuity 330, can be created by other energy means aimed to create such a layer 330, such as a plurality of focused ultrasound beams or electrical probes inserted into the tissue and cable of creating transient bubbles and cavities, or radio frequency energy source or microwave energy, or chemical energy or thermal energy or mechanical energy.

Figure 8B:
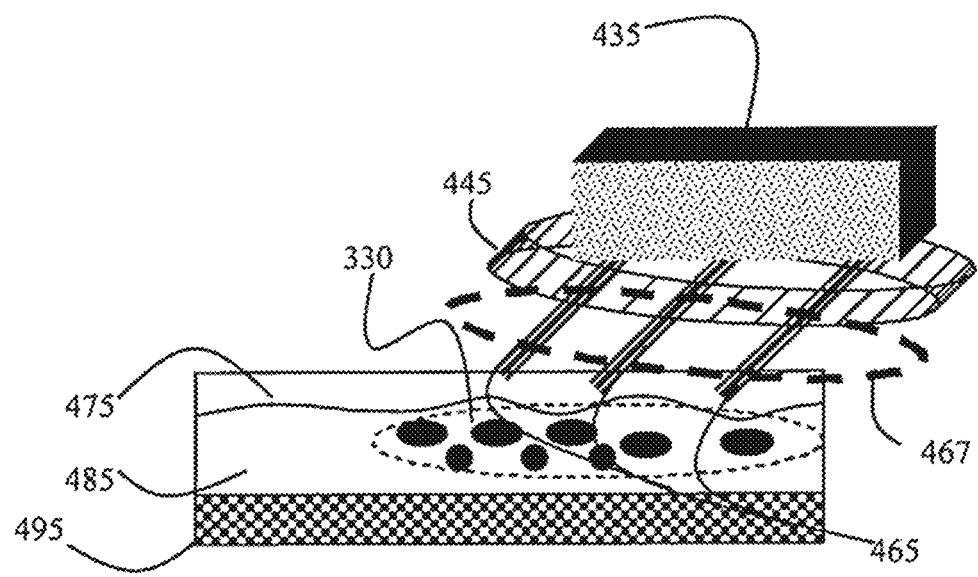
FIG. 8B is another schematic representation showing a device comprising sharp hollow members and a guard for the creation of subsurface modifications patterns.

In FIG. 8B, a plurality of probes or hollow tubes or hollow waveguides 465 are inserted into the skin or tissue into the targeted region of the skin where the plurality of cavities, or voids or discontinuities or disruptions in the continuity of the skin or tissue 330 layers are to be created. The skin and or tissue target can be composed, for example of an epidermis, 475, a dermis 485 and subcutis or hypodermis, 495, and possibly even deeper, a fat layer and muscle or even bone layers. The probes which can be hollow waveguide or hollow tubes, 465 can, in a preferred embodiment, be pumped with air or a gas (such as an inert or safe gas such as nitrogen or CO2) held in a reservoir 425 to create and inflate the plurality of cavities, or voids or discontinuities or disruptions in the continuity 330.

Alternatively the probes 465 can also be energized electrically to create rapid heating through an electrical resistive heating, or rapidly discharged with a plurality of higher voltage capacitors to create rapid vaporization, rapid heating or to generate plasma which then expend as like a gas and with the gases such plasma crease, some or all of these technique can also generate gases and or a plurality of expanding bubbles that leaves behind the mechanical voids or cavity, such plurality of expansions create a plurality of cavities, or voids or discontinuities or disruptions in the continuity 330. A plurality of holders 445 holds the hollow waveguide or hollow tubes firmly in place and a plurality of guards 467 defines the length of hollow waveguides or tubes or needles 465 that can penetrate the skin surface, and thus how deep will such needles or tubes reach (e.g. to the dermis, 475, to the epidermis, 485, to the fat layer, 495 or even deeper yet). The gases, compressed air, air, medicine, drugs, vitamins, nutrients, disinfectant, antioxidants, stem cells, or any other desired substance are held in the reservoir 435. The substance injection can be initiated and controlled by the control unit 415. The length of the tubes, or needles or hollow waveguides (HWG) that is allowed to penetrate the surface of the skin and be inserted into the skin is determined by the position of the guard layer, 467. Said guard layer can be moved up or down a rail 455 and be fixed in place for the operation itself. The position of the guard layer 467 can also be controlled by the controller 425 which can communicate with the rest of the device through a cable 415.

Epidermis is divided into several layers where cells are formed through mitosis at the innermost layers. They move up the strata changing shape and composition as they differentiate and become filled with keratin. They eventually reach the top layer called stratum corneum and become sloughed off, or desquamated. This process is called keratinization and takes place within weeks. The outermost layer of epidermis consists of 25 to 30 layers of dead cells FIG. 8B can also be viewed as showing a method for controlling the color an appearance of the skin while at the same time allowing the user to provide protection to the skin from harmful sun rays, external radiation such as for example, electromagnetic radiation, infection, contaminants, or other undesired external influences. Here, cavities, voids or discontinuities in the skin in a plurality of layers 330 can be injected with dye or ink, or any other substance that help change the color and appearance of the skin. Said substance can be held in the reservoir 435 and injected into the cavities or void or discontinuities or disruption 330 immediately after their creation or even creating such plurality of cavities, or voids or discontinuities in the skin in a plurality of layers, 330, after the HWG or tubes or needles, 465 are inserted to the target depth.

The tubes, hollow wave guides (HWG) or needles 465 can deliver laser, USPL radiation, or other energy forms capable of creating such cavities, for example, ultrashort pulse laser radiation capable through multi-photon interaction to create the cavities or voids or disruptions 330.

Alternatively, the tubes or ultrashort pulse laser radiation can create the cavities or voids or disruptions 330 at the region 330 below the skin surface (for example, dermis 485, epidermis, 475, or hypodermis, 495). In choosing between the two, it should be appreciate that focusing of light pulses at the target area below the surface can produce the desired effects without penetrating the skin mechanically, but instead only through the propagation of the beams of light.

Figure 9A:
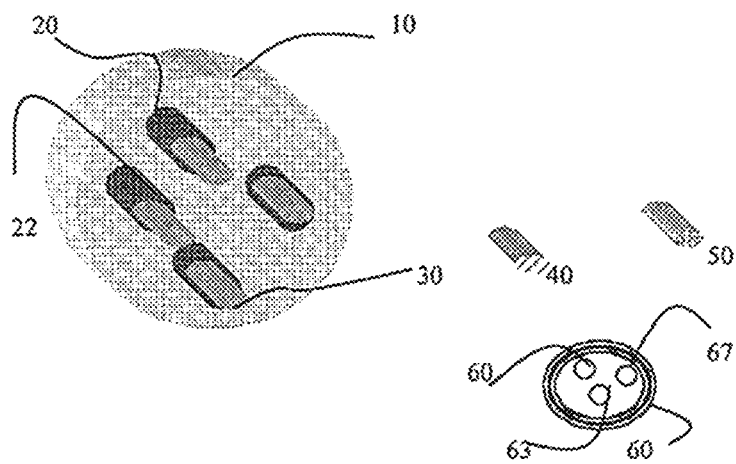
FIG. 9a is a schematic illustration showing a device for removing a plurality of fat cells including a hollow guides for penetrating the skin, injecting absorber in the region of the fat cells and a guide to deliver the source energy.

FIG. 9a shows illustrate another preferred embodiment of a multi-fiber fat removal system. Here, a plurality of needle tubes 20 are embed in the treatment caps. A plurality of hollow needles 30 can be inserted through the tubes 20 into the skin through the epidermis, dermis and into the fat or other target tissue. Once in the target tissue the hollow tubes 30 are used to conduct high absorbing substance into the fat or other target tissue layer. Once the absorbing substance is dispersed into the target fat or tissue layer, the plurality of tubes 30 are withdrawn and a plurality of optical fibers or HWG 40 are inserted and in the place of the hollow tube 30. The light source connected to the fibers or HWG 40 is activated and interacts selectively only with said high absorbing substance to destroy tissue and or remove or melt or otherwise denature fat. Once said light or energy conducted through tubes 40 is completed, hollow tubes 50 can be inserted to remove said fat or other tissue.

Alternatively, said tubes 50 can be inserted in parallel to fibers or HWG 40 to act in parallel to or immediately after the light or EM energy or energy action, to remove said destroyed tissue or fat as soon as possible. Preferably and additionally an imaging system can be used to guide and monitor the interaction of the source energy with the fat cells and to assure safe end point for the destruction of the fat cell with minimal collateral damage to adjacent tissue.

FIG. 9a also shows a view of the opening of such hollow guides or hollow syringes for the removal of fat, 60. They include a fiber or a hollow waveguide for the delivery of energy or light, 63, a guide or hollow tube for the delivery of dye or high absorbing substance, 55, and optionally a guide or a hollow tube for the removal of debris and fumes. Alternatively preferably, the tubes for the delivery of light can be separate from the one for the delivery of high absorbing substance or high absorbing fluid or dye. For example, the tube for the delivery of light can be the tube 20, and that for the delivery of high absorbing substance or high absorbing fluid or dye is 22 and the tube or hollow guide for the removal of debris or gases is 30.

Figure 10A:
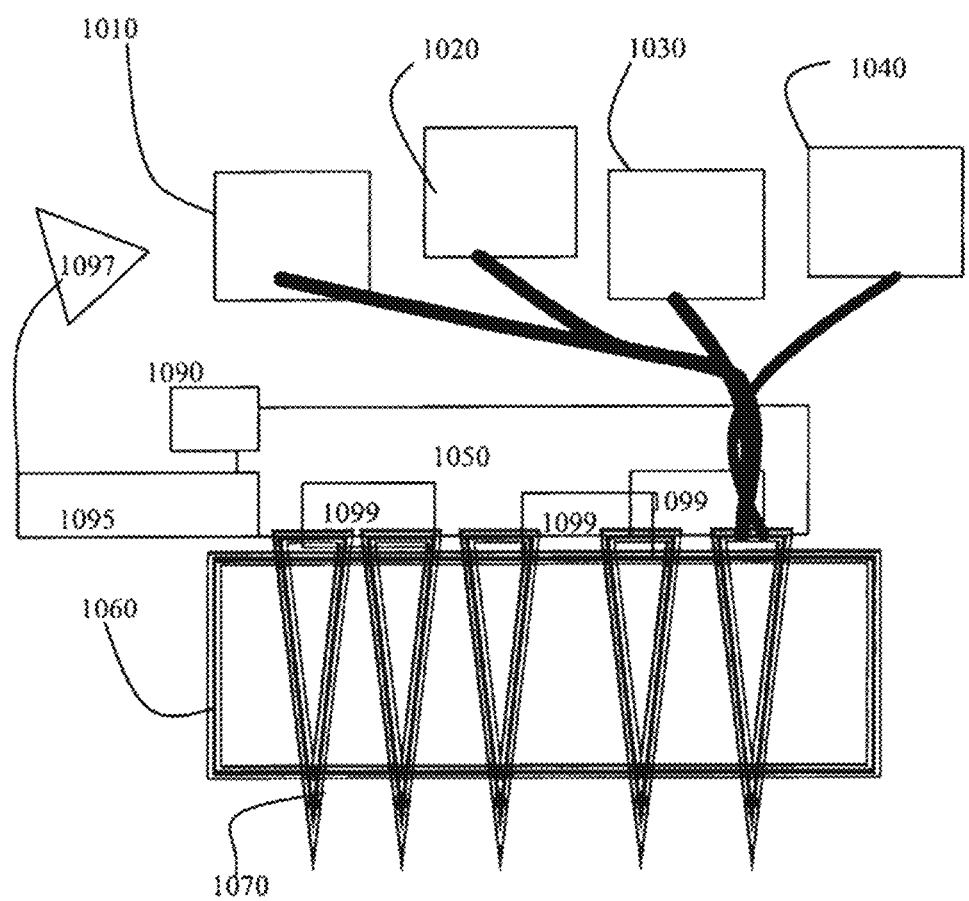
FIG. 10a illustrates a mechanical device for generation of a plurality of layers disruption pattern (PLDP) in a target material that is preferably in skin tissue.
Figure 10B:
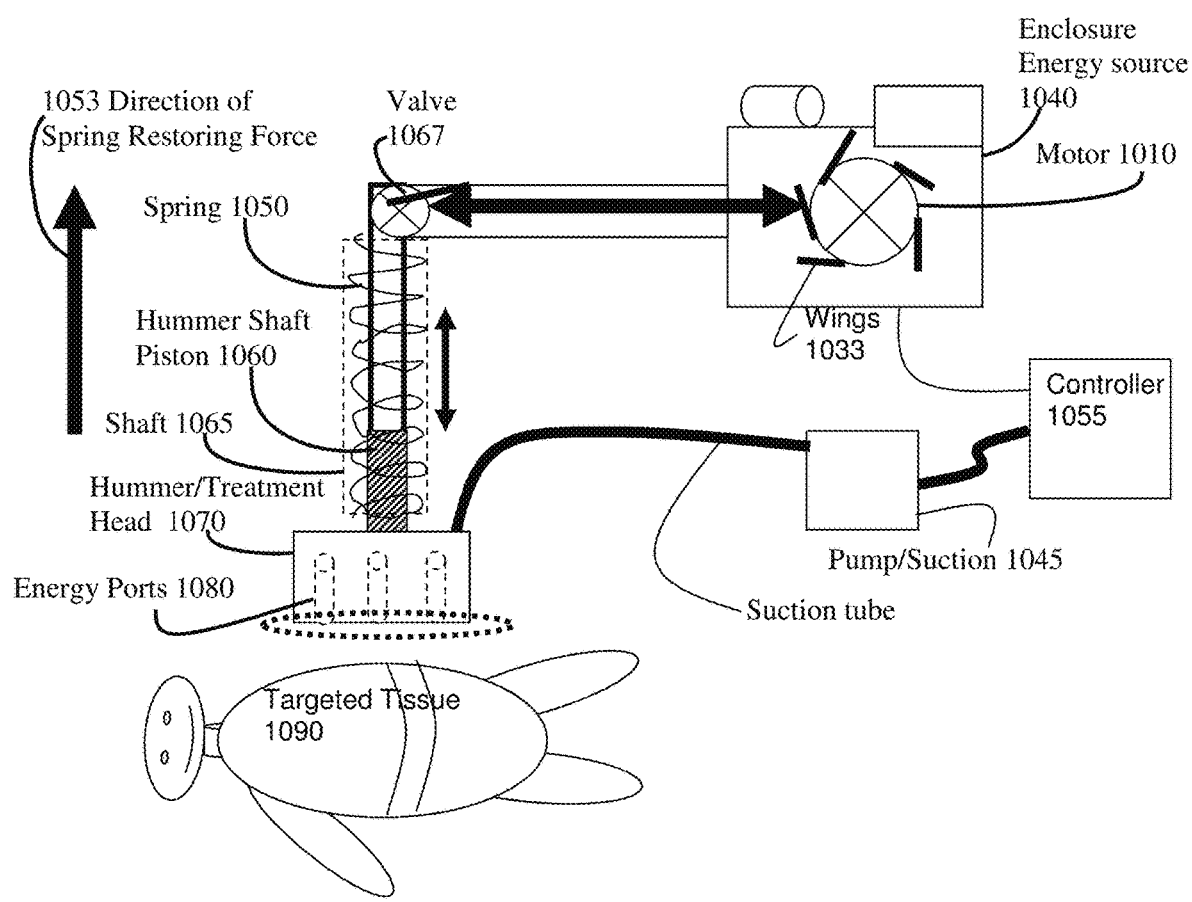
FIG. 10b shows an embodiment of a device for periodic pulsed Electromagnetic energy and periodic pulsed mechanical energy treatment of tissue.

FIG. 10*a* shows a mechanical device for generation of a plurality of layers disruption pattern (PLDP) in a target material preferably in skin tissue. Here, the device generally includes a member 1050 to which hollow members, 1070 (HM), for example, needles or syringes, 1070 are attached. The syringes are designed to be small so that their penetration into the target material and in particular into the skin tissue is easy and cause as little disruption as possible and as little collateral damage as possible.

Penetration of the hollow members is limited by a guard 1060 that can preferably be adjustable to limit the hollow member 1070 penetration to the depth of the epidermis, to above the melanin in the basal layer of the epidermis. The HM 1070 can be inserted into the target manually or in with a plurality of derivers 1075. Said drivers 1099 can be operationally couple to an imaging system, for example, ultrasounds, polarized light imager, OCT, or other imaging system, 1097. The imaging system 1097 can be operationally coupled to a controller 1095 that controls the drivers 1099, and drives the HM 1070 into the target material preferably into a target skin, and also control the adjustable guard 1060. The plurality of HM 1070 can be operationally couple to reservoir of air or gas or fluid, 1010 that can inject air or inert gas or fluid into the disruption in the target material for example to allow the creation of voids, that reflects light or enhance scattering.

An energy source 1020, for example a laser or a broad band flash lamp or an LED, can be coupled to said HM 1070 to inject light for destruction of melanocyte or pigmented target or vascular targets or fat. Alternatively, the HM 1070 can also be couple to a source or reservoir, 1030, of liquid that is beneficial to the skin, for example, lotion, or vitamin source, or drug or medicine, or a protective dye or liquid that absorb and or reflects incoming radiation (particularly UV and aging light from 100 nm to 450 nm, for example). Alternatively to inject light for destruction of melanocyte or pigmented target or vascular targets or fat. Alternatively, the HM 1070 can also be couple to a source or reservoir, 1040 that contain an esthetic cream or dye or color or other esthetic or appearance-enhancing agent.

Indications and Applications

Production of subsurface disruptions can be used in any one or more of the indications and applications listed below.

One use is to activate keratocytes, which is part of the healing process. For example, by directing an 80 MHz near-infrared beam with a nJ per pulse energy of femtosecond laser pulses at 800 nm, multi-photon absorption results in tissue modifications with no collateral damage to overlying or underlying tissue. Multi-photon imaging can then be used to guide the surgery and monitor the effect. Additionally, OCT and high resolution ultrasound can be used to monitor and guide the procedure. These modifications can be used in many locations in the body, including for example, modifying optical properties in cornea tissue for refractive surgery in the eye. Those skilled in the art will also appreciate from the teachings herein that subsurface disruptions can be used to increase collagen production.

Another use is to increase porosity of the target. Such increases in porosity can be very useful, for example, in using the skin to dispense insulin, birth controlling hormones, nutrients, vitamins, or other compositions to the blood stream.

Another use is to alter an apparent color of the skin. Natural skin pigmentation is associated with the presence of melanin, and the creation of surface or subsurface multilayer pattern in the human skin can either reduce the presence of melanin containing cells or cause narcosis in melanin containing cells so that they are eventually eliminated from the body. Additionally, creation of multilayered patterns on the surface of the skin or underneath the surface of the skin or other target, can interfere, block or otherwise alter the light scattered back from the skin. Such permanent or semi-permanent effects can modify or alter undesired colors of the skin or target and create alternative more desired colors of the skin. To that end, a specific multilayer pattern in and under the surface of the skin might reflect pink or white colors (for example, white-looking colors are created by increased reflection across an incident sunlight spectrum). Subsurface multilayer patterns can also be used to remove artificial dyes and artificial colors embedded in the skin, for example, by ablating vaporizing or breaking up tattoos dyes. Partial results could also be affected by simply blocking or modifying the reflected colors, or by generating alternative or compensating color in the skin, or reflected from the skin, by introducing a multilayer pattern above the embedded layers of dyes, pigments or colors.

Another use is to protect the skin from radiation, for example by modifying the refractive index of skin, such that transmission of electromagnetic radiation of wavelength below 400 nm is lowered by at least 20%. Protections can also be achieved for thermal energy or heat conduction; electricity, chemical substances; and microbes.

Another use is to reduce the appearance of wrinkles and lines, improving skin texture, rejuvenating the appearance of the skin, reducing skin pigmentation (either generally or in specific foci such as freckles, birthmarks, lentigos or tattoos), treating dyschromia, improving the appearance of scar tissue, treat acne, and treating vascular lesions such as port-wine stains, hemangiomas, telangiectasias, venous lakes, and spider and cherry angiomas. The range of dermatological conditions that can be treated according to the teachings herein includes virtually any type of dermatological defect in need of correction. Moreover, these effects can be readily accomplished by either (1) reducing the presence of vascular cells, veins or vascular structure by selective thermolysis, or by (2) micro ablation of vascular structures, sufficient to cause narcosis or elimination of such portion of the skin. Thermal effects can be produced in three dimensions underneath the skin to interrupt or destroy such vascular network. In one preferred embodiment, creation of multilayer pattern for overlaying the vascular lesion, can block or alter the reflection of incident light that incident on the skin. This method has a significant advantage as it does not involve the destruction of the vascular target themselves.

Another use is to introduce a composition into the skin, including for example a dermafiller, Botox™ toxin, tattoo dyes, medicine, nutrients, and vitamins.

Another use is to retard growth of a hair follicle. In that regard apparatus and methods are contemplated that include an imaging system, for example, an OCT, ultrasound, opto-acoustic methods, polarization microscopy, florescence microscopy or other imaging method for imaging the hair follicles and hair. Imaging elements can also be used to view skin modifications created in the region of the bulge and matrix of the hair follicle, and in the follicles' papillae, before during and after the energy are directed at these regions.

Another use is to reduce acne. Acne lesions result from the rupture of a sebaceous follicle, followed by inflammation and pus (a "whitehead"), or by accumulation of plugged material in the sebaceous follicle (a "blackhead"). This pathophysiology has two major requirements: (1) plugging of the upper portion of the follicle, and (2) an increase in sebum production. The upper portion of the follicle, i.e., the "pore" into which sebum is secreted and which is directly in communication with the skin surface, is called the infundibulum. A plug forms in the infundibulum from cells, sebum, bacteria, and other debris. The sebaceous gland continues to produce sebum (an oily fluid), stretching the infundibulum until either it or some lower portion of the follicles ruptures. Apparatus and methods described herein can be used to reduce sebum production, partial or complete reduction in the activity of the sebaceous gland, or the creation of increase porosity and drainage around the sebaceous gland and toward the skin so that the sebum and oil as well as bacteria and pus are drained from the skin.

Another use is to interfere with production of sweat, as in cases of sweaty palms and/or excessive sweating under the arm pit. Another use is to reduce the presence or size of fat cells in the target, especially fat cells in human or animal bodies.

Another use is to interfere with nerve function. This is particularly useful in applications such as reduction of skin sensitivity, reduction of pain, and, for example reducing and resolving unseemly nerve twitching, unwanted or uncontrollable motions, muscle movement, or twitching, in particular facial twitching, as well as resolution of or reduction of wrinkle and skin folds that are generated by muscle movement or muscle action. An example of such prior art treatment for the resolution of facial wrinkles is the use of Botox™ a toxin that is injected under the human facial skin to resolve or reduce the appearance of periorbital skin wrinkles or wrinkles around the lips or in and around the forehead, eyebrows and nose area, and other skin and facial wrinkles.

In one preferred embodiment, a multilayered pattern subsurface disruptions is created in the vicinity of a nerve in the dermis. Such a pattern can interfere with the function of the nerve ability to transmit sensation to the brain. Such modification to the skin and the nerve in the dermis, can allow permanent or temporary interfere with the function in the nerve allowing temporary or permanent reduction of pain or transmittance of unpleasant sensation from the skin to the brain. Alternatively and preferably, such a modifications of subsurface skin structure, if increasing porosity, will also allow the storage of ancillary substance capable of interfering with nerve function such as pain medication, numbing compounds, or toxin such as Botox™ that allow interference in skin function, relaxation or temporary or permanent and controllable paralysis of muscle function and a subsequence reduction in the appearance of wrinkles on the skin.

Another use is to relax and thus reduce the appearance of wrinkles. Here, an energy source, for example, an ultrashort pulsed laser, is focused onto the facial muscle. Muscle contraction and relaxation are described in many places. In brief, the process that occurs within a skeletal muscle, from excitation to contraction to relaxation is described as follows: (1) an electrical signal (action potential) travels down a nerve cell, causing it to release a chemical message (neurotransmitter) into a small gap between the nerve cell and muscle cell. This gap is called the synapse; (2) the neurotransmitter crosses the gap, binds to a protein (receptor) on the muscle-cell membrane and causes an action potential in the muscle cell; (3) the action potential rapidly spreads along the muscle cell and enters the cell through the T-tubule; (4) the action potential opens gates in the muscle's calcium store (sarcoplasmic reticulum); (5) calcium ions flow into the cytoplasm, which is where the actin and myosin filaments are located; (6) calcium ions bind to troponin-tropomyosin molecules located in the grooves of the actin filaments. Normally, the rod-like tropomyosin molecule covers the sites on actin where myosin can form cross-bridges; (7) upon binding calcium ions, troponin changes shape and slides tropomyosin out of the groove, exposing the actin-myosin binding sites; (8) myosin interacts with actin by cycling cross-bridges, as described previously. The muscle thereby creates force, and shortens; (9) after the action potential has passed, the calcium gates close, and calcium pumps located on the sarcoplasmic reticulum remove calcium from the cytoplasm; (10) as the calcium gets pumped back into the sarcoplasmic reticulum, calcium ions come off the troponin; (11) the troponin returns to its normal shape and allows tropomyosin to cover the actin-myosin binding sites on the actin filament; and (12) because no binding sites are available now, no cross-bridges can form, and the muscle relaxes.

Another use is to correct hyperopic eye sight, preferably using a high repletion rate ultrashort pulse oscillator, for example an oscillator running at 88 MHz.

Another use is to modify the index of refraction of component of the eye for correction of eye sight. In this application, a laser source 200, for example a Ti:Sapphire, oscillator, running at 88 MHz with a pulse energy of for example from about 0.01 nJ to about 100 microjoule, from about 0.1 nJ to about 100 nJ is focused underneath the surface of the eye surface to create modifications that results in sufficient refractive index changes to correct eye sight such as myopia, astigmatism, hyperopia or In this embodiment, the pulses are focused through a transparent medium of the eye to create thermal based refractive index changes without ablating, bubbles, photodisruption or any other mechanical damage or cutting.

Major advantages of the ultrashort pulse laser (USPL) tissue ablation method include: 1) efficient ablation due to small input of laser energy per ablated volume of tissue and the resulting decrease of energy density needed to ablate material; 2) minimal collateral mechanical damage due to the efficient ablation and the short duration of the stress impulse; 3) minimal collateral thermal damage due to a) the extremely short deposition time and, b) the fact that a large fraction of the deposited thermal and kinetic energy is carried away with the ablated tissue; 4) the ablation threshold and rate are only slightly dependent on tissue type and condition; 5) extreme precision in ablation depth is achievable because only a small amount of tissue is ablated per pulse and the number of pulses can be controlled by feedback mechanisms; 6) low acoustical (operating) noise level (as compared to the acoustical noise produced by the high speed dental drill or other laser systems); 7) minimized pain due to localization of energy deposition and damage; 8) ability to texture surface by controlled beam profile and rasterizing; 9) precise spatial control: the intensity-dependent, multi-photon process self-ensures that tissue below or laterally removed from the beam focus will not experience ablative interaction; and 10) since ultrashort pulses interact strongly with all matter regardless of specific linear absorption characteristics, efficient processing of almost all tissue types is possible.

Using these properties, a preferred embodiment contemplates a device and method for skin rejuvenation with minimal thermal damage, virtually no pain and very fast recovery. The device contemplates producing a controlled damage below the surface of the skin. For example a short pulse electromagnetic (EM) energy is aimed at the epidermis, dermis or the epidermal dermal junction regions so that the focus of the beam is in one of these regions. In yet another preferred embodiment the ultrashort pulse (USP) can be generated by ultrashort pulse lasers. This Ultrashort Pulses can be focused to a spot size ranging from about 1 μm to about 3 mm, from about 10 μm to about 200 μm. The pulse energy may range from about 0.01 micro joule to about to about 10 Joules, from 0.1 micro joule to about 10 mJ. The pulse rep rate (PRR) may range from about 0.01 Hz to about 80 MHz, from about 0.1 Hz to about 80 KHz. In many cases the preferred PRR will be between 10 Hz and 180 KHz. Spacing between each spot should allow uniform healing with desired aesthetic outcome and will range from about 10 μm between the beam spots to about 1 mm, from 30 μm to about 500 μm.

The beam thus focused can be scanned to produce a pattern below the surface. The pattern may consist of thermal damage at each spot or may consist of cavities and photo-disruption at each such spot. As the body recovers and heal it will remove unwanted debris and damage or ablation byproducts and produce a more elastic healthier younger looking skin. Because the damage is minimize and confined and occur vary rapidly pain is minimizes and healing is very rapid.

In yet another preferred embodiment, the ultrashort beam is focused on the surface itself and thus creates a controlled ablation and removal of the surface layers and cut deeper into the surface of the skin. Because ultrashort pulse generates very little thermal damage the cut is very precise and similar to that of a scalpel. Healing time is much faster. However, because the cut is done with small ultrafast pulses, thermal and mechanical stimulation of nerves is minimized Reduction of pain and faster healing time will then result.

The scanned beam can begin its work at a lower layer (deeper into the tissue) and then moved up to generate sequential "sheets" or layers of well-defined damage spots or a continuum (if the beam generated spots are very close to each other). The pattern generation can be made by moving from one location to a thermally and mechanically isolated second location and on to a third thermally and mechanically isolated location, so that thermal and mechanical damage is farther minimized.

Pattern can be made in different shapes or forms and different sequences by focusing the beam below the skin surface into dermis, epidermis or fat layer and/or by using self-focusing and filament effect to extent and manipulate the extent and shape of the damage. The pattern spacing is made to minimize pain and accelerate healing.

Conventionally, tanning by increasing production of melanin through the exposure to sunlight or to tanning lamps, or through the coloring or embedding in the skin of dyes, inks or paints. Here, however, tanning can be produced through modification of the reflected color from the skin by permanent or long term modification to the skin structure. This new form of tanning is obtained through structural changes of to the skin, for example subsurface microscopic modifications to the skin cells and or tissue that allow modifications of the reflected light so that a desirable color, or colors combination or tanned colors appears to the viewer.

This can be accomplished by applying high pulse repetition rate (PRR) laser either at the surface of the skin or below the surface of the skin to create reflective effects that will result in changes to skin coloring. This could also be accomplished by the high PRR pulses of electromagnetic energy either at the surface or below the surface of the skin. The essential steps are: (1) create the pattern of layered modifications or layered cavities; and (2) rub in lotion or dye or sunscreen or colors.

Many instruments can be used to generate the effect. For example: ultrashort pulse femtosecond (fs) lasers, long pulse lasers, continuous wave lasers (CW), needles or fakir spikes or needle arrays, and mechanical injectors. For example, using pulse light energy, in a preferred embodiment, a high pulse repetition rate lasers running at a pulse rep rate of from about 10 Hz to about 100 MHz, from about 1 KHz to about 100 MHz can be used, with sufficient power density. A preferred embodiment will use laser or light sources with pulse duration from about 1 microsecond to about 1 fs, from about 10 ns to about 3 fs, and more preferably from about 10 ps to about 10 fs. Pulse energy preferably should be from about 0.01 nJ to about 10 J and more preferably from about 0.1 nJ to about 1 J.

Preferred pattern of tissue modification should generated the following pattern in the tissue: Preferably, the spot size at the surface of from about 0.01 μm to about 100 mm, from about 10 μm to about 2 mm, along with a scanner or other elements that are capable of moving the beam along the targeted surface of bulk volume (for example, galvanometer scanners, spinning polygon, or vibrating lens, among other methods known in the art for scanning or stirring beams), so that the a pattern is created that rejects or reflect certain colors or wavelengths. For example, an destructive interference in the forward direction can be created to reject wavelength in the range of from about 170 nm to about 400 nm thus reducing the penetration of cancer-causing radiation in the UV. Alternatively a reflection of sunlight or room light in the wavelength that appears to the eye in the color of tanned skin can be useful aesthetically to enhance the perception of beauty and healthy-looking skin to the eye of the observer. Many other possibilities of reflected or transmitted colors can also be envisioned for protecting the skin or underlying tissue, for beauty or aesthetic reasons or for enhancing light and/or other forms of energy penetrating the skin for therapeutic or diagnostics or research purposes.

The number of layers that can be created can range from about N=1 to about N=150 and more preferably from about N=1 to about N=50 and most preferably from about N=2 to about N=10.

Utilizing the pattern of tissue modification described above, the following additional applications can be envisioned: devices and methods for (1) increased scattering; (2) increased storage; (3) increased elasticity; (4) fractional rejuvenation; (5) fractional tattoo removal; (6) fractional fat removal; (7) fractional pigmentation; (8) fractional vascular removal; (9) guided acne/sebaceous gland treatment; (10) guided hair removal in 3d; (11) treatment of nail diseases by 3D material processing; and (12) creation of a barrier so that no cell migration (in particularly cancer cell migration is possible from the basal and epidermal layers deeper into the dermis and into the human body.

In another preferred embodiment, a device and a method for treating subsurface or surface target with minimal collateral damage are contemplated. For example, in this embodiment, the system and method are designed to improve the look and condition of a skin, by utilizing a train of ultrashort pulses (below 10 ps in duration) said pulse energy is such that said energy is below the threshold level for tissue interaction. The beam is then manipulate, (for example, by decreasing spot size or increasing the pulses energy) so that when it encounters a target within the skin that has increased absorption compared to the surrounding skin water-dominated or low absorption cells, the power density at these absorbing target initiate photo-disruption or avalanche electron generation to modify or ablated the target.

Ultrashort pulses, as contemplated herein, can generate intense fields and heat at the desired subsurface location without damaging the surface or overlying skin. The targeted muscle however, will be disabled by the nonlinear localized field so that: (1) the electric signals are disrupted; (2) the cross-bridges formation is disrupted; (3) the chemical signals are disrupted; and (4) other targets of the radiation or ultrashort pulses are also possible. Such disruption can be temporary or permanent depending on the extent of the damage. One major advantage is that this disruption can be formed in patterns that allow some muscle activity to continue so that facial expression are still possible—a major drawback of the current Botox™ technology—while the appearance of wrinkles and fine lines is reduced. Another major advantage is that the disruption can be highly localized and much safer because it does not endanger deeper or collateral tissue or other body muscle or function and does not involves toxins.

These and other effects contemplated herein can last for significant periods of time—at least 12 hours, but more preferably at least 1, 2, 3, 5, or 10 days. In some cases the effects are contemplated to last at least 12 weeks.

It should also be appreciated that the concepts herein can be used to treat skin in any patient of any age or gender. They can also be used to treat animal skin or skin of plants fruits, vegetables, and seeds, and even single cells or small collections of cells (egg, sperm, embryos), or organelles. On the other hand, these concepts are contemplated to be particularly useful in the treatment of aged skin, skin of old human or animal, and, in particular skin that has been damaged or aged by exposure to light. Facial skin such as, for example, the perioral and periocular skin are likely to be very useful targets.

Methods for Dermatological Treatment.

The embodiments disclosed herein may treat a subsurface target using characteristics of short pulses. In one example, dermatological applications are applied, for example Hair Removal. In an embodiment, an energy source is configured so that its energy is focused in time and space onto a targeted volume under the surface of the targeted material. The interaction with the targeted volume is designed to allow modification or imaging of the targeted medium.

To achieve a desired effect on the targeted medium, a quantity of energy is directed towards the targeted volume of subsurface tissue. The quantity of energy is concentrated in time and space so that that it reaches an above threshold level of energy density. Energy density is defined as: (Energy density)=(quantity of energy)/(unit volume)/(unit time), i.e. the volumetric power density is defined as a quantity of energy per time per unit volume and per unit time. The Energy source preferably produced one or more of said energy types: Light energy; Electromagnetic (EM) Energy; Mechanical Energy; Sound Energy; Laser Energy; Chemical energy; Thermal energy; Nuclear energy; Ultrasound energy. In one preferred embodiment EM energy, for example, Laser or light energy, is produced by an ultrashort pulse laser source.

1. A package of such energy is caused to propagate from the energy source towards the targeted material. When said package of energy is compressed in time and space so that its volumetric power density is above the threshold of interaction with the targeted tissue to reach a desired effect, the effect will take place at about that region in space within the targeted tissue.

2. A uniqueness and novelty of the described method and device is the ability the ability to modify said EM energy utilizing the following parameters.

In one embodiment, A device for reducing the presence of hair on a skin, the device comprising: a treatment head coupled to a housing; an energy source coupled to a radiative energy source; a controller; and an output port; an imaging member in communications with said controller.

In further embodiment the energy source emit pulses of electromagnetic radiation; said pulses are shorter than about 1 ns. In further embodiment the energy source emit pulses of electromagnetic radiation; said pulses are shorter than about 0.1 ns. In further embodiment the energy source emit pulses of electromagnetic radiation; said pulses are shorter than about 10 ps. In further embodiment the emitted pulses are capable of modifying at least some subsurface structures. In further embodiment the emitted pulses are guided by said imaging system to modify at least one of: Hair root; Hair papilla, cell; Tumor cell; Infected cell; Infected tissue; Sebaceous gland; Sweat gland; Blood vessel; Pigmented tissue.

In further embodiment the device or method accomplish this substantially without damaging at least some of the tissue overlying it. The targeted tissue may be mechanically compressed to reduce electromagnetic radiation scattering. The targeted tissue may be deformed to reduce scattering of Electromagnetic radiation.

A device to modify skin against external influences, the device comprises a needle, a reservoir of substance, a member capable of delivering said substance through said needle to the skin, or a depth-limiting member, said member limiting the needle penetration to a predetermined depth.

In further embodiment the wherein said external influence is at least one of: Ultraviolent light; Electromagnetic radiation; Heat; Electric energy; Magnetic energy; Chemicals; Poisons; Bacteria' Mechanical impact; Viruses; Microbial infection.

In further embodiment the limiting member limit needle penetration to less than about 5 mm. In further embodiment the limiting member limit needle penetration to less than about 1 mm. In further embodiment the member limit needle penetration to less than about 0.5 mm. In further embodiment the limiting member limit needle penetration to less than about 0.1 mm. In further embodiment the limiting member limit needle penetration to less than about 50 micrometer.

For example, a beam spot size at the targeted volume, wherein said beam is: Larger than about 1 cm; Larger than about 5 mm; Larger than about 1 mm; Larger than about 0.5 mm; Larger than about 0.1 mm; Larger than about 50 micrometer; Larger than about 25 micrometer; Larger than about 10 micrometer; Larger than about 5 micrometer; Larger than about 1 micrometer; Larger than about 0.5 micrometer; Larger than about 0.2 micrometer; Larger than about 0.1 micrometer; Larger than about 50 nm; Larger than about 25 nm; Larger than about 10 nm; Larger than about 5 nm; Larger than about 1 nm. Or the Beam Spot size is Smaller than about 1 cm; Smaller than about 5 mm; Smaller than about 1 mm; Smaller than about 0.5 mm; Smaller than about 0.1 mm; Smaller than about 50 micrometer; Smaller than about 25 micrometer; Smaller than about 10 micrometer; Smaller than about 5 micrometer; Smaller than about 1 micrometer; Smaller than about 0.5 micrometer; Smaller than about 0.2 micrometer; Smaller than about 0.1 micrometer; Smaller than about 50 nm; Smaller than about 25 nm; Smaller than about 10 nm; Smaller than about 5 nm; or Smaller than about 1 nm;

Preferably the beam spot size is between about 1 um and about 100 um. More preferably the beam spot size is between about 1 um and about 20 um. Even more preferably the beam spot size is between about 1 um and about 5 um. Most preferably the beam spot size is between about 1 um and about 3 um. In a further embodiment, the beam spot size is between about 10 nm and about 1 um and more preferably between about 50 nm and about 500 nm.

Another embodiment contemplates a series of steps to achieve targeted modification of substances below the target material surface (for example below the surface of the skin or tissue). In the embodiments disclosed herein, the operator designs a spot size and pulse energy at the targeted volume (i.e. the operator design a volumetric power density=VPD) of As a non-limiting example, the inventor will now describe a method and a device for targeting hair bulb and reducing hair growth. The method is based on the idea that above threshold interaction can be achieved in the targeted zone, for example the region where the hair bulbs are located. There are two variations for the technique to damage the hair bulb (or hair roots, or hair matrix, or blood vessels feeding the hair bulb).

a) below or at threshold—the ultrashort pulse beam parameters are adjusted so it reaches near above threshold interaction at the vicinity of the hair bulb and rely on the hair bulb higher absorption (due to the present of melanin to reach the needed above-threshold distractive interaction level of energy density.

Imaging the region of the papilla and roots. The hair papilla and roots can be located with imaging devices such as Optical Coherent tomography (OCT) or ultrasound or other imaging methods, and the short pulses of energy are directed to the identified region where the bulbs or roots are located so that the power density is above interaction threshold in that region. The pulses of energy can be directed to that energy by manipulating beam parameters (e.g. spot size, pulse duration/temporal focusing, at the targeted location, wavelength, repetition rate) at the targeted volume are such so that the power density is above interaction threshold.

Detailed Embodiment of a. and b. Above

A. Below or at Threshold—

1. The operator set the energy source (for example, ultrashort pulse laser) parameters at or below threshold for interaction. One non-limiting exemplary method of doing this is to configure the directing optics or directing members so that the beam focus or beam minimum spot size, or beam most convergence point in space is Below the desired target region (for example, below the hair bulb) and the pulse energy density at the targeted region is lower than threshold for interaction.

Next, the operator manipulate the member directing and focusing the beam so that the location of the minimum beam spot is raised from below the targeted volume toward the targeted volume. In the process, the power density of the beam AT the targeted volume location is increased. At some point during this process, provided that the beam has sufficient volumetric power density to accede the interaction volumetric power density, the beam will damage the and/or irreversibly modify the targeted volume.

The method and device can rely on beam parameters such that even at the minimum spot locations within the targeted material, volumetric power densities (VPD) are ALWAYS below the interaction threshold VPD for the targeted material (e.g. dermis, epidermis, fat tissue, etc.) EXCEPT for targeted locations such as hair bulb and/or hair follicles (where, for example, the presence of melanin increase the beam energy absorption compared to beam energy absorption in the rest of the host material, for example, the dermis.

Subsequently, the operator decreases the beam spot size at the target by modifying the focal spot position (for example, by raising the focal spot position.

3. A tissue-modifying interaction then occurs when the spot gets small enough to increase the VPD at the targeted volume or targeted spot, to above interaction threshold. Some of the benefits of the above method are: No need for guidance, Lower cost of the device, Faster treatment, among others.

B. Guided Fs Interaction.

Figure 8C:
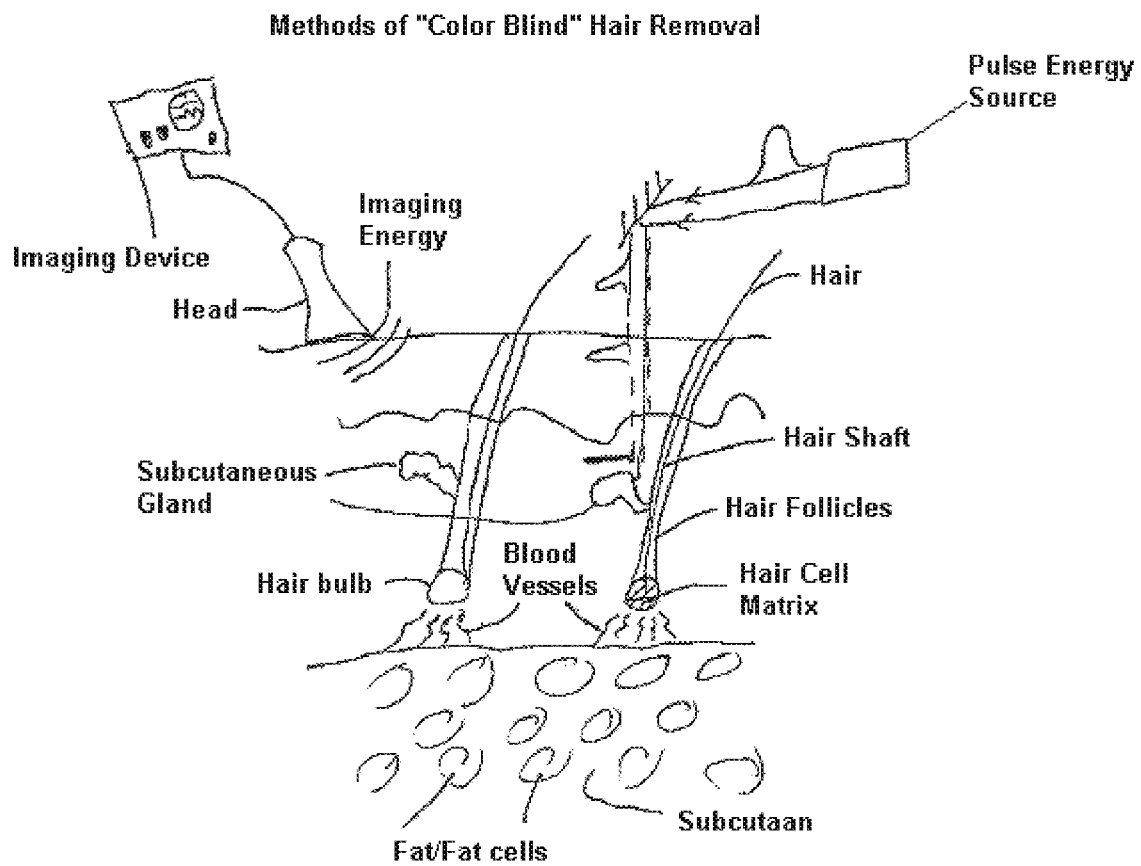
FIG. 8C shows further embodiment of a device and a method for treating subsurface targets, for example in hair follicles in the skin, with pulse compression and tissue compression.

Another embodiment contemplates a device and a method that is guided by an imaging device or method. This can be understood with the help of FIG. 8c (USHR1). An energy source R110 generating a pulse R112, at least one pulse modifier, 116 directing said pulse towards the target, said target is identified by an imaging device, 118. Said imaging device is in communication with said energy source. Said imaging device R118 can identify target location, and additionally or optionally can also identify a modification 119 caused by said interaction at a target location 120. The imaging member is in communication R125 with the energy source and the energy source and its controllers R127, and can provide feedback to the said energy source and said modifying member so that said interaction location can be moved in space to the desired location.

Figure 9B:
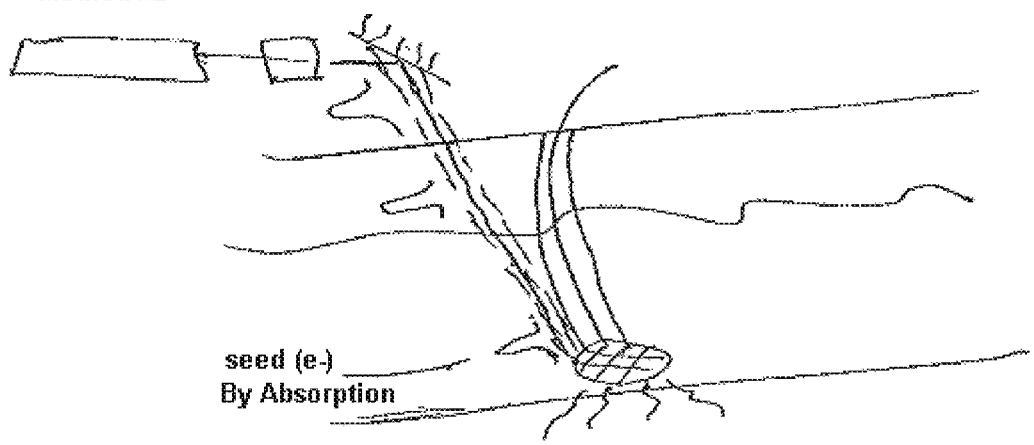
FIG. 9b shows further embodiment of a device and a method for treating subsurface target, for example in the skin, for example, hair follicle using two different methods of the embodiments disclosed herein.

FIG. 9b (USHR2) illustrates the removal of hair using guidance or imaging (B). FIG. 9b shows the hair structure, location in the skin, and phases. There are four phases in the life cycle of hair:

For example, The Hair Growth Cycle is divided into 4 Stages of Hair Growth: 1) Anagen Stage: This is the first phase of the hair growth cycle. It is also known as the active growth phase. In this phase of the hair growth cycle, your hair is growing continuously and consistently for 2-6 years. It begins in the papilla. The growth rate for your hair at this stage is about half an inch per month; however, do note that the span at which the hair remains during this stage of growth is dictated by the genes. Your hair at this point of time will look nourished and thick, and the longer your hair stays in this stage, the faster and longer it will grow. One thing to note is that permanent hair removal can only occur during this active growth phase.

2) Categen Stage: The second phase of the hair growth cycle is known as the Categen Stage. Also known as the transition phase, the follicle renews itself. Due to disintegration, the hair follicle shrinks and the papilla detaches from the follicle. The hair is then detached from the blood supply. Generally, the follicle will shrink to about ⅙ of its size, causing the hair shaft to be pushed upwards. About 2-3% of your hair will be in this phase, which lasts for 1-2 weeks.

3) Telogen Stage: Telogen Stage is the third phase of the hair growth cycle. Otherwise known as the resting phase, the hair follicle is dormant for 5-6 weeks. About 10-15% of the hair will be in this phase.

4) Return to Anagen Stage: This is the final phase of the hair growth cycle. In this state, hair loss occurs as the preceding hair strand gets pushed up and out by the new hair strand. The dermal papilla moves upward and meets the hair follicle once again, forming new hair in the process. The phase is then cycled back to the Anagen Stage".

Since modern light and laser based hair removal are based on melanin absorption in the papilla these known in the art methods do not work very well during the tologen phase and categen stage. In addition in, another severe problem of the present known in the art methods based on laser and light devices, is the fact that blonde, gray, white, red, and brown hair do not absorb the light or laser energy well. Thus the melanin in these types of hair is not very effective in capturing and transferring the light or laser energy to the papila and damaging the papila.

By contrast, the method of the embodiments disclosed herein circumvents this deficiency by delivering subsurface energy to the dermal papilla region through multiphoton absorption of the ultrashort pulses. The USP interaction is monitored through imaging members, (for example, Ultrasound, OCT, second harmonic, third harmonic, or other multi-harmonic, flourencse imaging methods or other methods, or other imaging method). The region of the hair bulb is located with imaging devices such as Optical Coherent tomography (OCT) or ultrasound or other imaging methods, and the short pulses of energy are directed to the identified region where the bulbs or roots are located so that the power density is above interaction threshold in that region. The pulses of energy can be directed to the desired region, for example, the hair dermal papilla, regardless of the phases of the hair growth. The energy pulses are directed by manipulating beam parameters (e.g. focal spot location, spot size, pulse duration/temporal focusing, at the targeted location, wavelength, repetition rate, as well as other beam parameters) so that the volumetric power density at the targeted volume, for example, papilla, are above the interaction threshold.

FIG. 15 shows an exemplary OCT imaging of hair follicles. The figure shows the ability of OCT imaging to locate the hair follicle, hair shaft, hair papilla, dermis, and sebaceous gland among other components of the skin.

Figure 14:

FIG. 14 shows an exemplary Ultrasound imaging of the hair follicle. Using an imaging method such as the exemplary OCT or the exemplary Ultrasound imaging, one can guide the interaction to ablate, coagulate, modify or otherwise change the target volume so that at least some of the hair papilla are damaged and the at least some hair growth is prevented or mitigated or reduced.

Some of the advantages in treating subsurface targets, for example, hair papilla, sebaceous gland, sweat gland or other subsurface targets, are:

a. Substantially reduced or even eliminated pain (for example, due to reduction in per pulse energy use and minimization of thermal energy deposition).

b. Substantially reduced or even eliminated collateral damage to tissue outside the targeted volume.

c. Rapid operation. The embodiments disclosed herein allow for the use of high and very high pulse repetition rates, for example, up to about 1000 Hz, up to about 10 KHz, up to about 100 KHz, up to about 1 MHz, and even up to about 10 MHz, up to about 100 MHz or even up to 1 GHz. A higher rep rate, for example up to a MHz can be generated with sufficient per pulse energy so that modification of the targeted volume which allow the intent of the treated to be achieved (for example, reduction of hair growth, or reduction in the number of sebaceous gland), can still be achieved even with the per pulse energy generating capabilities of a very high pulse rep rate systems described above (for example, ultrashort pulse Ti:Sapph laser at 800 nm and a microjoule of pulse energy, and a pulse rep rate of up to 350 KHz). The high Pulse rep rate, for example, up to about 300 KHz, up to about 1 MHz, up to 10 MHz, or even up to 100 MHz, will allow faster interaction, as photodisruption or material modification locations are rapidly being generated.

d. Multiple Treatments is possible with less trauma or injury in each treatment and in the overall duration of the sum of all treatments.

e. All tissue types and all hair colors can be treated.

f. A more complete and thorough treatment is possible with higher efficacy.

Tissue and Hair Modification Modes:

The embodiments disclosed herein contemplates tow methods for modifying the targeted Tissue (for example the hair roots and hair removal, or sebaceous gland, or sweat glands, or blood vessels, or other tissue targets).

One is through the photodisruption, ablation or other volumetric energy densities above the multi-photon (MP) ablation threshold.

The second is through three dimensional heating and the creation of heat due to accumulation of heat from a pulse train and through MP absorption of each pulse.

As a non-limiting example, we describe an embodiment for such three-dimensional heating comprising an ultrashort pulse source where pulse duration is capable of reaching volumetric Power Density (VPD) high enough for absorption once a threshold VPD is reached so that absorption within said tissue or target volume is reached. Pulses are then repeatedly heating the target and depending on the total amount of pulses heating the targeted volume per unit time, heat is accumulated and the temperature spatial and temporal distribution within the targeted volume rises.

An exemplary Ti:Saph or Er:Glass lasing medium, or other lasing media with broad band emission, can be used to generate short and ultrashort pulses known in the art (for example, pulse shorter than about a ns, or pulses shorter than about 100 ps, or pulses shorter than about 10 ps) so that said pulses can generate MP absorption at the targeted volume Such pulsed system, can have pulse repetition rate emitted at 1 GHz, 500 MHz, or 100 MHz, or 10 MHz or a MHz, or 500 KHz, or about a 100 KHz, or about 50 KHz or even lower than about 50 KHz.

More preferably such systems can have pulse repetition rate of emission of about 1 KHz to about 100 MHz, or even more preferably, a repetition rate of emission of about 10 KHz to about 50 MHz.

Principle of Operation: A Device to Remove Tattoos.

The device comprises of the following components: An pulsed energy source; Pulse duration of pulses is less than about 10 ps; Pulse Energy lower than 1 milli-joule per pulse; Pulse Energy lower than 100 microjoule per pulse; Energy lower than 0.01 mJ/pulse; Energy lower than 0.006 mJ per pulse. The energy source pulse repetition rate (Pulse Repetition Rate=PRR) of about 0.1 Hz or more; PRR of 1 Hz or more; PRR of 10 Hz or more; PRR of 100 Hz or more; PRR of KHz or more; PRR of about 10 KHz or more; PRR of about 30 KHz or more; PRR of about 50 KHz or more; PRR of about 100 KHz or more.

Improve Skin Look

A method for treating skin and improving the look of the skin comprising: the ultrashort pulse of energy (below 10 ps in duration) said pulse energy is such that said energy is below the threshold level to bring any water element absorbing said energy to above 100° C.

An embodiment for the method: below or at threshold; and raise Focus; No pain; No Collateral; Rapid; Multiple Tx; All Color; or More complete.

A device to remove tattoo comprises Pulses shorter than about 10 ps. The Pulse Energy: Energy lower than about 1 mJ per pulse; Energy lower than about 100 microjoule per pulse Energy lower than about 0.01 mJ/pulse; or Energy lower than about 0.006 mJ per pulse PULSE Repetition Rates:

Pulse Repetition Rate (PRR) of about 0.1 Hz or more; PRR of about 1 Hz or more; PRR of about 10 Hz or more; PRR of about 100 Hz or more; PRR of about KHz or more; PRR of about 10 KHz or more; PRR of about 30 KHz or more; PRR of about 50 KHz or more.

To create an interaction zone smaller than the diffraction limit and as small as a few nanometer. In fact, if absorbing elements such as (for example) nanoparticles are used to serve as initiators for the creation of Plasmon or otherwise initiate tissue or other material-modifying interaction, then interaction threshold substantially lower than the tissue or a material native threshold interaction can be reached and the volume of said tissue-modification or material-modification can be significantly lower than the native tissue or material volumes modified. For example such modified tissue or material volume can have diameters of a few nanometers.

EM energy will penetrate materials (or tissue) to varying degrees deepening on the type of materials the EM energy has to transverse on its way to the targeted volume. For example, if the targeted volume is covered with a metal layers, electrons in the metal will generate a shield field that will substantially exclude the radiation from the interior volume protected by the metal.

On the other hand, if the targeted volume is coated by a very thin dielectric layer, for example a thin layer of glass that is substantially non absorbing (for example a total reflection of about 8% to 10 percent of the incoming radiation) then most of the EM energy will arrive at the targeted volume.

In many cases of subsurface interaction (material modification, material imaging, or for diagnostic purposes) the tissue or material transmission, absorption, or scattering is dependent on the EM energy wavelength, power densities as a function of time and space as the EM energy propagates towards the target, and on the material that has to be transverse properties (e.g. the materials absorption, scattering, structure, and composition, as a function of time and space and at the wavelength and beam properties of the propagating EM energy).

In an embodiment, a package of energy is caused to be able to interact with targeted volume within a depth of from about 0 mm from the surface of the targeted material, for example, targeted mammalian body, to as deep as 10 cm below said targeted surface. Alternatively, in another embodiment, a package of energy is caused to be able to interact with targeted volume within a depth of from about 10 micrometer from the surface of the targeted material, for example, targeted mammalian body, to as deep as about 20 cm below said targeted surface. Alternatively, in another embodiment, a package of energy is caused to be able to interact with targeted volume within a depth of from about 10 micrometer from the surface of the targeted material, for example, targeted mammalian body, to as deep as about 15 cm below said targeted surface.

Alternatively, in another embodiment, a package of energy is caused to be able to interact with targeted volume within a depth of from about 10 micrometer from the surface of the targeted material, for example, targeted mammalian body, to as deep as about 10 cm below said targeted surface. Alternatively, in another embodiment, a package of energy is caused to be able to interact with targeted volume within a depth of from about 10 micrometer from the surface of the targeted material, for example, targeted mammalian body, to as deep as about 7 cm below said targeted surface. Alternatively, in another embodiment, a package of energy is caused to be able to interact with targeted volume within a depth of from about 10 micrometer from the surface of the targeted material, for example, targeted mammalian body, to as deep as about 5 cm below said targeted surface.

Alternatively, in another embodiment, a package of energy is caused to be able to interact with targeted volume within a depth of from about 10 micrometer from the surface of the targeted material, for example, targeted mammalian body, to as deep as about 2 cm below said targeted surface. Alternatively, in another embodiment, a package of energy is caused to be able to interact with targeted volume within a depth of from about 10 micrometer from the surface of the targeted material, for example, targeted mammalian body, to as deep as about 1.5 cm below said targeted surface. Alternatively, in another embodiment, a package of energy is caused to be able to interact with targeted volume within a depth of from about 10 micrometer from the surface of the targeted material, for example, targeted mammalian body, to as deep as about 7 mm below said targeted surface. Alternatively, in another embodiment, a package of energy is caused to be able to interact with targeted volume within a depth of from about 10 micrometer from the surface of the targeted material, for example, targeted mammalian body, to as deep as about 5 mm below said targeted surface.

Alternatively, in another embodiment, a package of energy is caused to be able to interact with targeted volume within a depth of from about 10 micrometer from the surface of the targeted material, for example, targeted mammalian body, to as deep as about 3 mm below said targeted surface. Alternatively, in another embodiment, a package of energy is caused to be able to interact with targeted volume within a depth of from about 10 micrometer from the surface of the targeted material, for example, targeted mammalian body, to as deep as about 2 mm below said targeted surface.

In an embodiment, several methods and devices enhance the energy penetration into the material or tissue and propagation towards the target material or tissue volume. For example, means for removing at least some of the liquid or fluid from the targeted tissue or material can be employed. Such means can be, for example, mechanical compression or chemical means for removing energy scattering-causing elements In yet another embodiment, the device and/or method include a member or means for reducing the volume of the targeted material or the volume of the targeted tissue. Such means can be, for example, mechanical compression of the targeted tissue or targeted material, or chemical means for removing scattering elements or scattering components or absorbing components in the tissue so that the light energy or EM energy or other type of energy can better penetrate the tissue or targeted material.

For example, means for removing at least some of the intervening material between the targeted tissue volume or material volume can be employed. Such means can be the Ultrashort pulse laser itself OR the EM energy quanta itself, that can be used to remove, or ablate, or vaporize, or "bore" or "tunnel" or "dig" a subsurface tunnel or voids in the space intervening between the subsurface targeted volume and the surface of the targeted material. I.e. such a method or a device can be used to Vacate, or evacuate, or empty, at least some of the material or tissue (and at least on a temporary basis, i.e. for a limited amount of time) so that at least some of the material is removed or compressed or altered, or modified so that the propagating energy experience less Scattering and/or less absorption as it propagate towards the scattered volume.

Figure 1B:
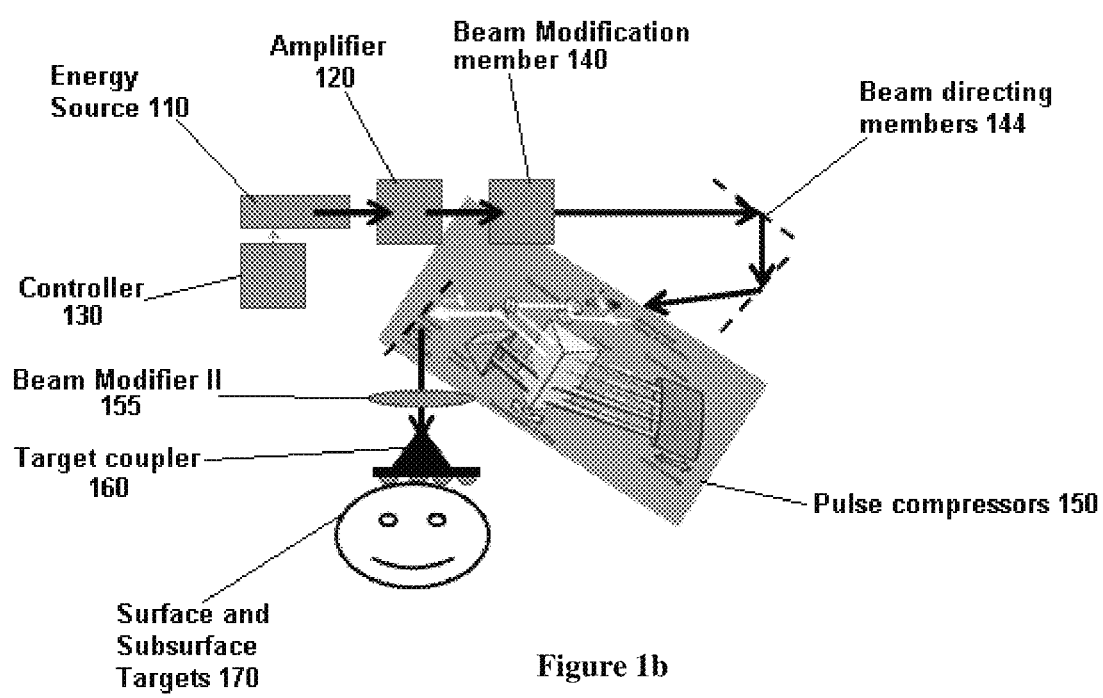
FIG. 1b Shows a device for treating subsurface target, for example in the brain, with pulse compression and tissue compression

For example the volume of the targeted material or volume of the targeted tissue or material can be employed. Such means can be, for example, mechanical compression or chemical means for removing energy scattering-causing elements Compression: Physical/Mechanical Compression, Optical Compression In an embodiment, an exemplary source of Ultrashort Pulsed EM energy generates a beam with sufficiently large spectral content, as shown in FIG. 1b. The energy source can be, for example, a short pulse oscillator 110, with an amplifier 120 and a beam modification member 140. The controller 130 controls the operation and manages input and output control signals including feedback, programming or automation. A beam modifier 140 may optionally include one or more member from the group including: lenses, mirrors, scanners, prisms, or diffraction grating and other diffractive optics elements. The beam modifier may also optionally include a pulse stretcher to stretch the pulse as is known in the art. Optionally, a pulse compressor 150 with members known in the art is used to recompress the pulse as it redirects its components towards the targeted material volume or tissue. A second beam modifier 155 spatially modifies and redirects the optical energy towards the beam coupler. Optionally A beam coupler 160 allows, for example, index matching, reduction of scattering, and enhancement of energy penetration into the targeted material or tissue.

As shown in FIG. 1b the pulse can be stretched when it comes out of the amplifier. It is the amplified and modified by the beam modifier 140. The energy pulse is then redirected by the directing member 144 and as it passes through a pulse compressor the pulse frequency components are manipulated so that the frequency components are rearranged in time and space so that at about the targeted location, said frequency component of the pulse create a minimum in the pulse duration. Since the pulse volumetric power density Pvm is equal to:

$$Pvm = Ep/(Va*Tpt) \quad (Eq. 1)$$

Where Ep is the energy of the pulse, Va is the volume of target material where the substantially the bulk of the Pulse energy is deposited, and Tpt is the Pulse Duration AT substantially at said absorbing targeted volume.

Since as is shown in equation 1, the Volumetric power density Pvm substantially around the targeted volume is Inversely proportional to the Pulse duration substantially around the targeted volume, Va, as Tpt become smaller, due to the compressing action of the pulses passing through the compressor 150, the Volumetric power density Pvm increases due to the shortening of Tpt and the compressing of the pulse.

As a result, if, for example, the threshold for targeted material modification is Pmmt, by compressing the pulse time duration around the targeted material, according to Eq. 1, the volume Va can become larger and material modification will still occur as the shortening of the pulse (which may also be referred to herein as temporal focusing, or pulse compression) compensate for, for example, the use of larger targeted volume, Vm, or larger spot size Am, or larger focal depth, Zm or both larger Am and Zm. (note that if, for example, the absorbing volume is a simple cube Vm is simply Vm=Am*Zm. If the absorbing volume has a more complicated shape or irregular shape then a more complex mathematical/geometrical expression will be used to describe it).

The point is that due to the fact that the pulse duration Tpt around the targeted volume can be compressed, a larger volume at the targeted material location can be used. Such allowed increase in pulse spatial extent as it travels through intervening medium and through the material, allow the avoidance of premature ablation or premature heating, or other premature material or tissue effects, for example, white light generation, self-focusing, thermal lensing or other nonlinear or intensity dependent effects.

These above mentioned effects can be avoided because less spatial focusing, or even substantially no spatial focusing, are used in delivering the energy pulses to the targeted region vicinity, and the operator or user, or the device, uses the Temporal focusing or pulse compression to bring the power energy density at about the region of the targeted volume to a power density level that is substantially above volumetric power density threshold for material or tissue modification. (again, said modification can be thermal, ablative, photo-disruptive, evaporative, explosive, acoustic, mechanical, chemical or other forms of tissue or material modification).

Note: whenever tissue as a target material is discussed, it is to be construed as ANY type of physical material to be modified. Such physical material may or may not be tissue and may or may not be organic. Similarly, whenever the inventor discusses material as a target material it is to be construed as ANY type of physical material and/or tissue to be modified. Such material may or may not be tissue and may or may not be organic.

An additional advantage is the ability of the method and device to employee a beam of a variety of spot sizes. For example, exemplary Parameters for the Beam Spot size: Wherein the beam spot size is Larger than about 1 cm but smaller than about 10 cm; Larger than about 5 mm but smaller than about 10 mm; Larger than about 1 mm but smaller than about 5 mm; Larger than about 0.5 mm but smaller than about 1 mm; More preferably yet, larger than about 0.2 mm but smaller than about 0.5 mm; More preferably, Larger than about 0.1 mm but smaller than about 0.2 mm; Preferably, Larger than about 50 micrometer but smaller than about 100 micrometer; Larger than about 25 micrometer but smaller than about 50 micrometer; Larger than about 10 micrometer but smaller than about 25 micrometer; Larger than about 5 micrometer but smaller than about 10 micrometer; Larger than about 1 micrometer but smaller than about 5 micrometer; Larger than about 0.5 micrometer but smaller than about 1 micrometer; Larger than about 0.2 micrometer but smaller than about 0.5 micrometer; Larger than about 0.1 micrometer but smaller than about 0.2 micrometer; Larger than about 50 nm but smaller than about 100 nm; Larger than about 25 nm smaller than about 50 nm; Larger than about 10 nm smaller than about 25 nm; Larger than about 5 nm smaller than about 10 nm; Larger than about 1 nm smaller than about 5 nm.

A broad beam may also be used with temporal pulse compression, wherein said broad beam with said pulse temporal compression allows deeper penetration, said deeper penetration is substantially more free of non-linear effects and substantially more free of self-focusing and white light generation. The improved working parameters with the above mentioned broader or wider beam allows improved work within: In the eye; In cornea treatment such as LASIK and removal of lens in treatment of cataract.

In the environment of the eye, it is often needed to treat targets that are deep within the eye ball, in the cornea, in the lens, in the sclera, in the retina, floating bodies in the liquid humor, or other targets. In such cases, high power density pulses (for example, for femtosecond or picosecond lasers) can create nonlinear effect in the eye as they travel towards the targeted area. For example, white light generation, thermal lensing, self-focusing or other nonlinear effects. The compression methods, devices, and methods described above allow the user or doctor, ophthalmologist, to avoid such treatment problems and reach targets deep inside the targeted regions of the eye ball or other targeted materials.

Replacement of Botox injection or in conjunction with Botox injection (for example, creating a subsurface storage space for Botox fluid injection so that said botox application is more evenly distributed and more evenly controlled. Also said Botox fluid release rate is more accurately controlled.

PPA—Principle of Operation: Treatment of Skull Ailments, Imaging and Diagnostic of Skull Ailments.

The embodiments disclosed herein describe a method and a device for enhancement of delivery of light into body for example, into the brain tissue. The method employs an ultrashort pulse laser capable of creating a subsurface interaction with tissue. The interaction is capable of removing at least some of the tissue below the surface of the skin to thin out layers within the volume of the bone.

Figure 2D:
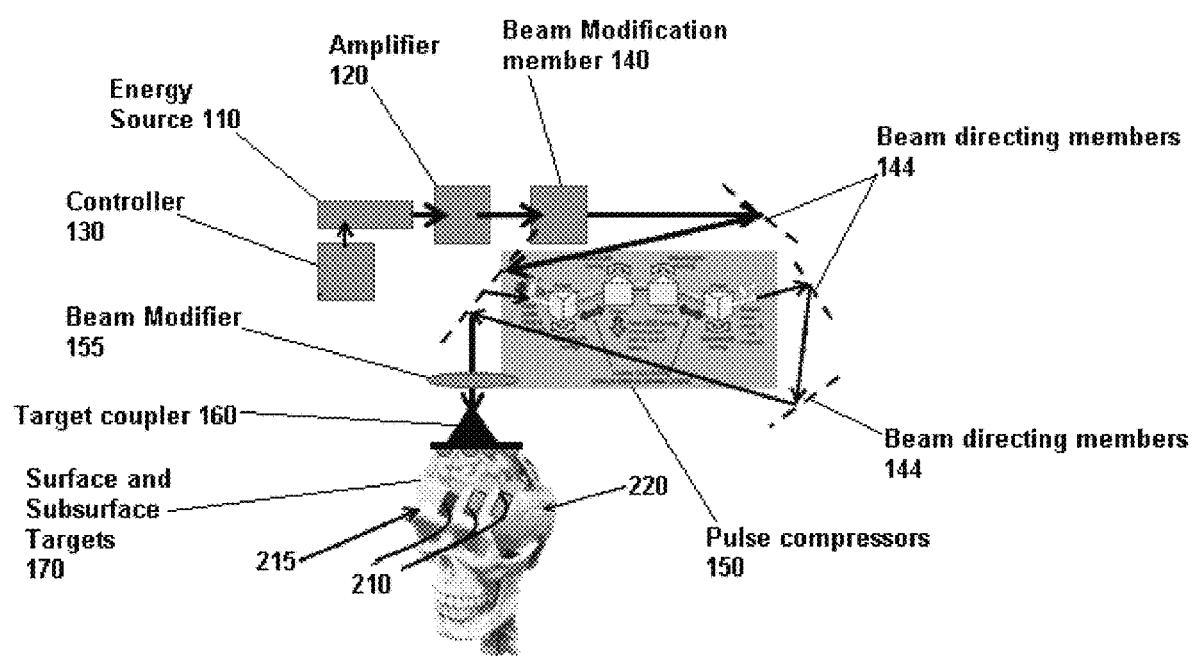
FIG. 2D shows further embodiment of a device and a method for treating subsurface target, for example in the brain, with pulse compression and tissue compression

For example, as shown in FIG. 2d, a volume 210 within the frontal bone of the skull, 215, is ablated or vaporized. Said volume is under the surface of the skull 220.

Figure 3B:
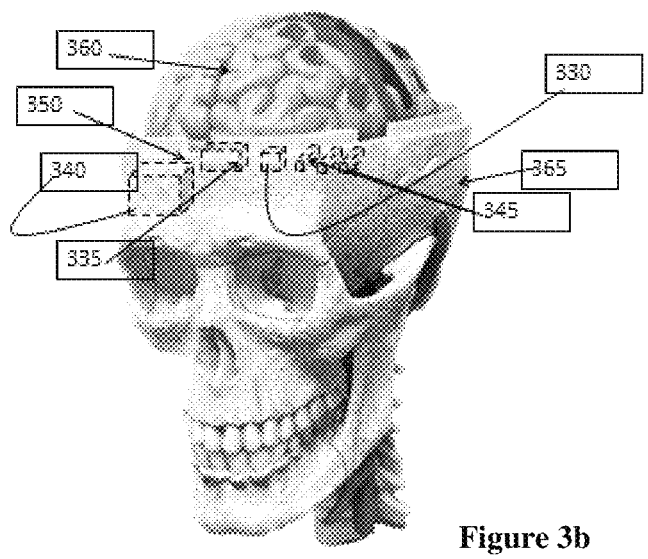
FIG. 3b shows further embodiment for targets of treatment in the skull and brain.

FIG. 3b shows another embodiment of the Skull with subsurface volumes or cavity creation wherein voids, cavities, or spaces of different shapes 330, 335, 340 and 345 are created under the surface of the skull or surface of the skin covering the skull 350, to facilitate penetration of light energy through the skull bone 365 to the brain 360.

In one embodiment the interaction modifies the skull bone sufficiently to enhance transmission by more than about 5%. In one embodiment the interaction modifies the skull bone sufficiently to enhance transmission by more than about 10%. In one embodiment the interaction modifies the skull bone sufficiently to enhance transmission by more than about 15%. In one embodiment the interaction modifies the skull bone sufficiently to enhance transmission by more than about 20%. In one embodiment the interaction modifies the skull bone sufficiently to enhance transmission by more than about 25%. In one embodiment the interaction modifies the skull bone sufficiently to enhance transmission by more than about 30%. In one embodiment the interaction modifies the skull bone sufficiently to enhance transmission by more than about 35%. In one embodiment the interaction modifies the skull bone sufficiently to enhance transmission by more than about 40%. In one embodiment the interaction modifies the skull bone sufficiently to enhance transmission by more than about 45%. In one embodiment the interaction modifies the skull bone sufficiently to enhance transmission by more than about 50%. In one embodiment the interaction modifies the skull bone sufficiently to enhance transmission by more than about 55%. In one embodiment the interaction modifies the skull bone sufficiently to enhance transmission by more than about 60%. In one embodiment the interaction modifies the skull bone sufficiently to enhance transmission by more than about 65%. In one embodiment the interaction modifies the skull bone sufficiently to enhance transmission by more than about 70%. In one embodiment the interaction modifies the skull bone sufficiently to enhance transmission by more than about 75%. In one embodiment the interaction modifies the skull bone sufficiently to enhance transmission by more than about 80%. In one embodiment the interaction modifies the skull bone sufficiently to enhance transmission by more than about 85%. In one embodiment the interaction modifies the skull bone sufficiently to enhance transmission by more than about 90%. In one embodiment the interaction modifies the skull bone sufficiently to enhance transmission by more than about 95%.

In another embodiment a device comprises an energy source, means for directing said energy to a targeted volume under the surface of the human body (for example the skull). Means for spatially and/or temporally concentrating the energy at a targeted volume under the surface of the body so that said concentrated energy is capable of changing the optical property of said targeted volume of tissue. The energy source is an ultrashort pulse laser. The pulse is spatially focused under the surface of the targeted tissue. The pulse is temporally focused under the surface of said targeted tissue. The pulse is both spatially and temporally focused under the surface of said targeted tissue.

The embodiments disclosed herein can be further understood with the help of FIG. 3b and FIG. 4b. FIG. 4b, shown an anatomical representation of the brain and its components and FIG. 4b shows the skull. The frontal lobe 410 is shown in FIG. 4b. The Frontal Lobe of the cerebrum contains the motor cortex and is associated with muscle movement and parts of speech. There are three possible ways to define the prefrontal cortex: as the granular frontal cortex, as the projection zone of the mediodorsal nucleus of the thalamus, as that part of the frontal cortex whose electrical stimulation does not evoke movements. The prefrontal cortex (PFC) is the anterior part of the frontal lobes of the brain, lying in front of the motor and premotor areas. This brain region has been implicated in planning complex cognitive behaviors, personality expression, decision making and moderating correct social behavior. The basic activity of this brain region is considered to be orchestration of thoughts and actions in accordance with internal goals.

The most typical psychological term for functions carried out by the prefrontal cortex area is executive function. Executive function relates to abilities to differentiate among conflicting thoughts, determine good and bad, better and best, same and different, future consequences of current activities, working toward a defined goal, prediction of outcomes, expectation based on actions, and social "control" (the ability to suppress urges that, if not suppressed, could lead to socially-unacceptable outcomes). There is an integral link between a person's personality and the functions of the prefrontal cortex.

In an embodiment, a device and a method is directed towards delivering a package of energy with sufficient power density (Again, Power Density is defined herein as a quanta of power per unit volume, or energy quanta per unit volume per unit time) to allow activation or modulation, or modification of brain activity. The challenge to achieve this goal has been the presence of overlying tissue such as hair, skin, muscle, bone, blood, fluids and liquids, or overlying brain tissue.

The method and devices overcome these challenges by utilizing one or more of the following principles of operation: 1) High power density pulses, for example, pulses from an ultrashort pulse lasers such as Ti:Sapph femtosecond lasers. 2) Selection of laser parameters, for example, wavelengths that minimize energy absorption by the overlying tissue. 3) Tissue compression, for example, protruding guards or suction power that compress the tissue, drive out fluids and liquids, and compress tissue components into a more dense form while optionally minimize optical index mismatching at boundaries. 4) Energy pulse temporal and spatial compression. For example through the use of optical elements such as lenses, prisms, diffraction gratings, mirrors, reflection gratings, etc. for example, through the use of optical focusing, or, for example, through the use of temporal pulse compression so that the pulse duration shrink as it propagates towards the targeted volume.

In a further embodiment, as shown in FIG. 3b, additionally or optionally, the brain or tissue modifying energy can be introduced through thinner portion of the skull bones, for example, under the roof of the eye, or through the temporal bone.

Additionally or optionally, in a further embodiment, as shown in FIG. 3b, the energy can be introduced through subsurface "ports" in the skull bone and tissue. Here, for example, through the use of the embodiment described elsewhere herein, of the ability to deliver temporally and spatially focused pulses of energy such that said spatially and/or temporally focused pulses are able to ablate or photo-disrupt or otherwise, remove at least part of the tissue or bone in the skull underneath the surface of the tissue. In such a manner, the embodiments disclosed herein proposes removing at least some of the tissue filling the skull and creating subsurface voids that allow enhanced energy penetration into the skull interior and interaction with said brain tissue.

The advantages of such subsurface "ports" is that while enhancing the penetration of energy or light, or for that matter even medication or nutrient or other desired chemicals, substances, or energy forms, into the interior of the skull, the integrity of the surface of the of the skull, and overlying skin, tissue and bone, is maintained, as well as the integrity of a barrier layer that is left posterior (i.e. toward the "voids" or cavities, 330 that are closer to the inner part of the skull between the Brain soft tissue (e.g. white and grey matter) and the "voids" or cavities or "subsurface windows" (SSW) 330.

Additionally or optionally, the voids, or cavities, or conduits, 330, thus "drilled" or ablated or vaporized, subsurface to allow enhanced optical energy or other form of energy, or substance or chemical, delivery into the brain or into the interior of the skull, can ALSO be filled with low absorption fluid, or liquids, that stabilize and maintain at least some beneficial properties of the skull yet allow enhanced deliver of external energy or substances or products. For example, such "filler" substances, 340, can for example, comprise a clear or low absorption Gels with at least some chemical or substances that retard, or discourage bone growth, for example said fillers, 340 discourage tissue or bone growth.

Additionally or optionally, the voids, or cavities, or conduits, 330, thus "drilled" or ablated or vaporized, subsurface to allow enhanced optical energy or other form of energy, or substance or chemical, delivery into the brain or into the interior of the skull, can ALSO be filled with low absorption fluid, or liquids, that prevents or slow down refilling or changes of the voids or cavities or conduits 330.

The creation of such Subsurface voids or subsurface windows (SSW) 330 can be made with the lasers parameters and pulse temporal focusing or pulse compression techniques described above and in related application. The SSW can be, for example, less than about: Less than about 1 micrometer in diameter; Less than about 5 micrometer in diameter; Less than about 5 micrometer in diameter; Less than about 19 micrometer in diameter; Less than about 15 micrometer in diameter; Less than about 25 micrometer in diameter; Less than about 35 micrometer in diameter; Less than about 50 micrometer in diameter; Less than about 75 micrometer in diameter; Less than about 100 micrometer in diameter; Less than about 125 micrometer in diameter; Less than about 150 micrometer in diameter; Less than about 175 micrometer in diameter; Less than about 200 micrometer in diameter; Less than about 250 micrometer in diameter; Less than about 350 micrometer in diameter; Less than about 500 micrometer in diameter; Less than about 750 micrometer in diameter; Less than about 1000 micrometer in diameter; Less than about 1250 micrometer in diameter; Less than about 1500 micrometer in diameter; Less than about 2 mm in diameter; Less than about 4 mm in diameter; Less than about 5 mm in diameter; Less than about 7.5 mm in diameter; Less than about 10 mm in diameter; Less than about 12 mm in diameter; Less than about 15 mm in diameter; Less than about 17.5 mm in diameter; Less than about 20 mm in diameter; Less than about 25 mm in diameter; Less than about 30 mm in diameter; Less than about 40 mm in diameter; Less than about 50 mm in diameter; Less than about 55 mm in diameter; Less than about 60 mm in diameter; Less than about 75 mm in diameter; Less than about 100 mm in diameter; Less than about 125 mm in diameter; Less than about 150 mm in diameter; Less than about 200 mm in diameter.

The subsurface window can be created, for example, with their anterior surface (i.e. the surface facing the outside of the skull and the external surface of the skin covering the body of the treatment subject, extending from about 1 micrometer below the surface of the skin; from about 5 micrometer below the surface of the skin; from about 7.5 micrometer below the surface of the skin; from about 10 micrometer below the surface of the skin; from about 15 micrometer below the surface of the skin; from about 20 micrometer below the surface of the skin; from about 25 micrometer below the surface of the skin; from about 37 micrometer below the surface of the skin; from about 50 micrometer below the surface of the skin; from about 75 micrometer below the surface of the skin; from about 100 micrometer below the surface of the skin; from about 150 micrometer below the surface of the skin; from about 200 micrometer below the surface of the skin; from about 250 micrometer below the surface of the skin; from about 350 micrometer below the surface of the skin; from about 400 micrometer below the surface of the skin; from about 500 micrometer below the surface of the skin; from about 600 micrometer below the surface of the skin; from about 750 micrometer below the surface of the skin; from about 1000 micrometer below the surface of the skin; from about 1500 micrometer below the surface of the skin; from about 2000 micrometer below the surface of the skin; from about 3000 micrometer below the surface of the skin; from about 4000 micrometer below the surface of the skin; from about 5000 micrometer below the surface of the skin; from about 7500 micrometer below the surface of the skin; from about 10,000 micrometer below the surface of the skin; More than about 10 mm below the surface of the skin but less than about 30 mm below the surface of the skin.

The height of the SSW (i.e. the extent of the SSW in the dimension directed from the surface of the skin towards the surface of the brain, i.e. towards the position of the targeted volume, or volume targeted for treatment within the skull), can range from about: about 1 micrometer; about 5 micrometer; about 7.5 micrometer; about 10 micrometer; about 15 micrometer; about 20 micrometer; about 25 micrometer; about 37 micrometer; about 50 micrometer; about 75 micrometer; about 100 micrometer; about 150 micrometer; about 200 micrometer; about 250 micrometer; about 350 micrometer; about 400 micrometer; about 500 micrometer; about 600 micrometer; about 750 micrometer; about 1000 micrometer; about 1.5 mm; about 2 mm; about 3 mm; about 4 mm; about 5 mm; about 6 mm; about 7 mm; about 8 mm; about 9 mm; about 1 cm; about 1.5 cm; about 2 cm; about 2.5 cm; about 3 cm; about 4 cm; about 5 cm; about 6 cm; about 7 cm; about 8 cm; about 9 cm; about 10 cm; more than about 10 cm but less than about 20 cm.

"About" means the value (e.g. 1 cm) plus or minus 50% of that value (e.g. if the value is, for example, 1 cm then "about" would mean any value between about 0.5 cm and about 1.5 cm.

The SSW can be made by debulking, vaporizing or otherwise substantially removing most of the material within about the volumes described herein above. OR, additionally and optionally, said SSW 330 can be made by creating a pattern of removed voids or cavities, or smaller conduits 340 within the overall SSW 330. Such pattern of voids 340 within the larger SSW 330 can optionally form a density of (expressed as percent voids 340 volume within the overall SSW volume 330) of about: About 1%; About 2.5%; About 5%; About 7.5%; About 10%; About 15%; About 20%; About 25%; About 35%; About 40%; About 50%; About 60%; About 70%; About 75%; About 80%; About 90%; About 95%; About 98%; About 99%; About 100%.

Principle of Operation: Correcting Vision in the Eye and Treatment of Eye Ailments:

Another embodiment is shown in FIG. 5b and FIG. 6b. In this embodiment the system and method to modify vision is contemplated. It has been described in the past by the present inventor as well as other prior art, it is known to cut flaps or subsurface lines within the cornea. The embodiments disclosed herein contemplate creating subsurface structures as described by the parameters tables shown in table 1a to table 1e, in the cornea or lens, or both in the cornea and Lens. Optionally, or additionally such structures can also be cut in sclera or other structures of the eye. The embodiments disclosed herein contemplates using such structures to modify the elastic properties or the optical properties or at least one of a group of properties of the eye using such structures 520. Among the group of such properties of the eyes are: Elastic properties, Optical properties, Refractive properties, Thermal properties, Hardness, Opacity, Absorption, Scattering, Electrical properties, Other properties.

Additional Embodiment for Ophthalmic Applications:

Additionally or optionally, a fluid or liquid is injected to the structures thus created within the Lens or the cornea, or other structures within the eyes. Such fluid or liquid may be injected or otherwise inserted into the eye and its volume, pressure, or density, or other relevant characteristic may be adjusted to allow control (possibly even dynamic, real time, adjustable control) of the curvature of the cornea or lens or other components of the eye, to allow treatment of refractive power of the eye, focusing power of the eye, and/or corrections of such ophthalmic conditions as myopia, presbyopia, astigmatism, cataract, or other ophthalmic conditions.

In another embodiment the energy source, for example an fs laser, creates the storage for a fluid or a liquid. The Fluid or liquid can, for example, be a memory retaining polymer. A Fluid containing absorbers for enhanced absorption of the incoming energy, or fluid which is doped with absorbers, for example nanoparticles that can expend upon the delivery of a willfully triggered external signal, for example a laser signal that cause them to expand. Depending on the position of said fluid pockets, they can either inflate or deflate the lens. For example the crystalline lens of the eye, thus causing increase or decrease in the focusing power of said lens. For example, an activation of the absorbers in pocket 620 can cause a lens to inflate and focus more. Thus the method and a device allows us to overcome and correct presbyopia. This is illustrated further with the help of FIG. 6b.

One can create micro structure in accordance with the cavities or voids dimensions specified by the embodiments disclosed herein. The embodiments disclosed herein contemplates inserting fluids, for example, doped with nanoparticles that respond to external energy and expends and perverse their shape or cool off and retract or expend in one part of the cornea to stretch, and expend in another part to contract. While inactivation of 620, can be achieved, for example, by activation of the absorbers 610, thus causing deflation of the lens and pocket 620 allowing flattening of the lens ("flattening" means making the lens flatter in appearance or in curvature, i.e. more oval and flat instead of the lens being more round and more curved). Lowering of the lenses focusing power, and, for example, treatment of myopia. So in effect, one trigger—620 causes expansion and bulging. The second trigger(s) 610 cause flattening including flattening (or turning off} of the first trigger. The two triggers work like two sets of springs with on and off switch wherein the energy is provided externally by the external energy source (e.g. laser light beam etc.)

One of the embodiments and principles of operation thus comprises (as shown in FIG. 6b): 1) The Creation of a storage space 620 and 610 (among other storage volumes in different locations and with desired structures). Such storage space can be created with the aid of an external energy source, for example, an external fs laser or USPL and its ability to create subsurface structures in the eye (or in other tissue or body parts, or other materials and substances). 2) The insertion (for example, injection) of a fluid or liquid capable of modifying at least one property of the eye (or other tissue or body part). For example, the injection of substance that can be willfully triggered by a signal from an operator so they expand. For example, a biocompatible fluid or liquid or other substance that can expend upon heating, wherein such biocompatible substance also contains a substance that can absorb a radiation from an external laser (for example, a biocompatible substance containing nanoparticles that converts said external energy into heat), and thus expending and causing the tissue (for example a lens or a cornea) to change it shape. 3) Activation of said inserted substance by an external source, and obtaining a desired shape (and possibly function) of the treated organ. For example, insertion of nanoparticles doped polymers into pockets or voids prepared by an external energy source such as a laser, or ultrashort pulse laser, can allow the user or operator to change the shape of a lens or cornea to improve vision. 4) Such changes to tissue or organs (for example, the eye crystalline lens) can be reversible and/or adjustable as the external source can be willfully used as described herein above to modify or adjust the changes.

Principle of Operation: Bacteria with Florescence or Absorption Filters:

In another embodiment, a method and a device for detection of bacteria is described. The device comprises a light source with a spectra emission that covers at least some of the excitation wavelength that causes the targeted bacteria to fluoresce. The Energy source can be for example, a broad band flash lamp, even a compact broad band flash lamp with a filter that allow light different from the emission wavelength of the bacteria to be emitted. The excitation energy source can, for example be similar to the one made with an disposable camera flash lamp and its related circuitry wherein a filter is used to limit the emission from the flash lamp to wavelengths shorter than the one emitted by the bacteria.

The bacterial emission is allowed to pass through a band-pass optical filter that blocks any other stray light. If a bacterial is present, the emission wavelength from the fluorescence bacteria passes to detector, for example a photodiode, and the signal detected then indicate the presence of the bacteria or other pathogen or virus, and can also be correlated to the amount of bacteria or pathogen present.

To avoid errors and increase accuracy, since if bacteria generate an emission following an excitation, the emissions of Wavelength (WL) no. 1, e.g. WL1 and WL2 have certain proportions or ratio, that is typical to those bacteria. Thus, knowing the ratio will confirm the type of bacteria and will ensure that the WL line that appear is not a stray light effect.

Thus, if the bacteria has TWO emission fluorescence wavelengths, then part of the emitted light can be direct to a band-pass filter that allow only WL 1 to be transmitted and a second part is directed to second line filter that allow only the second WL, WL2 to be transferred. Thus ONLY if both WL1 and WL 2 are present the device confirms that a bacteria of the type that emits both WL1 and WL 2, is actually present, and not an error that happened to have generated one of the WL by an error.

Figure 7B:
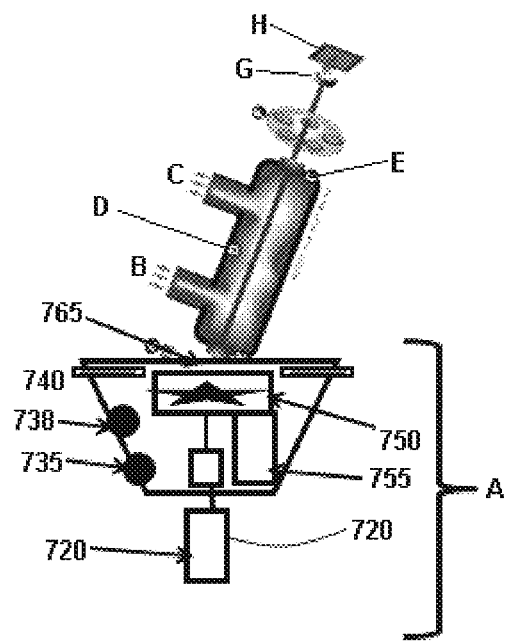
FIG. 7b shows an embodiment to detect bacteria or chemical components.

A device for detection and treatment of bacteria is shown in FIG. 7b. An exemplary device for detection and treatment of bacterial may comprise: A—an excitation source (A). Said excitation source comprises of the following members: 720 power source (e.g. AAA batteries), 725 capacitors, 730 trigger, 735 charge button, 755 control board microprocessor, 750 lamp/flash lamp (Usually broad band from about 300 nm or 400 nm to as much as 1.2 microns in wavelength. For Fluorescence excitation we can filter out the IR and Visible and allow mostly blue to UV excitation—e.g. see example below). 765 is a window; B—breath or bacteria input; C—Breath or blow outlet; D—Sample Chamber; E—Lenses; G—Filters/band path filters; H—Microprocessors.

Example of Bacterial Detection:

One can achieve rapid detection and differentiation of bacteria, e.g. *Escherichia coli*, *Salmonella*, and *Campylobacter*, which are the most commonly identified commensal and pathogenic bacteria in foods, using fluorescence spectroscopy and multivariate analysis. A most common and urgent need is the identification, detection and destruction of bacteria such as the strep bacteria in human infection, or bacteria causing bad breath. Fluorescence spectra can be collected over a range of 200-700 nm with 0.5 nm intervals flash lamp Fluorescence detectors as described herein above.

Once an optimum excitation and emission wavelengths for individual bacteria are identified, the excitation spectra can be generated for example one that shows maximum excitation values at 225 nm and 280 nm and one maximum emission spectra at 335-345 nm. Refinement with Two wavelength emission and multi wavelength excitation as described above can be employed.

3. Needle Sunscreen and Subsurface Interaction.

Figure 11A:
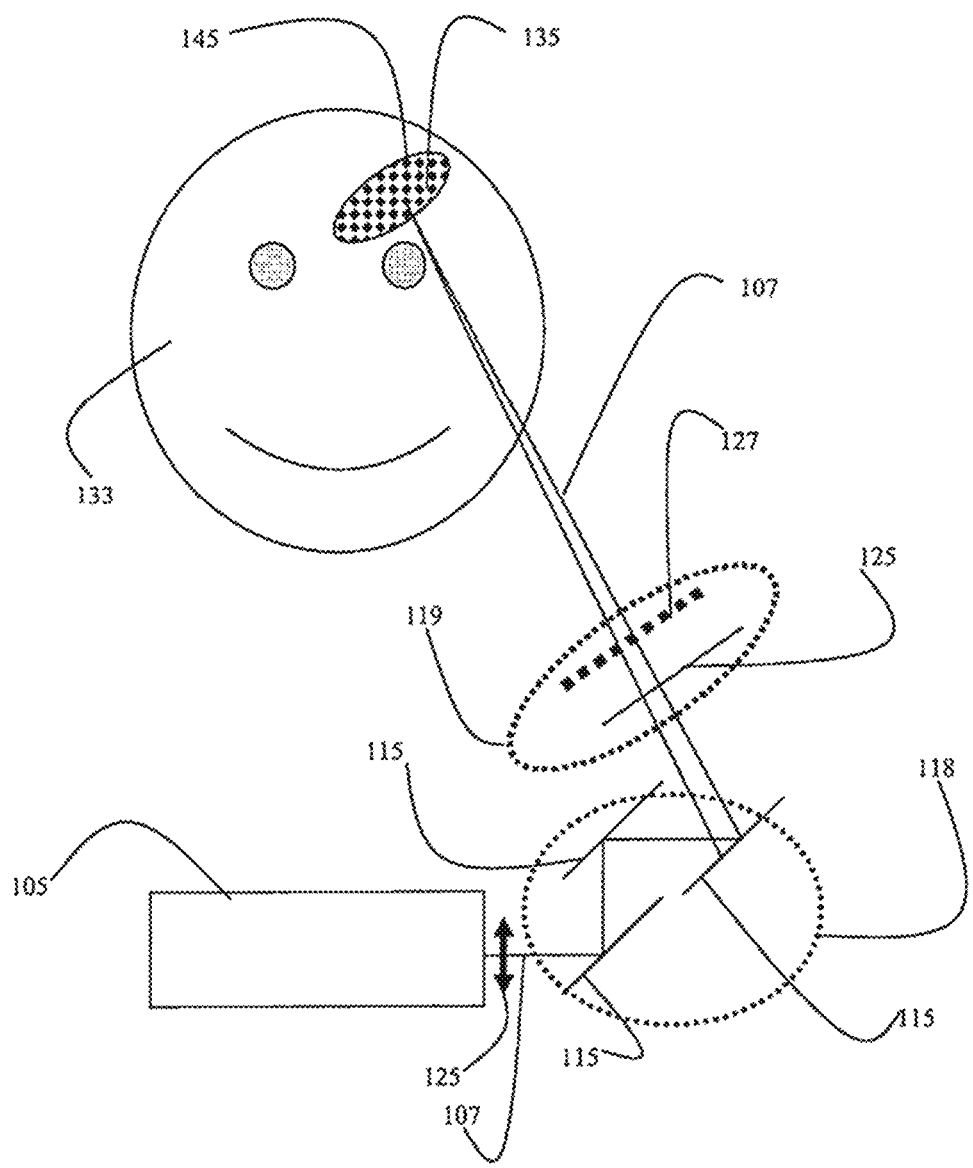
FIG. 11a is a schematic illustration showing a system for creating a pattern of ducts cavities to allow enhanced penetration or sub-skin surface deposition of Botulinum toxin (Botox™) or other chemicals and derma-fillers.
Figure 11B:
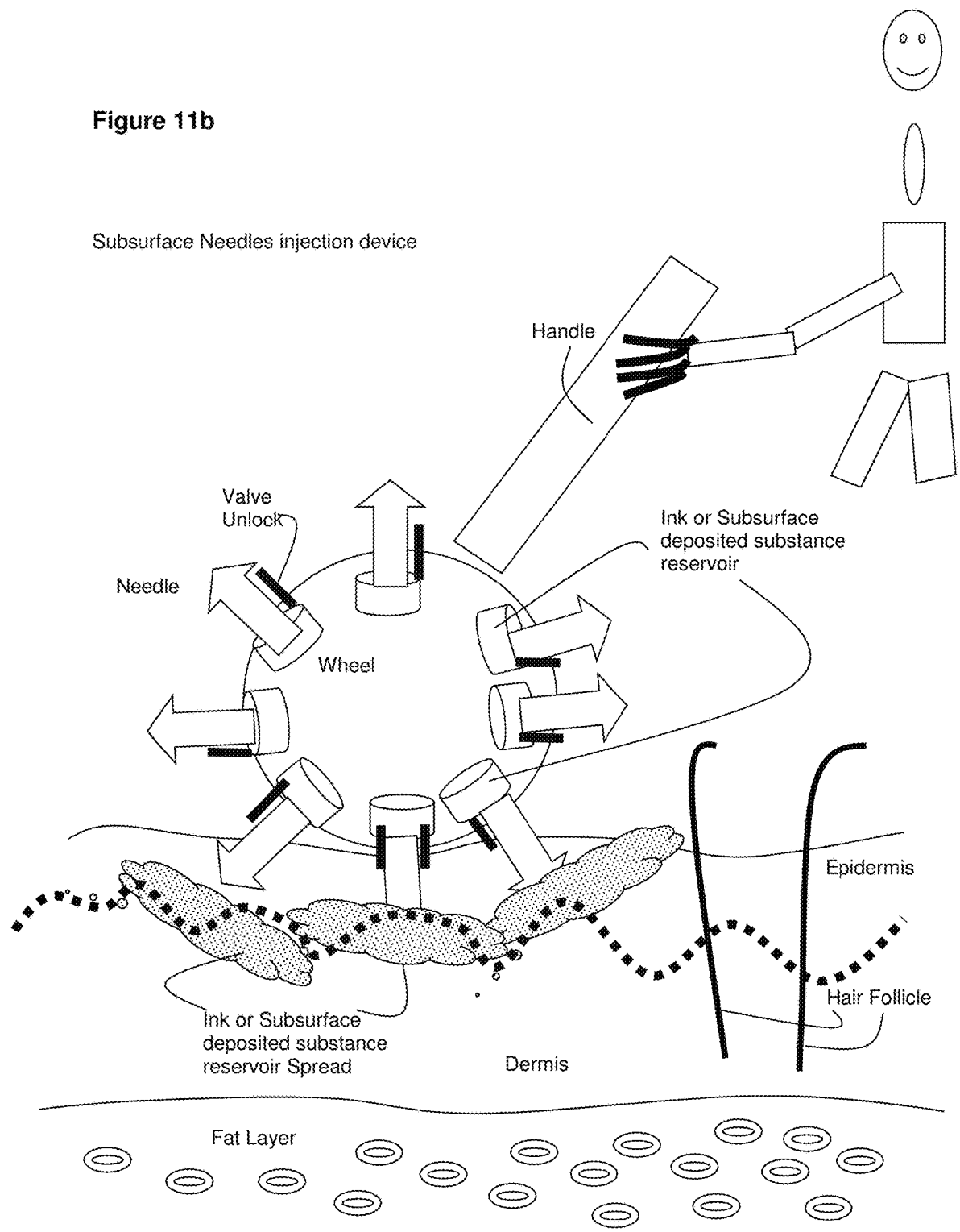
FIG. 11b shows an embodiment of FIG. 16 shows how the embodiments disclosed herein can target the hair papilla and the nourishment sources (e.g. blood vessels) of the hair root at all phases of the hair follicle life cycle.

FIG. 11b shows a preferred embodiment, subsurface modification and injection of substance. This can create, body art, long term skin protection, or wrinkle removal similar to Botox™. FIG. 11c shows how an injectable substance is injected by the needle of the wheel shown in FIG. 11b.

Preferred Embodiment—Cavity Diagnostics

A micro-cavity biosensor monitors optical resonances in micro- and nanostructures for label-free detection of molecules and their interactions. Recent applications allow optical microcavities for nanoparticle detection, trapping and manipulation, and I will highlight different modalities for ultra-sensitive label-free bio-sensing. The embodiments disclosed herein contemplates the creation of microcavities (for example—with fs lasers) within a biological tissue, for example within the environment of the eye. Changes in light trapped within the eye are then monitored to detect the presence of atoms, molecules, proteins, and viruses within the tested environment, including insulin level.

Ultrashort pulse lasers has several unique interaction characteristics that make them ideal for several traditional dermatological treatments such as tattoo removal, hair reduction, skin rejuvenation, and treatment of pigmentation.

The characteristics include: Ability to interact with subsurface structures within the skin without damaging the skin; Ability to heat subsurface structures within the skin without damaging the surface of the skin; Ability to target and damage very localized regions of the treated volume with minimal or no collateral damage; Color-blind interaction (insensitive to tissue type or hair color); and Threshold enabled interaction which can be tuned for tissue or target region absorption enhancement.

Subsurface skin modification (SSM) procedures are based on the physical phenomenon of "3-D optical breakdown for material modifications". Using this phenomenon, microscopic interaction can be created inside the surface of the skin by focusing ultra-short pulses of laser light into it.

In Hair Treatment, (as shown in FIG. 1b) an Ultrashort pulsed laser beam is directed and focused at the hair follicle or hair bulb below the surface. The location of the hair bulbs can be determined through the use of OCT or through other imaging and feedback techniques. In essence the ultrashort pulse laser generates a "subsurface haircut" or a subsurface elimination of the tissue responsible for hair growth. The method is hair-color blind in the sense that the interaction is not very sensitive to hair color. The interaction can create a plane of damage at the level of the papillae or cell matrix feeding the hair or responsible for its growth. The damage is permanent to the hair bulb and matrix but is minimal and recoverable for the rest of the skin tissue. Tissue clearing and tissue compression techniques can also be used to enhance penetration.

Figure 12A:
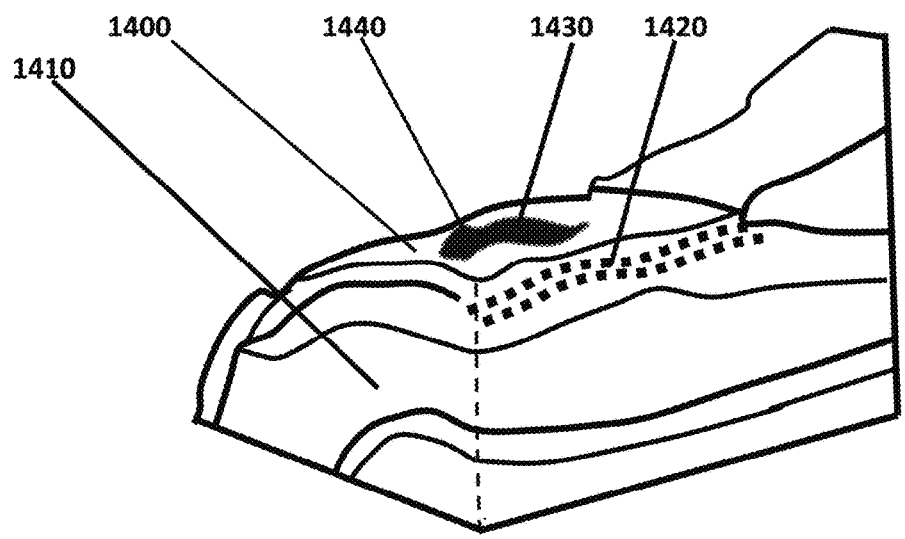
Figure 12B:
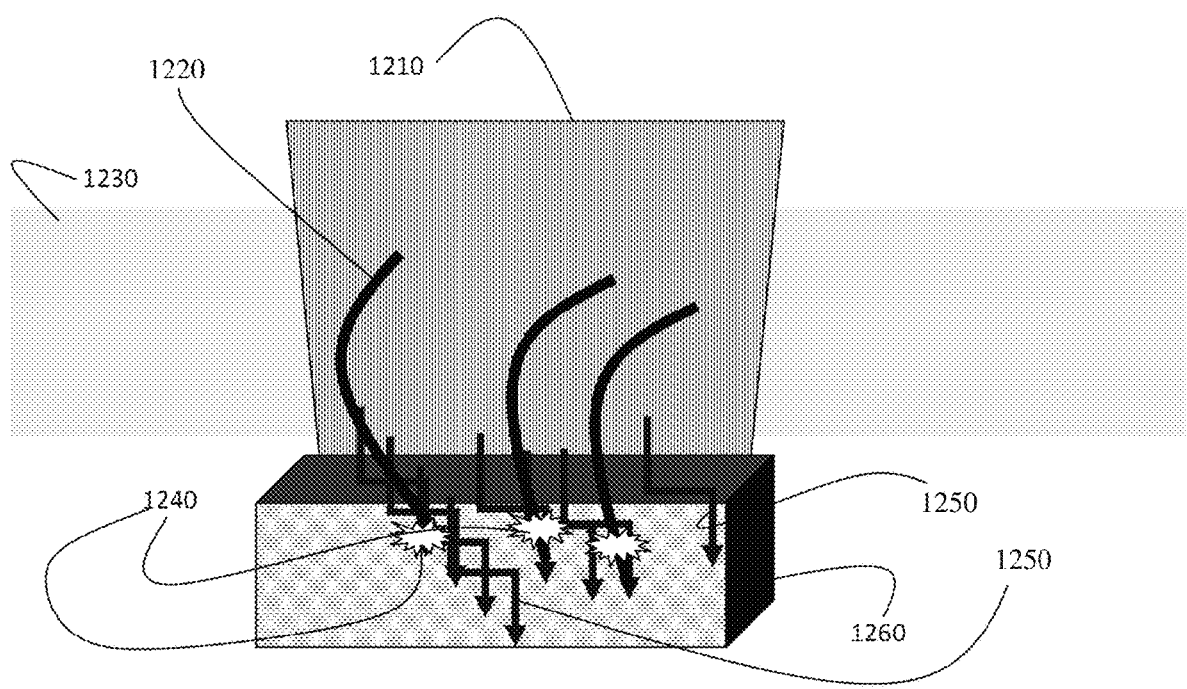

Another substantial advantage of the multi-photons ultrashort pulse based method over conventional method (see FIG. 12b) is in hair removal and other skin methods is their ability substantially delivers much of the light to the target as oppose to "wasting" it on collateral damage and adjacent tissue. As shown in FIG. 12b, a beam of light (for example, a broad ban flash lamp pulse, or a CW diode laser beam, 1210) is directed towards the skin epidermis 1230 and Dermis 1260. The Beam is absorbed by the melanin in the colored hair 1220, and created an interaction that at least partially damages the hair. The interaction is shown by 1240. The Light photons in the beam scatter around the tissue 1260, for example as in the passes 1250, until they encounter the melanin colored hair and get absorbed to create at least partial damage to the hair 1220 and preferably to the hair bulbs and roots. For example, if an 800 nm light source is use, some absorption and heating occurs as the beam passes through the surface and upper layers of the skin. In fact, most of the beam is not used in the target but rather is scattered, reflected and ultimately (whatever portion is not reflected or scattered out of the target) is absorbed in the tissue regions outside the targets.

The beams are often very large in diameter (e.g. up to 1 inch or even 3 inch) and the interaction is based on melanin absorption in the hair follicles. For this reason the light has to be absorbed well by the hair, and hence blonde, white, red, and gray hair are not very responsive. In addition because of the hair growth phases, light may be minimally absorbed during the dormant stage of some hair follicle. Further, depending on the amount of melanin presence absorption may be week. Finally, to compensate, some devices and clinicians may use higher pulse or source energy resulting in burn and collateral damage.

The case is different for short and ultrashort pulse capable of multi-photon interaction, where the light is focused in time and/or space to create an above threshold event at or near the target. When such a threshold power density is created, the much of the pulse energy (except for the energy reflected at the surface or absorbed/scattered on its way to the target) is absorbed by the target or its immediate surrounding and is used to create the photo-disruption damaging event regardless of the absorbing capabilities or color of the hair at the target. In other words, the method does not depend on the target absorption to kill the hair bulb. One kills the hair bulb by aiming and "shooting" the pulse into it.

Figure 13:
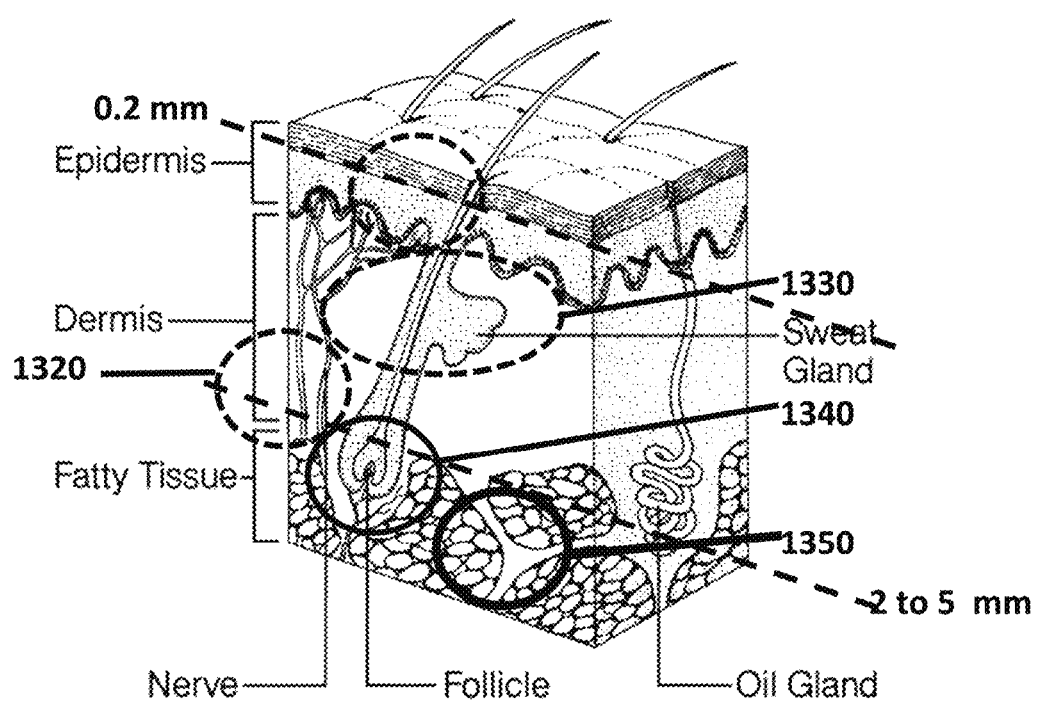

FIG. 13 shows possible target of the method and device. Similar to the described short pulse energy Multiphoton (MP) interaction and modification of the hair bulb 1340, the interaction can be directed towards fat or cellulite layers 1350, the interaction can also be directed towards the sebaceous gland 1330, and acne problems, the sweat gland 1320, or towards pigmentation and vascular blemishes 1310, or other vascular problem such as Port wine stains, 1310, hemangiomas, rosacea, cafe Ole' stains, hypopigmentation or hyperpigmentation or other problems in the epidermis and/or dermis.

Alternatively or additionally, the Ultrashort pulse beam can be made to converge (temporally or spatially) towards the targeted hair root. Above the hair root, the pulse energy density is too low for interaction, at the hair root, the pulse energy density is close to interaction threshold but can be made CLOSE to said interaction threshold and thus, when encountering the slightly higher absorption of root the pulse energy density reaches the interaction threshold and causes permanent damage to the hair root or hair too matrix. This version of the USPL interaction does rely on slight absorption but only to trigger the above threshold event. The pulse compression (temporal or spatial) is the mechanism responsible for bringing the energy close to interaction and sparing overlying or underlying tissue. The higher absorption in the roots is the mechanism responsible for sparing the lateral damage to adjacent lateral tissue.

Similar USPL mechanisms can be used in the treatment of sebaceous gland for permanent curing of moderate to severe acne, in treating tattoos, and in treatment of port wine stains, vascular or pigmented lesions. Additionally, similar USPL can be used to treat fungus and other nail ailments.

FIG. 14 and FIG. 15 show the capability of technologies known in the art, for example, ultrasound imaging, FIG. 14, or Optical Coherent Tomography (OCT) FIG. 15, to image hair follicle and hair roots and thus guide the short or ultrashort pulse interaction with subsurface capabilities as described by the embodiments disclosed herein.

In one embodiment, a device for enhanced energy delivery to the skin is contemplated. The device comprises an energy source, means for directing energy from said energy source towards said target, means for compression of a target material.

In another embodiment, a device for enhanced energy delivery to the skin is contemplated. The device comprises an energy source, means for directing energy from said energy source towards said target, means for mechanical compression of a target material and means for synchronizing said energy source and said mechanical compression mean. In further elaboration of the above embodiments, the means for compression of the target material comprise a contact surface configured to contact and press against the target material.

Further elaboration of the device above envision using a mechanical means to drive said compressing contact surface into the target material, for example, as a non-limiting example, a motor driver, a shaft and a piston can be used, wherein said motor may be an electric motor or any other kind of motor known in the art.

In further embodiment of the devices above, said mechanical means comprises a surface capable of deforming and exerting mechanical pressure on the target surface.

Additional embodiment of the device further envision the mechanical means comprises a contact surface configured to contact and apply mechanical pressure on a target material, and means to drive said contact surface towards the target surface. The contact surface may be configured one or more of a group comprising: Flat surface; Surface with pins or protruding members; Curved surface; Rough surface; Surface with pins; Surface with protruding rods; Surface with protruding pyramids; Irregular protrusions form the surface.

The device may further comprise of an electric motor as a means for driving said contact surface towards the target material. The device may further comprise a mechanical motor for driving said contact surface towards the target material. The device may further comprise of an electric motor as a means for driving said contact surface towards the target material. The device may further comprise a transducer or an actuator for driving said contact surface towards the target material. The device may further comprise of a piezo-electric crystal driver as a means for driving said contact surface towards the target material. The device may further comprise of another me means known in the art for driving said contact surface towards the target material.

The device above may further comprise a contact surface which may be transparent. In further embodiment the device contact surface may be made of one or more of the following materials: Metal, Plastic, Dielectric, Glass, Semiconductor, Super conductor, Aluminum, Stainless still, Copper, Brass, Silver, Gold, Titanium, Carbon composite, Transparent materials, Biocompatible materials, Opaque materials, Thermally conductive material, Thermally isolating material, Electrically conductive materials, Electrically insulating materials.

In additional embodiment of the device above—the above device contact surface may be cooled by one or more of the following methods: Thermoelectric cooling, Spray cooling, Freon-type coolants, Air cooling, Expending gas cooling, Circulating liquid cooling, Circulating fluid cooling, Other cooling methods known in the art.

In additional embodiment of the device above—the above device contact surface may be heated by one or more of the following methods: Thermoelectric heating, Heating using spray, Heating using steam, Warm air heating, Electric heating, Mechanical heating, Circulating warm liquid, Circulating warm fluid, Other heating methods known in the art. In further embodiment the contact surface may be made partly of metal and partly of dielectric. In further embodiment the contact surface may be partly heated. In further embodiment the contact surface may be partly cooled. In further embodiment the contact surface may be partly cooled and partly heated. In further embodiment the contact surface may be made at least in part of metal said metal is connected to a cooling source, for example, TEC, or cooling spray, or cooling flow.

EXAMPLES

Example 1. 88 MHz Device and Method for Non-Ablative Skin Rejuvenation

In turbid media such as the skin, multi-photon processes with low energy and high pulse repetition rate (PRR) (e.g. 88 MHz) can be used to create a non-ablative skin rejuvenation but with a higher precision targeting at the designated depth. Instead of heating the bulk of the skin, one can target the skin at a predetermined depth through multi-photon (MP) non-linear absorption at that depth due to the high photon density of the ultrashort pulses. At high PRR, sufficient heat accumulates to create a controlled thermal damage at that particular depth and that particular target location. Through scanning or other means of moving the beam (e.g. diffractive optics or Kinoform waveplate), a pattern of focal spots is produced where controlled thermal damage will occur. Using MP absorption based selective heating, no surface cooling is needed. Selective damage can thus happen without cooling of the surface, or at least with much less cooling of the surface than is required by conventional devices.

Example 2. A Multi-Photon (MP) for Protecting Fruit Seeds and Vegetables

Here, a train of ultrashort laser or other energy pulses can be used to make the pattern and fill it with an insulating material. Protection can be achieved from bacterial agents, worms, biohazards, chemicals, pesticides (for organic-like material protection), from temperature variations, from mechanical disruption, from moisture, salts, contaminants, etc.

Example 3. A Multi-Photon (MP) Method and Device for Treating Acne

Here one targets sebaceous glands using a multi-photon process with low energy and a high pulse repetition rate (e.g. 88 MHz), reduce or eliminate acne. The effect can be either ablative, by focusing ultrashort pulses below the surface of the skin into the region of the sebaceous gland, or non-ablative, for example by using an ultrashort pulse laser (USPL) train of pulse and creating subsurface cumulative thermal modification processes such as heat accumulation by targeting ultrashort pulse (USP). Alternatively, one could create MP processes below the surface of the skin at the region close to or on the vicinity of the sebaceous glands thus partially or fully destroying or affecting the sebaceous gland so that over production of sebum or fat is reduced or eliminated.

An OCT, CDT, ultrasound, or any other guiding method can be used to help focus the beam onto the targeted region.

Example 4. A Multi-Photon (MP) Method and Device for Hair Removal or at Least Partial Hair Reduction In this case, ultrashort pulses are used to target the hair root, hair papilla, or matrix feeding and nourishing of hair follicles. As discussed above, the process can be non-ablative, and preferably creates MP processes below the surface of the skin at the region close to or on the vicinity of the sebaceous glands. That process partially or fully destroys or affecting the hair root or hair papilla or matrix feeding and nourishing so that the growth of hair is reduced or eliminated, irrespective of hair color. Here again, an OCT, CDT, ultrasound, or any other guiding method can be used to help focus the beam onto the targeted region.

Example 5. Pulse Compression

Ultrashort pulses directed down the epidermis and dermis or other tissue or material are compressed by the medium as it propagates, so that when it arrive at the targeted region (for example the vicinity of the hair bulb or papilla) its power density is enough to damage said target.

Example 6. Dermal Texturing

Interactions to enhance or reduce the penetration of light or to create channels for the modifications in the delivery of drugs or light or heat into skin.

It is known in the art to apply sunscreen to the skin so that harmful sunrays are blocked from entering the skin and thus reduce the probability of some regions of the skin becoming malignant. Such methods however suffer from significant deficiencies. First they may offer incomplete or partial blockage of sun-rays. In addition, many people forget or do not wish to put sunscreen which are uncomfortable and often greasy or oily and can be easily washed by water. Some clothing work well for protecting the skin from damaging energy but these also prevent ventilation and in hot climates or hot days all across the globe, create excess heating of the human body and a sensation of discomfort. Lotions may also plug pores and prevent proper hygiene of the skin or cause skin irritation. Clothing does not protect the skin from chemical or other substance that may come in contact with the skin. Neither closing nor lotions and cream may be able to protect the body from biohazards microbes, viruses, and chemical or biological agents that may be applied to the human skin inadvertently or on purposed by a hostile entity.

It is also known in the art to apply to the skin or under the skin a range of substances that allow increasing the volume or content of the skin (the so called "dermal fillers") and to inject drugs and medicine etc.

A preferred embodiment describes a method and a device that allow the creation of porosity or porous media from a normal skin. This create a "sponge effect" for such dermal fillers, drugs, medicine, or any other substance that we may want to store, inject, or incorporate into the skin. An additional preferred embodiment also describes a device and a method that allow the users to create ducts and minutes ducts or capillaries to couple a substance from the surface of the skin or a tissue to the porous area below the skin.

FIG. 2A shows such a porosity and storage generating device. In a preferred embodiment, an energy source 200 and 210 capable of being focused under the tissue or skin surface 143. The source's energy or energy beam is focused below the surface to create an assembly of partially or fully connected cavities 177 and 178 below the surface at a targeted depth 178. For example in the skin the depth may be in the epidermis 143, in the dermis 183, in the fat layer 193 or even in the muscle or bones 194. The cavities 177, 149 may be connected to each other or may be connected in part (some are connected and some are not) or may be an assembly of individual cavities that are not connected. The assemblies of cavities thus form regions of the tissue or skin with enhanced porosity 178. The porous regions of the tissue or skin 178, can then be connected to the surface with a series of ducts, wells, holes, drilled holes, or ablated holes 179 generated by the device. The ducts or pores may be generated by the device. Such a device, for example a laser and preferably an ultrashort pulse laser, ablating or cutting the tissue or skin in holes or wells stretching from the surface down through the various layers to the subsurface, device-generated porous regions 178.

In a preferred embodiment the ducts are generated by extending some cavities upward form the porous region 178 towards the surface. Such cavities 178, 179, thus form ducts 179 which or extended pore which connect the surface to the porous region 178. The ducts are generated by focusing the beam below the surface of the tissue or the skin and moving the focus up until the cavities thus generated reach the surface. By using this preferred embodiment, the surface can be minimally disrupted and pores and ducts generated under the surface with minimal cutting or ablating of the surface and sometimes without even perforating it at all. For example, the surface of the skin is partially porous and contain hair follicle opening and sweat gland openings. These opening can be used as connections and conducts to this device-generated ducts and pores that lead deeper into the skin or tissue or into the device-generated porous region 178.

In another preferred embodiment the ducts, conduits, and channels, 179 may be generated by filaments, transients mechanical effects such as a bubble, or self-focusing filaments. These effects can be used to extent enhance or replace some or most of the cavity generated by direct device generated cavities 178. They can be used in combination with the direct-device generated bubbles such as ultrashort pulse generated cavities to create a network of channels and ducts leading to the porous generated area or for creating pours region all by themselves.

As shown in FIG. 2A, the embodiments disclosed herein contemplates using an energy source, 200, 210, for example in a preferred embodiment an ultrashort pulse laser with pulse duration of about 10 ps or less, or an ultrasound energy source, or a focusable microwave energy source or other electromagnetic energy source. The energy from the source go through a plurality of focusing elements 199, 122, the energy beam passes through a plurality of mirrors 103 and scanners 196 and is focused to target regions below the surface 143 of the skin, for example to spots 177 or 149, etc. The porous regions 178 can be generated in the epidermis area, 143, dermis, 183, fat, 193, or muscle 194.

Example 7. Multi-Photon (MP) Method and Device for Utilizing Structural Generation of Colors in Skin and Tissue Structural colors are colors which are caused by interference effects rather than pigment. Colors are produced when a material is scored with fine parallel lines, formed of one or more thin parallel layers, or otherwise composed of microstructures on the scale of the color's wavelength. If the microstructures are spaced randomly, light of shorter wavelengths will be scattered preferentially to produce Tyndall effect colors: the blue of the sky, aerogel of opals, and the blue of human irises. If the microstructures are aligned in arrays, for example the array of pits in a CD, they behave as a diffraction grating, the grating reflects different wavelengths in different directions due to interference phenomena, separating white light into colors. If the structure is one or more thin layers then it will reflect some wavelengths and transmit others, depending on the thickness of the layer(s).

Structural color is studied in the field of thin-film optics. A layman's term that describes particularly the most ordered structural colors is iridescence. Structural color is responsible for the blues and greens of many bird feathers (example, blue jay feathers) as well as certain butterfly wings and beetle shells. Variations in the pattern's spacing often give rise to an iridescent effect, as seen in peacock feathers, soap bubbles, films of oil, and mother of pearl, because the reflected color depends upon the viewing angle.

In this case one applies high pulse repetition rate (PRR) laser either at the surface of the skin or below the surface of the skin to create reflective effects that will result in changes to skin coloring. Alternatively, and in a preferred embodiment, pattern induced by the high PRR pulses of electromagnetic energy either at the surface or below the surface of the skin can be used to reflect unwanted radiation or wavelength and prevent penetration into the skin or tissue or other material one wishes to protect. In a particular embodiment, a high pulse repetition rate laser running at a pulse rep rate of from about 10 Hz to about 100 MHz, from about 1 KHz to about 100 MHz can be used, with sufficient power density, (for example with pulse duration from about 1 microsecond to about 1 fs, from about 10 ns to about 3 fs) and pulse energy from about 0.01 nJ to about 10 J, from about 0.1 nJ to about 1 J and spot size at the surface of from about 0.01 µm to about 100 mm, from about 10 µm to about 2 mm, along with a scanner or other elements that are capable of moving the beam along the targeted surface of bulk volume (for example, galvanometer scanners, spinning polygon, or vibrating lens, among other methods known in the art for scanning or stirring beams), so that the a pattern is created that rejects or reflect certain colors or wavelengths.

Destructive interference in the forward direction can be created to reject wavelength in the range of from about 170 nm to about 400 nm thus reducing the penetration of cancer-causing radiation in the UV. Alternatively a reflection of sunlight or room light in the wavelength that appears to the eye in the color of tanned skin can be useful aesthetically to enhance the perception of beauty and healthy-looking skin to the eye of the observer. Many other possibilities of reflected or transmitted colors can also be envisioned for protecting the skin or underlying tissue, for beauty or aesthetic reasons or for enhancing light and/or other forms of energy penetrating the skin for therapeutic or diagnostics or research purposes.

Example 8. Multi-Photon (MP) Method and Device for Enhanced Penetration Across a Barrier A series of cavities can be generated in the z-axis direction. These can be inter-connected to create an effective channel for the delivery of drugs or medicine or for example, for the storing of drugs, medicine, nutrient and vitamins within the tissue or skin for controlling aging, for disabling muscles such as in the action of Botox or similar derivatives and chemicals that disable facial muscle or other body muscles, for the control of diseases such as diabetes or other skin diseases.

In FIG. 1a, for example, the cavities can be connected to each other or can be connected in part (some are connected and some are not) or can be an assembly of individual cavities that are not connected. The assembly of cavities thus forms a region of the tissue or skin with enhanced porosity. The porous region of the tissue or skin 177, can then be connected to the surface with a series of ducts or ablated holes 179 generated by the device. The ducts or pores can be generated by the device ablating from the surface down through the various layers until it arrive at the device-generated porous region 178. As FIG. 1a also shows, such region of the target or skin with a pattern of volumetric modified micro zones (PVMM) 178, can be generated in the epidermis, dermis, fat layer or any combination of the three. For example, using techniques set forth herein, a PVMM 178 can be generated in the epidermis, and fat layer, or epidermis and dermis, or dermis and fat layer, or just the epidermis, etc.

In a preferred embodiment the ducts are generated by extending some cavities 179 upward from the porous region 178 towards the surface. The extended cavities 179 thus form a duct 179 which or extended pore which connect the surface to the porous region 178. The ducts are generated by focusing the beam below the surface of the tissue or the skin and moving the focus up until the cavities thus generated reach the surface. By using this preferred embodiment, the surface can be minimally disrupted and pores and ducts generated under the surface with minimal cutting or ablating of the surface and sometimes without even perforating it at all. For example, the surface of the skin is partially porous, and contains hair follicle openings and sweat gland openings. These opening can be used as connections to ducts and pores that lead deeper into the skin or tissue, or into the device-generated porous regions 178.

In another preferred embodiment the ducts, conduits, and channels, 179, can be generated by filaments, transient mechanical effects such as a bubble, or self-focusing filaments. These effects can be used to extent enhance or replace some or most of the cavity generated by direct device generated cavities 177. They can be used in combination with the direct-device generated bubbles such as ultrashort pulse generated cavities to create a network of channels and ducts leading to the porous generated area or for creating pours region all by themselves.

Such porosity-generating patterns can be made from the bottom up meaning that the pattern can be generated at the bottom of the skin (for example in the layers in the dermis or mid-reticular dermis or upper dermis, or in the lower epidermis) and then and then sequentially a pattern can be generated in the upper layers of the skin.

Example 9. Dermal Filler

It is known in the art to apply sunscreen to the skin so that harmful sunrays are blocked from entering the skin and thus reduce the probability of some regions of the skin becoming malignant. Such methods however suffer from significant deficiencies. First they may offer incomplete or partial blockage of sun-rays. In addition, many people forget or do not wish to put sunscreen which are uncomfortable and often greasy or oily and can be easily washed by water. Some clothing work well for protecting the skin from damaging energy but these also prevent ventilation and in hot climates or hot days all across the globe, create excess heating of the human body and a sensation of discomfort. Lotions may also plug pores and prevent proper hygiene of the skin or cause skin irritation. Clothing does not protect the skin from chemical or other substance that may come in contact with the skin. Neither closing nor lotions and cream can be able to protect the body from biohazards microbes, viruses, and chemical or biological agents that can be applied to the human skin inadvertently or on purposed by a hostile entity.

It is also known in the art to apply to the skin or under the skin a range of substances that allow increasing the volume of the skin (the so called "dermal fillers") to inject drugs and medicine etc.

According to teachings herein, porosity of skin can be significantly increased, to create a "sponge effect" for dermal fillers, drugs, medicine, or any other substance that we may want to store, inject, or incorporate into the skin. It is still further contemplated for users to create ducts and minutes ducts or capillaries to couple a substance from the surface of the skin or a tissue to the porous area below the skin.

Example 10. Treatment of Nail Diseases, Using the Creation of Subsurface Spaces Created within the Nail for Storage of Drugs, Medicine or Nutrients Yet another preferred embodiment contemplates a device and a method for modifying tissue and spaces underneath the human or animal nail. Utilizing properties of multi-photon interaction and three dimensional materials processing, a pulse train from an energy source is directed towards zones underneath the surface of a nail for the creation of subsurface spaces as described elsewhere herein. These spaces can then be used to storage medication to fight algae or bacteria or viruses or other ailment underneath the nail surface or underneath the nail.

The pulse train can also be used to heat or ablate or otherwise destroy targets (for example viruses or microbes) underneath the near surface or under the nail substantially without damaging the nail surface.

Example 11. Pigmented Lesions And Tattoos

Ultrashort pulses condense a sufficiently large number of photons into a small space and time regime. If the photon density per unit time is sufficiently high, a physical processes that result in permanent change to the tissue property will take place.

As described herein, ultrashort pulses can be used to remove tattoos and improve skin conditions. When the objective is removal of pigmented lesions or tattoos, the existing problems and questions are as follows: (1) How does one remove the pigment without scarring the tissue? (2) How does one achieve a nearly complete pigment removal so that substantially no unfavorable cosmetic evidence remains visible? (3) How does one remove all various color of the tattoos (e.g. black, blue, green, red, yellow, etc.)? and (4) How does one minimize pain and collateral, unwanted tissue damage?

Existing techniques (as described in various reviews, (for example by Dr. Tina Alster review article), often rely on short pulse lasers. However, these laser systems are often wavelength specific and have limited efficacy in the off-black ink color (e.g. red and yellow). For example, the Nd:YAG nanosecond laser has limited efficacy in removing yellow or red tattoos. Such laser devices are also often painful, of limited in efficacy and require multiple (5, 6, 7 or more) treatment. Patients often run out of money, patience or both during the course of these multiple sessions, and months' long treatments.

Because of their ability to concentrate photons in an ultrashort time and microscopic spatial location, ultrashort pulses of energy, as mentioned above, are able to initiate the interaction process in a nearly absorption free media (such as water or air) and certainly in tissue, with little regard to specific tissue components absorption characteristics.

Example 12. Tattoos

In the case of tattoos the beam is directed towards the tissue containing the tattoos but aimed so that if a free space was replacing the tissue, the beam focal spot would be well below the tattoo ink location, for example, from about 100 um to about 1 mm below the tattoo ink location, but in any event, a focal spot location below the tattoo location, such that the ultrashort pulse beam size at the tattoo is large so that the photons number per unit area per unit time, are substantially below the interaction threshold. The beam focus is then raised, for example by changing the position of a lens in the beam path. As the focal spot is getting close to the location of the tattoo ink location, the photon density is raised until at some point the photon density is sufficiently large to start the interaction process resulting in photodisruption and at least some breakup of the tattoo ink particles.

In yet another embodiment, not only is the beam focus moved up from below the tattoo location to towards the surface of the skin, but the beam is also scanned laterally. Furthermore, as the beam is scanned latterly the device is also design to include a monitor to look for evidence of the start of the breakup of the ink in the tattoos. Such a monitor may include a photodiode, or an emission detector, or a spectrometer, of a photodiode with a filter to block out the backscatter incoming femtosecond light color. The monitor may also include a detector of photomechanical effect in the tissue, or a detector of an induced photothermal effect in the tissue. Other detectors and monitors may also be envisioned. Regardless of the nature of the detector, when the effect of physical changes in the tattoos are detected, the monitor passes as rapidly as possible (for example an electronic feedback signal) to the motor moving the lens or any other method or component used to cause the beam focus spot position to move, such that such motion is stopped. The beam continue to be scanned laterally so that the entire area of the targeted tissue or tattoo spot is covered with sufficient number of passes to cause at least some reduction in the appearance of the tattoo.

The advantage of this embodiment and employment of the feedback monitor, AND the stopping of the changing in the beam focal spot position as soon as (or at least close to) the initiation of the breakup or changes in tattoo characteristics, is because the user minimize the use of energy and excess energy and work close to threshold level to minimize pain and collateral damage. In addition, another advantage is that normal tissue or skin (which does not contain tattoos or pigments or absorption centers) will still be UNDER the threshold for interaction photon density while the targeted tissue or tattoo (even with lower absorption dyes such as red or yellow dyes) will provide sufficient absorption to provide sufficient number of photons to be added to the photon density in the targeted volume to result in photodisruption in the targeted tattoos or, over time, in at least some reduction in the visibility of the targeted tattoos.

Embodiments according to the teachings herein can provide some or all of the following advantages in tattoo removal: (1) Allowing more complete removal of tattoos of all types of ink (including black ink); (2) more complete and more efficient removal of all inks with less pain and less collateral damage and the reduce risk of scaring or permanent unwanted damage to the skin; (3) more complete and more effective removal of off-black in tattoos; (4) less pain; (5) faster treatment (faster treatment time from start of treatment to finish); 6). Fewer treatment session; (7) faster healing, reduced recovery time; and (8) less complications, and fewer if any side-effects.

The method utilizes ultrashort pulses of Electromagnetic (EM) radiation, (for example shorter than about 10 picoseconds), These pulses are used in combination with (1) high photon density (PD) and (2) the increase absorption added to the skin native tissue by the presence of the tattoo dye which is sufficient to get the photon density at said tattoo location to above the threshold for breakdown.

Note however that the photons density (number of photon per unit volume) in the targeted skin must be such that the PD native skin (PDns) is below the PD for interaction threshold (PDi) and PDns<PD. As we increase the photon density at the targeted pigment or tattoo ink the PD at the ink is sufficient to bring about light induced breakdown and thus a breakup of said pigment or tattoo ink in the target.

Not that a long pulse light or a continuous wave (CW) laser will not have sufficient photon density to break up the pigments or tattoo dyes even with the increase absorption at the dye. Long pulse or CW laser will simply heat up the target but not result in photomechanical breakup of the targeted dye or in a breakdown and photodisruption of the target.

In one preferred embodiment the beam design is such that no interactions occur at the skin surface but the interaction does occur at the color pigments of the tattoo. Because USP generate high transient photon density as they propagate into the targeted material, they are already at the threshold for interaction and thus just a small absorption increase in the target tattoo or other skin target allow them to go over the threshold limit to begin the interaction and the process of a breakup of the tattoo dye color.

Long pulses will not trigger an interaction with low absorbing color (e.g. red) because the interaction threshold or threshold photon density (number of photon per unit area per unit time) is too far because of the long temporal spread. But USP are close to the needed PD threshold thus an interaction will be triggered even with a weekly absorbing dye.

In a preferred embodiment we sweep the energy per pulse as we scan laterally with the beam focus is fixed—across the targeted area. As the pulses energy is increased, the interaction threshold is reached and damage to the ink droplet or other targets in the skin is induced.

In an alternative preferred embodiment we can increase change the beam size at the targeted tattoo or skin location from a large spot size to a smaller one so that when the PD threshold is reached interaction is induced.

In yet another preferred embodiment, we can also add a detector to monitor the interaction threshold. For example we can detect the onset of optical breakdown in the tissue, acoustic signature, or plasma emission, or luminescence emission or some other indicator of an onset of interaction. When such a monitor proved a feedback signal that an interaction with the tattoo has occurred the increase in pulse energy or reduction of pulse spot size is stopped and the beam continue to be scanned laterally with substantially minimal energy needed to generate reduction in tattoo visibility or some other skin effect, while covering the remaining of the targeted tattoo or skin area.

Example 13. Collagen Remodeling/Skin Rejuvenation

According to the teachings herein, one can control damage below the surface of the skin while preserving the integrity of the top layer of the skin, (for example, the top layer can extent from the outer surface to about 10 μm (um) below the surface or to about 50 um or about 100 um or about 150 um or about 200 um or even deeper below the surface of the skin). To chive that goal, the beam of ultrashort pulses of energy, electromagnetic energy are focused below the surface of the skin so that an interaction occurs at a target location below the surface of the skin. When healing will occur tightening of the skin, newer collagen and fresher, younger looking skin will result.

In a preferred embodiment, the creation of such modifications can also employ the effect of self-focusing. In the case when the beam and its pulse intensity are such that the refractive index effect of focusing due to the effect of high energy intensity on the medium (as an example—skin and skin components) refractive index create a lens-like effect of focusing. Such an effect when the beam or pulse intensity is sufficiently high, can result in the creation of additional micro-structures as a result of filaments that create cracks or break in the skin extending beyond the focal point. Such disruption and damage to the skin below the surface of the skin can be useful in skin rejuvenation when upon healing and tissue repair, a new more elastic collagen is generated and a fresher, younger looking skin may result.

The creation of subsurface or sub-skin surface damage using energy, electromagnetic (EM) energy, pulses of EM energy and short and ultrashort pulses of light can be enhanced using an index matching windows and/or lenses. Such lenses when in contact with the skin can reduce energy loss and can help focus the beam of energy below the surface at the desired target location. Furthermore, such windows or lenses, can be cooled to help preserve surface integrity which will help protect the body against infection and contamination and help accelerate healing and minimize pain. In addition, applying pressure to such windows and/or lenses in contacts with the skin, can serve to further compress the distance between the targeted area and the surface of the skin, allowing more light to penetrate into the tissue. Index matching fluid can also be applied to the skin or even be allowed to infiltrate the skin so that beam and/or pulse energy penetration to the skin is further enhanced. Using very short pulses with minimization of thermal damage also allow minimization of pain and faster recover times.

A preferred embodiment envisions direct modification to collagen can be made by creating the following pattern in the treatment of collagen regeneration and skin rejuvenation:

Example 14. Skin Rejuvenation

It is also contemplated that a device that can be used safely to heat a thin layer of tissue without significant collateral damage. It is known in the art to restore skin elasticity, for example by creating a control amount of damage to a region of the skin, for example the upper one third or upper one half of the dermis. This is done for example by using a CO2 laser to create a zone of ablation and a zone of thermal damage in the skin. Alternatively a method known as non-ablative skin rejuvenation is used to create a zone of thermal damage in the dermis without damaging the surface layer of the skin. When the skin heals it is shown to create a more elastic skin with newer collagen. Similarly, it is known in the area to use chemical such as Glycolic acids and other acids or chemicals to create a zone of damage in the upper skin epidermis and dermis. When the chemical damage is repaired a fresher, newer collagen is created the skin is said to be more elastic and fresher looking.

As discussed elsewhere herein, subsurface layers of cavities can be created substantially without thermal damage, by using the ability of multi-photon processes and cavitation to create voids, cavities, and mechanical disruption below the surface of the skin or tissue substantially without damaging the skin or tissue. This novel devices and method has several significant advantages over current techniques: (1) healing time is much shorter. It has been shown the thermal damage and chemical damage to the skin or tissue take significant more time for the body to heal compared to mechanical or chemical damage. The healing time with thermal damage can be days or weeks. It has been shown that tissue or skin mechanical or non-thermal damage can be repaired in much shorter times; (2) the damage is under the surface and thus reduces pain, risk of contamination and infection, and disfiguring or unpleasant appearances; (3) pain is minimized and the use of local anesthetics is reduced; (4) operation procedures is shorter; (5) collateral damage is reduced.

Ultrashort pulse lasers, those shorter than about 10 ps, for example are especially preferred. The damage created by such devices is very confined, well defined and very limited in extent. Because such lasers can be operated at a very high pulse repetition rate large area damage can be created in a very short time, but this damage can be created with discrete individual spots that may or may not be connected. If they are not connected the healing time is anticipated to be even faster.

Using the teachings herein, users can design the pattern of damage with unprecedented accuracy, limit the healing time, and create unparalleled flexibility in the design of the damage, while preserving the skin surface health and integrity. The method and device also allow the use of an entirely new approach to increasing skin elasticity—by creating a new sub-surface structures to the skin it allow the user to avoid relaying on skin natural healing processes alone to increase elasticity and reshaping of the skin. It let the user increase porosity, elasticity, and integrates new porous media (including the possibility of injecting to the skin or the skin accruing additional substances that are stored in the porous or cavities-shaped region) thus created by the methods and devices contemplated herein.

Example 15. Working with Botox, or Generating Botox™-Like Action for the Reduction or Wrinkles Another method for treating wrinkles especially wrinkles that are originated due to action of muscles and can be helped by the use of muscles action modifiers, is the use of toxins. The skin around a person's eyes does not stay smooth like this forever. The repetitive use of surrounding corrugator and procerus muscles can cause severe glabellar (frown) lines.

It is also known in the art to use poisons such asbotulinum toxin (Botox™) to partially or fully disable facial muscle to reduce the appearance of wrinkles on the skin. Methods and devices contemplated herein allow the user to also disable muscle and nerve below the surface of the skin without penetrating the skin surface. Alternatively, in a preferred embodiment, a system of ducts cavities and channels as described below is created to allow the enhanced penetration of asbotulinum toxin (Botox™) or other such chemicals to allow less painful penetration of the skin by such substances.

A device adapted for disabling of facial muscles or other type of muscle or the creation of enhanced penetration ducts and channels in from the skin surface or from just below the surface of the skin. In a preferred embodiment shown in FIG. 11a. FIG. 11a shows an energy source 105 for example an ultrashort pulse laser 105 capable of producing a beam 107 of short pulses of energy that is substantially not absorbed well by the tissue unless the power density is sufficient to create multi-photon absorption. By "not absorbed well" I mean a passage so that the no substantial interaction with the tissue or cell occurs while the energy or EM energy or light passes through them, and so that no irreversible changes to the tissue occurs. The light passes through a plurality of mirrors 115 and a plurality of scanners 118 and a plurality of optical elements 119, such as focusing elements 125, or beam shaping elements, 127 such as Kinform phase plates or diffractive optics (capable of forming multiple beams 107) or lenses, or diffraction gratings, adaptive optics, prisms, polarizers, and similar optical elements 119, to be focused underneath the skin of the face 133, and into the targeted facial muscle 135 (for example, the corrugator supercilii), to a plurality of focal spots 145.

It is especially contemplated that one can use the pattern of cavities or tissue modifications to create storage space or enhanced penetration for substances like Botox or other substances capable of modifying skin and tissue properties so that the skin or tissue can be used to store Botox for other such substances to better control and better deliver these substances to the muscle. The method also contemplates using the pattern of cavity or tissue modification to directly affect the action of the muscle in order to disable or modify such action so that the wrinkles relax or disappear. The method and device are able to generate the following pattern to achieve such action:

For increased reflection and backscattering spot sizes in a range of from about 0.1 µm to about 5 µm can be desired. For storage of lotions and medicine or sun blockers sizes of from about 5 µm to about 50 µm can be more desired.

Additionally and preferably, if for example a series of tissue modified spots are created, spacing between the edges of each spot of modified material thus created can vary in diameter, for example, from about 0.01 µm to about 5 mm, from about 0.1 µm to about 1 mm and more preferable from about 0.2 µm to about 500 µm and more preferably yet form about 0.2 µm to about 200 µm and more preferably from about 0.3 µm to about 100 µm, and more preferably yet from about 0.4 µm to about 50 µm, and more preferably yet from about 0.5 µm to about 25 µm, and more preferably from about 0.7 µm to about 10 µm, and more preferably from about 1 µm to about 5 µm.

In one embodiment, an ultrashort pulse laser device focuses to a desired depth below the skin surface, for example, at a depth of between about 5 µm and about 500 µm below the surface of the skin, between about 10 µm below the surface of the skin and about 200 µm below the skin surface so that a plurality of cavities with a void of between about 0.1 µm in diameter and about 15000 µm in diameter, between about 2 µm in diameter and about 100 µm in diameter would be formed.

In addition longer pulse lasers with sufficient amount of power density can be used, lasers or light sources with absorbing centers injected or available within the targeted tissue or skin volume. An Electric method can be used, an electrode capable of generating a plasma or other electrical means of creating a void in the tissue, electric resistors pulsed or CW capable of heating the targeted tissue, optical fibers may deliver light radiation to the targeted tissue volume, microchip lasers at their fundamental or doubled, tripled quadrupled frequencies or other frequency multipliers. A diode lasers with scanners or diffractive optics components, or such lasers with absorbing centers injected or implanted or otherwise available in the material. Ultrashort pulses or multi-photon pulse sources in a heating or ablating modes can also be used.

RF frequency generators are also available to create voids targeted microwave radiation or targeted ultrasound energy can also create voids or damage pattern for such purposes. Nuclear energy, proton beams, gamma rays or electron beam may also be used.

Example 16. 88 MHz Method and Device for Correcting Hyperopia

In yet another embodiment, a low power ultrashort pulse laser or similar energy source is use to modify the index of refraction of component of the eye for correction of eye sight. In this application, for example, see FIG. 3a, a laser source 310 for example a Ti:Sapphire, oscillator, running at 88 MHz with a pulse energy of for example from about 0.01 nJ to about 100 microjoule, from about 0.1 nJ to about 100 nJ is focused underneath the surface of the eye surface to create modifications that results in sufficient refractive index changes to correct eye sight such as myopia, astigmatism or hyperopia. In this embodiment, the pulses are focused through a transparent medium of the eye to create thermal based refractive index changes without ablating, bubbles, photodisruption or any other mechanical damage or cutting.

A preferred embodiment envisions direct modification to tissue can be made by creating the following pattern in the cornea or lens of the eye:

If for example a series of tissue modified spots are created, the size of the spots can then vary in diameter from about 0.01 µm to about 200 µm, from about 0.1 µm to about 0.1 mm and more preferable from about 0.2 µm to about 50 µm and more preferably yet from about 0.7 µm to about 20 µm and more preferably from about 0.8 µm to about 10 µm, and more preferably yet from about 0.8 µm to about 5 µm, 1 µm to about 5 µm, and most preferably from about 1 µm to about 2.5 µm. The pattern is made optimize the effect desired. For example, for modify the index of refraction of the eye high repetition low pulse energy ultrashort pulses are used in an energy range of 0.1 to 100 nJ, from 1 nJ to 10 nJ and pulse repetition rate of from 1 KHz to 1 GHz and more preferably from 100 KHz to 100 MHz and most preferably from 10 MHz to 90 MHz.

Example 17. Pulse Compression

In yet another preferred embodiment, the embodiments disclosed herein contemplates sending an ultrashort pulse down the epidermis and dermis or other tissue or material. The method and device preferably aim at achieving selective interaction below the surface of a target material or tissue by using pulse compression in a medium. For ultrashort pulse, the pulse will experience compression in time due to dispersion effects as it propagates in the media. The compression of the light in time allows it to reach an above-threshold power density level at a certain distance into the tissue. A distant that can be calculated and targeted to achieve a depth of tissue modification. The pulse is compressed by the medium as it propagates down the tissue so that when it arrives at the targeted region (for example the vicinity of the hair bulb or papilla) its power density is enough to damage said target.

Pulse compression is illustrated in FIG. 4a. The initial pulse at the surface is of shape 433, representing the uncompressed pulse. As the pulse penetrates and propagate through the tissue, it can designed to reach a compressed stage shown in 437 at depth Z0 allowing the power density (I/Volume) to reach above interaction threshold level so that the target or tissue are modified at depth Z0. As an example, a laser pulse can be directed towards the sebaceous gland region and be shaped in time so its power density is below threshold for interaction because the pulse duration is relatively long. As it propagate down the skin the pulse is compressed as described above and pulse reach above interaction power density because the pulse at depth Z0 is compressed. For example the focusing element (for example a lens) 122 in FIG. 2a can be moved or oscillate to allow the location of compressed pulse to vary in depth around the region of the sebaceous gland or melanocytes, or upper reticular dermis, to achieve the desired tissue or healing effect (for example, ablation or non-ablative damage to the sebaceous gland).

High pulse repetition rate (PRR) laser energy can be applied either at the surface of the skin or below the surface of the skin to create reflective effects that will result in changes to skin coloring. Alternatively, and in a preferred embodiment, pattern induced by the high PRR pulses of electromagnetic energy either at the surface or below the surface of the skin can be used to reflect unwanted radiation or wavelength and prevent penetration into the skin or tissue or other material one wishes to protect. Thus, in a preferred embodiment, a high pulse repetition rate lasers running at a pulse rep rate of from about 10 Hz to about 100 MHz, from about 1 KHz to about 100 MHz can be used, with sufficient power density, (for example with pulse duration from about 1 microsecond to about 1 fs, from about 10 ns to about 3 fs) and pulse energy from about 0.01 nJ to about 10 J, from about 0.1 nJ to about 1 J and spot size at the surface of from about 0.01 µm to about 100 mm, from about 10 µm to about 2 mm, along with a scanner or other elements that are capable of moving the beam along the target surface of bulk volume (for example, galvo scanners, spinning polygon, or vibrating lens, among other methods known in the art for scanning or stirring beams), so that the a pattern is created that rejects or reflect certain colors or wavelengths. For example, an destructive interference in the forward direction can be created to reject wavelength in the range of from about 170 nm to about 400 nm thus reducing the penetration of cancer-causing radiation in the UV. Alternatively a reflection of sunlight or room light in the wavelength that appears to the eye in the color of tanned skin can be useful aesthetically to enhance the perception of beauty and healthy-looking skin to the eye of the observer. Many other possibilities of reflected or transmitted colors can also be envisioned for protecting the skin or underlying tissue, for beauty or aesthetic reasons or for enhancing light and/or other forms of energy penetrating the skin for therapeutic or diagnostics or research purposes.

Example 18. Multi-Photon (MP) Method and Device for Enhanced Penetration

A series of cavities can be generated in the z-axis direction. These can be inter-connected to create an effective channel for the delivery of drugs or medicine or for example, for the storing of drugs, medicine, nutrients and vitamins within the tissue or skin for controlling aging, for disabling muscles such as in the action of Botox or similar derivatives and chemicals that disable facial muscle or other body muscles, for the control of diseases such as diabetes or other skin diseases. Such porosity-generating patterns can be made from the bottom up. For example by three dimensional subsurface perpetrations of cavity or discontinuity in the tissue, a series of cavities or spaces or disruptions in tissue continuity can be made to allow beneficial substances such as drugs or liquids or vitamins to be inserted. The plurality of cavities and subs surface pores can be connected to the surface by a plurality of "wells" or channels or drilled holes that leads from the pores to the surface. A porous array of this type can allow a novel method for treating nail diseases or using nails as a storage reservoirs for medicine drugs, or nutrients among other beneficial substances. It can also allow the creation of a more permanent nail coloring. The nail system forms a particularly difficult target for treatment of subsurface diseases such as fungus or viruses. The three dimensional interaction ability of ultrashort pulse lasers and focusable pulses offer a unique and novel system and method for treating of such target underneath the surface of the nail. Additionally and preferably, the three dimensional interaction ability of ultrashort pulse lasers and focusable pulses can create region of increased porosity at the bottom of the nail near the junction of the nail body with the nail bed. The nail bed is rich in blood vessels and can thus serve as a natural coupler of drug and medicine to the body circulatory and vascular system. For example, as FIG. 12a shows an area of increases porosity drilled three dimensionally by a laser or other means to the nail body and couple to the nail bed can allow controlled rate of delivery of drugs, medicines, vitamins and nutrient to the body. Multi-photon (MP) method and Device for Enhanced nail modifications. In FIG. 12a, 1400 is the nail body while 110 is the nail bed directly underneath the nail body 1400. 1420 is a matrix of cavities or storage space drilled three dimensionally into the nail body and reaching into the nail bed 1410 and it network of blood vessels. A series of "wells" 1430 or drilled holes 1430 creates openings through which drugs or medicine or nutrient or vitamins or other beneficial substances, 1440 can be fed into the storage space.

Example 19. Direct Modification to the Skin which can be Made by Creating the Following Pattern of Volumetric Micro-Zones For storage of lotions and medicine or sunblockers, spot sizes of from about 5 µm to about 50 µm can be more desired.

Additionally and preferably, if for example a series of tissue modified spots are created, spacing between the edges of each spot of modified material thus created can vary in diameter, for example, from about 0.01 µm to about 5 mm, from about 0.1 µm to about 1 mm and more preferable from about 0.2 µm to about 500 µm and more preferably yet form about 0.2 µm to about 200 µm and more preferably from about 0.3 µm to about 100 µm, and more preferably yet from about 0.4 µm to about 50 µm, and more preferably yet from about 0.5 µm to about 25 µm, and more preferably from about 0.7 µm to about 10 µm, and more preferably from about 1 µm to about 5 µm.

In a preferred alternative embodiment, continuous lines can be created. A line pattern with individual line diameters ranging from about as little as 0.1 µm to about as much as 5 mm, from about 1 µm in diameter to about 100 µm in diameter and extending over the entire targeted area wherein a fractional surface area of from about 1% to about 99%, from about 10% to about 60% is damaged.

In other embodiments contemplated herein, the average width of the regions of tissue between adjacent micro-lines can be as large as approximately two, three, four, or nine times the average width of the adjacent micro-lines, corresponding to modified tissue regions of about 35%, 30%, 25%, 20%, and 10%, respectively. In still other embodiments, the average width of the un-modified regions of tissue between the micro-lines can be as small as approximately two-thirds, one-half, or one-fourth of the average width of the adjacent modified lines-lines. In still another embodiment, the unmodified region of the tissue corresponds to between about 90% and about 40%. of unmodified tissue.

Example 20. Treatment of a Variety of Skin Conditions and for Protecting Skin from Unfavorably External Influences Devices and methods are contemplated herein for treatment of a variety of skin conditions and for protecting skin from unfavorably external influences. In particular, the device and method provide protection from damaging sunlight or external radiation that may cause cancer or premature aging of the skin. Protection and prevention of damage from heat, mechanical energy, chemical or biological hazards are also contemplated.

The device for treating a region of intact living skin having a surface and an epidermal/dermal junction, includes: an energy source; a controller that cooperates with the energy source to subject the region to an energy pulse having a duration of no more than 10 nanoseconds, at an average energy density that creates measurable modification in at least one of the following group of tissue properties in the epidermis: optical, thermal, chemical or mechanical properties, without substantially denaturing tissue below the epidermal/dermal junction.

Alternatively, the device and method also contemplates creating measurable modification to tissue properties in the dermis without substantially denaturing tissue below the lower boundary of the dermis.

Alternatively, the device and method also contemplates creating measurable modification to tissue properties in the epidermis and dermis without substantially denaturing tissue below the lower boundary of the dermis.

Alternatively, the device and method also contemplates creating measurable modification to tissue properties in the epidermis and dermis without substantially denaturing tissue below the lower boundary of the adipose layer.

Alternatively, the device and method also contemplates creating measurable modification to tissue properties in the epidermis and dermis without substantially denaturing tissue below the lower boundary of the dermis and while leaving a layer of tissue between the surface of the skin and about 5 μm below the skin unmodified. Alternatively, the layer of unmodified tissue extending from the surface of the skin has a thickness of 10 μm, 15 μm, 20 um, 25 um, 30 um, 40 um, 50 um, 60 um or 70 um or even 90 um.

Alternatively, the device and method also contemplates creating measurable modification to tissue properties in the epidermis and dermis without substantially denaturing tissue below the lower boundary of the dermis and while leaving a layer of tissue between the surface of the skin and about 5 μm below the skin unmodified. Alternatively, the layer of unmodified tissue extending from the surface of the skin has a thickness of 10 μm, 15 μm, 20 um, 25 um, 30 um, 40 um, 50 um, 60 um or 70 um or even 90 um and no external cooling is applied by the use or the method and device to the surface of the skin.

Alternatively, the device and method also contemplates creating measurable modification to tissue properties in the epidermis, dermis, adipose, or fat layers without substantially denaturing tissue below the lower boundary of the dermis and while leaving a layer of tissue between the surface of the skin and about 5 μm below the skin unmodified. Alternatively, the layer of unmodified tissue extending from the surface of the skin has a thickness of 10 μm, 15 μm, 20 um, 25 um, 30 um, 40 um, 50 um, 60 um or 70 um or even 90 um and no external cooling is applied by the use or the method and device to the surface of the skin.

Alternatively, the device and method also contemplates placing a transparent contact element on the surface of the skin, creating measurable modification to tissue properties in the epidermis, dermis, adipose, or fat layers, without substantially denaturing tissue below the lower boundary of the dermis and while leaving a layer of tissue between the surface of the skin and about 5 μm below the skin unmodified. Alternatively, the layer of unmodified tissue extending from the surface of the skin has a thickness of 10 μm, 15 μm, 20 um, 25 um, 30 um, 40 um, 50 um, 60 um or 70 um or even 90 um and no external cooling is applied by the use or the method and device to the surface of the skin. In a preferred embodiment, the transparent contact element is a focusing element, preferably a lens or a plurality of lenses.

Preferably, the device and method contemplated herein, also envision the transparent contact element through which the energy propagate to the skin applying pressure to the skin. Preferably the transparent contact element is a lens or a plurality of lenses that also apply pressure to the skin before during or after the applications of energy. Application of pressure or suction in combination with the application of the energy contemplated by the device and method described here will result in the ability to focus or deposit energy, for example ultrashort pulses of laser, in deeper region of the skin or body tissue, for example in the epidermis, dermis, adipose layer, fat layer or muscle.

The device can also avoid damage to the surface of the skin while treating deeper layers. For example, in a preferred embodiment, the launches a beam of energetic pulses into the skin, the pulses leave the surface of the skin substantially free of tissue modifications to a depth of at least 10 μm. In another preferred embodiment the device leave the surface of the skin substantially free of tissue modifications to a depth of at least 20 μm. In another preferred embodiment the device leave the surface of the skin substantially free of tissue modifications to a depth of at least 30 μm. In another preferred embodiment the device leave the surface of the skin substantially free of tissue modifications to a depth of at least 40 μm. In another preferred embodiment the device leave the surface of the skin substantially free of tissue modifications to a depth of at least 50 μm. In another preferred embodiment the device leave the surface of the skin substantially free of tissue modifications to a depth of at least 5 μm.

In a preferred embodiment the modification process is the process of photodisruption. For example, a photodisruption caused by an ultra-short pulse of laser radiation with pulse duration of about 10 picosecond or less and with a wavelength of between about 150 nm and about 1800 nm, between about 700 nm and 1550 nm. Pulse repetition rate is preferably between about 0.1 Hz and 1 Gigahertz, between 5 Hz and 500 Megahertz and most preferably between about 0.5 KHz and 100 MHz. Pulse energy is between 0.01 nJ and 10 Joule, between 1 nJ and 1 Joule, and more preferably between about 1 nJ and 50 mJ and most preferably between 10 nJ and 1 mJ.

Preferably, the device creates tissue modifications in the tissue that change the optical characteristics of the tissue. For example, the process of photodisruption can create cavities and or discontinuity in the skin tissue that change the index of refraction in these spots where the beam interacted with the tissue. As a consequence, tissue scattering and absorption properties are changed so that incoming electromagnetic (EM) radiation absorption is enhanced or back scattering is enhanced so that smaller amount of the incoming radiation is able to penetrate beyond the tissue modified zones compared to untreated skin tissue. This reduction in the transmission of incoming EM radiation and light will thus enhance the protection from damage that can cause cancer or aging of the skin.

A preferred embodiment contemplates using a discrete spots to create a zone of modified tissue. Tissue modification can also be accomplished by utilizing a wide beam to modify a large volume of tissue. For multi-photons interaction, a high volumetric power density is required which often requires a focused and narrow beam. Such narrow beam or an ensemble of beams can create discrete spots of tissue modifications that can be created adjacent to each other to create a continuous volume change. In a preferred embodiment narrow beam or an ensemble of beams can create discrete spots of tissue modifications that can be created apart from each other to create a non-continuous volume change. Such a discrete pattern of volumetric micro-zones can be made according to the description in exhibit A herein. A preferred embodiment also contemplates leaving about 5 µm of unmodified tissue between the surface of the skin and the beginning of the volume of modified micro-zones created by the device. More preferably 10 µm of unmodified tissue is left between the surface of the skin and the beginning of the volume of modified micro-zones created by the device. More preferably yet 20 µm of unmodified tissue is left between the surface of the skin and the beginning of the volume of modified micro-zones created by the device. Most preferably 30, 40, 50 or 60 µm of unmodified tissue is left between the surface of the skin and the beginning of the volume of modified micro-zones created by the device. One unique aspect of the device and method described herein, allow it, in a preferred embodiment, to create all these volumetric modifications while leaving a volumetric zone between the surface of the skin and the upper boundary of the modified volumetric zone unmodified, is creating these effect without the use of external cooling of the surface. Thus, no cryogen spray, contact cooling, TEC, Peltier cooler, or water cooling, among other cooling methods known in the art need be applied to the surface.

Energy can be applied to the skin while placing a transparent element in contact with the skin and in the path of the beam of energy, preferably ultrashort pulse beam of a train of pulses as described herein. The transparent element can be, for example, a focusing element, or a set of lenses, that allows the beam to be focused at the volumetric zone underneath the surface to create the desired ensemble of micro-zones as described above. The transparent element may also be cooled, although as described above, cooling is often not needed. Alternatively and preferably, a guiding element such as an optical fiber, a hollow wave guide, a micro-needle or micropipette among other element capable of guiding the energy and in particular the electromagnetic energy or light, can be used. Such guiding element, for example, hollow wave guide, may preferably bring the energy to the skin or also preferably even below the skin.

The device contemplated above for treating a region of intact living skin having a surface and an epidermis, dermis and an adipose layer, can be used in a method of treating a skin condition, comprising operating the device such that the pattern of substantially discrete spots of modified tissue result in increased reflection of incident electromagnetic energy including sunlight and UV radiation.

This method for treating a skin condition also preferably comprises operating the device described above such that said pattern of substantially discrete spots of modified tissue result in changes to the apparent color of the skin.

Additionally and preferably, the method of treating a skin condition, comprising operating the device described above such that surface of the skin is substantially not modified and any tissue below or above the zone of modified tissue including the pattern of modified spots and removed from it by about 5 µm or more remained unaffected by the operation of the device.

Additionally and preferably, the method of treating a skin condition, comprising operating the device described above such that surface of the skin is substantially not modified and any tissue below or above the modified zone including the pattern of modified spots and removed from it by about 10, 20, 30, 40, 50, 60 or even 70 µm or more remained unaffected by the operation of the device.

Additionally, the method described above comprises operating the device described above and further treating the skin with anti-microbial radiation that includes blue to ultraviolet wavelengths.

Additionally, the method described above comprises operating the device described above and applying a vacuum to the skin within 5 minutes of application of the pulse.

Devices for treating a region of intact living skin can include a sharp object, for example a micro-needle, extending from a hand-held base; and a member that prevents the micro-needle from penetrating the skin to a depth greater than the epidermal-dermal junction. The length of the tip of the micro-needles can be less than about 1 mm. The penetrating depth can be shorter than 0.5 mm, and more preferably shorter than 0.25 mm, more preferably yet shorter than about 0.1 mm, more preferably yet shorter than about 0.075 mm, more preferably than shorter than about 0.05 mm and most preferably shorter than about 0.025 mm. The distance between adjacent sharp object tips is preferably less than about 5 mm. More preferably the distance between the tips of adjacent sharp object tips is less than about 2 mm and more preferably yet less than about 1 mm. Generally a preferred embodiment can have distances between adjacent tips as described for the distances between adjacent spots in exhibit A.

The sharp objects described above can be hollow, and can be connected to a compressed gas source said compressed gas source is capable of injecting gas to the region surrounding the tips of the inserted sharp objects. In such cases the compressed air source is preferably capable of injecting the compressed air to a region surrounding the tips of the inserted sharp objects. Alternatively, the compressed air or gas source is replaced by a liquid source such as a liquid reservoir, for example a reservoir of dye or ink or pigmented liquids, such that the liquid can be inserted to the skin region surrounding the inserted tip. The injected fluid (gas or liquid phases) can remain substantially within any one or more of the epidermal tissue, dermal tissue, or adipose 1. In FIG. 8*a*, for example, member 467 substantially prevents the micro-needle from penetrating the tissue below the adipose layer of the skin.

In yet other contemplated embodiments, the sharp objects described above comprise at least two micro-channels, for example, hollow channels, capable of delivering electromagnetic energy to the tip of said micro-needle. Preferably, one of the micro-channels can also deliver a fluid capable of absorbing or reflecting a nontrivial amount of the electromagnetic energy delivered to the tip by the sharp objects.

Thus, several embodiments and applications of device and method for the creation of subsurface layered disruption patterns using multiple photo disrupted tissue modified micro-zones have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Excising Skin Tissue

In a preferred embodiment a method and a device for the creation of fresh surface with minimal or no thermal damage is also contemplated. As shown in FIG. 2A an energy source 200 capable of generating pulses of electromagnetic energy with wavelength between 100 micrometer and 100 nm and preferably between 2 micrometer and 200 nm and most preferably between 1.6 micrometer and 330 nanometer is sent directly to a beam modifier 196 or to an amplifier 210. Each pulse arriving at the beam modifier 196 has energy of between 0.01 nj and 100 Joule and preferably between 1 nj and 10 Joules and most preferably between 10 nJ and about 500 mJ.

The pulse coming out of the amplifier 210 may have a repletion rate of 0.01 Hz to 50 MHz and preferably between 1 Hz and about 1 MHz, and most preferably between about 1 Hz and about 100 KHz. The pulse train out of the oscillator 200 has a pulse repetition rate of between about 100 KHz and about 200 MHz and preferably between 10 MHz and 100 MHz.

The beam 133 or 215 are either stirred by a mirror-scanner 103 in the beam modifier 196 or by beam modifying elements such as diffractive optics a multiple lens arrays or Kinoform phase plates within the beam modifiers 196 to create a multiple beam arrays 223 of at least 9 beams, capable of creating a pattern of focused beam spots at the surface 143. The focused beam spots should have sufficient energy density to ablate at least some of the material form the surface of the target. Subsequent beam pulses remove additional material preferably in a way that leave little or no thermal or mechanical damage on the remaining material, preferably, such thermal or mechanical should be confined to material extending to less than about 50 micrometer from the ablated surface and more preferably to less than about 7 micrometer and most preferably to less than about 2 micrometer.

In further preferred embodiment the method contemplated herein also consist removing the surface layer of the targeted surface by a multiple beam as described above and shown in FIG. 2A. The exposed surface is then photographed or otherwise imaged with a CCD camera or optical coherent tomography or fluoresce imaging, or nonlinear/third harmonic generation (THG) imaging, multiphoton imaging, Birefringent imaging, Fluorescence lifetime imaging, infrared thermography, or other method of imaging or other appropriate imaging system 134 as shown in FIG. 2A. The imaging is designed to look at signs of cancer, malignant cells, excess pigmentation, vascular target, or other skin cells abnormality. For example, in a preferred embodiment, a baseline image or an image of adjacent normal skin surface can be obtained and stored in the system data base. The obtained image is then compared to the desired surface characteristics (for example, a surface image free of signature marker of malignant cells (for example, Florence signature of malignancy). An automated microprocessor 202, in a preferred embodiment, then determine if the desired image was obtained. If such an image has not achieved, another layer of the skin surface is removed, by the beams 223. Alternatively and preferably, the use of the system can control and inspect the image manually. For example, the image from the monitoring element 134 may appear on a screen 204. The operator 206 (for example, a physician) can then examine the image activate an on/off switch 207 to continue removing several layers of skin with the beams 223 or stop the treatment process. The process can be repeated iteratively until the operator decide that sufficient volume of tissue has been removed so that the image he receives no longer show the undesired parameter, for example, fluorescence from cancer cells within the surface of the skin. At that point the operator can decide to stop the process and does not remove additional layers of tissue. Alternatively and preferably, the ablation and removal of surface tissue layers can be controlled by the microprocessor 202 so the process is automated as described above.

The method and the device shown in FIG. 2A, can thus be used to ablated and image a 3-dimensional target tissue, ablating the surface, imaging the exposed surface, removing additional layers. For example, a multi-photon laser scanning microscope can be used for the imaging process. As described above, in a preferred embodiment, the oscillator 200 generate ultra-short laser pulses shorter than about 10 ps and the amplifier 210 increase the energy of these pulses. Thus, a preferred embodiment include ablating or removing skin surface with pulses form the amplifier 210 with pulse energy of about 100 nJ or more and more preferably with pulses of 1 microjoule or more, and subsequently use un-amplified pulses from the oscillator with pulse energy of about 1 microjoule or less and more preferably pulses of 100 nJ or less. If the images indicated that more tissue needs to be removed then the pulses from the amplifier with additional energy can be used. In a preferred embodiment, prior to imaging, the skin is stained to allow better imaging. In yet another preferred embodiment, the stain includes a fluorescent material applied to the exposed skin surface. In yet another preferred embodiment, fluorescent labeled antibodies are applied to the surface ablated by the laser or an immuno-reactive antibody can be applied to the ablated by the laser. In further preferred embodiment the amplifier 210, is an optical amplifier, said optical amplifier can be, for example, a regenerative optical amplifier, multipass optical amplifier, fiber amplifier, a semiconductor optical amplifier, optical parametric amplifier (OPA), or other type of amplifier.

In yet another preferred embodiment, the ablation or surface layers removal step consist of removing at least 2 micrometer of the skin surface tissue. More preferably, at least about 5 micrometers of the skin surface is removed during each removal step. More preferably yet, at least 10 micrometer of skin surface tissue is removed. More preferably yet a layer of at least 15 micrometer is removed. In a most preferred embodiment a layer of at least 20 micrometer is removed.

In a further preferred embodiment, the device contemplated is used for biopsy and imaging of three dimensional section of the skin, the device comprises as shown in FIG. 2A, a source of energy 200 capable of producing a short light pulses, preferably shorter than about 1 ns, said device further comprises a multiple beams pattern of at least three beams, 223, the device further comprises, means to generate an image of the skin surface, before during and after ablating the surface with said energy source 200 and beam 223. Preferably the device further comprises an imaging element 134, for example, a CCD camera, a photomultiplier, an Optical Coherent Tomography, a microscope, and ultrasound detector, a photo-acoustic imaging element, or other elements capable of imaging the ablated and exposed surface, said imaging element 134, is capable of sending the detected signals to a microprocessor 202 operatively coupled to the energy generator (for example, an ultrashort pulse laser) 200, to automatically process the image and decide if sufficient depth or sufficient amount of skin tissue was removed. Preferably, the device can also comprise a monitor 204 which shows the image and data collected by the detector or imaging element 134, wherein an operator 206 can view the data and image from the freshly exposed skin tissue and decide if another layer of skin tissue has to be exposed or if the operation can be terminated. The device may further comprise a computer microprocessor 202 that can automatic repeat the skin tissue layer removal process and the process of generating images of subsequently exposed skin surfaces until a desired volume of the skin 143 has been removed (for example, all the malignant or benign but abnormal skin tissue) or until a sufficient amount of tissue has been imaged.

In a preferred embodiment, the device further comprises an acquisition and storage component 202, for example a computer with acquisition, processing and storage capacity. The device may further comprise the skin tissue endogenous signals for imaging.

In a preferred embodiment the device further utilize optical nonlinearities such harmonic generation, (second or third harmonic generation), Raman spectroscopy, multi-photon absorption fluorescence and multiphoton spectroscopy, or nonofficial microscopy to generate image contrast or image of the exposed surface. In further preferred embodiment, said multiple images are combined to generate three dimensional image of the volume of the skin. In further preferred embodiment, said images are viewed consecutively by the operator who then decide whether sufficient amount of tissue was removed or whether all the malignant tissue was removed. Preferably, in another preferred embodiment, the operator relies on automated processor 202 to decide where a targeted tissue volume or a segment of a tissue with specific physical characteristics that can be distinguished by the detector 134 and the processor, 202, has been removed so that the operation of the device can be stopped.

Skin Tumor Removal/Moh Surgery

In a preferred embodiment the iterative removal and imaging process described above is replaced with iterative skin tissue removal and diagnostics and analysis of tissue in procedures such as Mohs Surgery.

Here a microscopically controlled surgery is performed. Such a surgical procedure is highly effective for common types of skin cancer, with a cure rate of up to 99% for basal cell carcinoma, the most common type of skin cancer, and for squamous cell carcinoma. Because the Mohs procedure is micrographically controlled, it provides precise removal of the cancerous tissue, while healthy tissue is spared. For this reason, Mohs surgery results in a significantly smaller surgical defect and an improved cosmetic result compared to other methods of skin cancer treatment.

The Mohs procedure is recommended for skin cancer removal in anatomic areas where maximum preservation of healthy tissue is desired for cosmetic and functional purposes (the face, eyelids, nose, ear, fingers, genital area), for cancers with indistinct margins, and for recurrent cancers in scar tissue. It is especially indicated for lesions that have recurred following prior treatment, or for lesions in anatomic areas that have the greatest likelihood of recurrence (for example the side of the nose). Mohs surgery is relatively expensive when compared to other surgical modalities alone, but has been shown to be less expensive compared with other modalities for aggressive tumors or tumors in high risk locations due to the inherent high risk of recurrence in these tumors and potential future associated costs. For this reason, it is used generally for recurrent tumors, indistinct tumors, or tumors in areas such as the face, where sparing normal tissue around the skin cancer is paramount.

In a preferred embodiment, the device of FIG. 2A is used to remove skin tumor (malignant or benign) for example, such as those done in Mohs surgery, and is preferably performed with the following steps: Surgical removal of tissue (Surgical Oncology) with the device of FIG. 2A; Mapping the piece of tissue, freezing and cutting the tissue between 5 and 10 micrometers using a cryostat, and staining with H&E or other stains (including T. Blue); Interpretation of microscope slides (Pathology); Reconstruction of the surgical defect (Reconstructive Surgery).

The device of FIG. 2A is used to surgically remove skin tissue from the suspected skin region. After each surgical removal of tissue, the specimen is processed (look here for a clay animation of tissue processing), cut on the cryostat and placed on a slides, stained with H&E and then read by the operator or the surgeon who examines the sections for cancerous cells. If cancer is found, its location is marked on the map (drawing of the tissue) and the surgeon removes the indicated cancerous tissue from the patient. This procedure is repeated until no further cancer is found.

Photodisruption Barriers/Modification of Subsurface Physical Characteristics.

Additional preferred embodiment utilize the device for creating the disruption below the surface described above to generate as many physical disruption in the path of an external influence (in particular blockage of harmful sunlight rays) in the epidermis above many of the skin melanin-containing cells. For example, in a preferred embodiment such pattern of photodisruption is generated below the surface of the skin and down to a depth of 100 um. If we assume disruptions diameter of 1 to 3 micrometer. For example, we consider disruptions of a diameter of about 1.5 micrometer in diameter and a 1.5 micrometer of unmodified tissue between said photodisruption for a total of 3 micrometer. This means that about 33 layers of photo-disruption spots can be created down to a depth of about 100 micrometer. If for simplicity we assume 20 such layers of photo disruptions generate in the epidermis 181 shown in FIG. 2A, then in a 1 cm² area we can, for example, generate two "disruption cell" in 10 um (e.g. disrupted+untouched for example of 5 micrometer "disruption cell" size). This means that 2000 disruptions can be generated in a linear pattern one cm long and in an area of 1 cm² we have 4 million disruptions, and in a volume of 100 um by 1 cm square, we have about 80 million such disruptions. Since an optical oscillator that can generate a picosecond or femtosecond light pulses, often operates at pulse repletion rate of from about 70 MHz to 90 MHz, for example, 88 MHz, such 80 million subsurface disruption can be generated in less than one second. If for example a surface of the skin of area of 100 cm² needs to be covered, for example a surface of the facial area, than such ultrashort pulse laser, or a picosecond laser, or a microchip laser, can generate such a photo-disruptions pattern in about 100 seconds or about a minute and half which is a reasonable operating time for a treatment.

In another preferred embodiment shown in FIG. 2A, a device and a method for creating the disruption below the surface is described. The method include the step of using the device described in FIG. 2A to create a photo-disruption at least five micrometer below the surface of the skin and at least five micrometer above the epidermal dermal junction. In a preferred embodiment, such disruptions leave at least the upper five micrometer of the surface of the skin unchanged and at least five micrometer of above the epidermal dermal junction unchanged while reducing optical transmission through said modified region by at least 3%.

Further preferred embodiment contemplate creating such a zone of photodisruption below the surface of the skin while leaving layer at least 10 micrometer below the surface physically unchanged and at least 10 micrometer above the epidermal-dermal junction physically unchanged while reducing optical transmission through said modified region by at least 3%.

Additional preferred embodiment contemplate creating such a zone of photodisruption below the surface of the skin while leaving layer at least 20 micrometer below the surface physically unchanged and at least 20 micrometer above the epidermal-dermal junction physically unchanged while reducing optical transmission through said modified region by at least 3%. Additional preferred embodiment contemplated leaving said layers with 30 micrometer, and 40 micrometer in thickness. Even more preferred embodiments reduce optical transmission through said zone of photodisruption by 5%, 10%, 15%, 20%, 30%, 35%, 40%, 50%, 60%, 70%, 80%, 90% and most preferably, by 95% or more.

Another preferred embodiment contemplate the device and method shown in FIG. 2A and discussed above, for creating the zone of photodisruption spots below the skin surface as described above but instead of reducing the optical transmission through said modified region, a physical characteristic selected from the group of: Thermal conductivity, Heat capacity, Porosity, Electrical conductivity, Elasticity, The ability to allow fluid to flow across the skin from the surface to the dermis; The ability to allow liquid to flow across the skin from the surface to the dermis; The ability to allow a substance to flow across the skin from the surface to the dermis; Other physical properties of the skin is changed according to the same change parameters as described above for the reduction in optical transmission.

Another preferred embodiment create the above changes in deeper layers of the skin, for example, said zone of photodisruptions is created between the epidermal-dermal junction and above the adipose layer, or in the upper dermis, in the mid reticular dermis, in the lower reticular dermis, or in a series of multiple layers in between the surface of the skin and the muscle layer below the adipose layer.

What is claimed is:

1. A device for treatment of soft tissue, comprising
an electromagnetic energy beam generator that produces at least one beam of electromagnetic energy, wherein the at least one beam comprises pulses with pulse durations from 10 femtoseconds to 10 nanoseconds, wherein said pulses have pulse rep rates between 10 MHz and 100 MHz, and each pulse has at least 0.1 nanojoule of energy;
an optic assembly configured to redirect the source beam in space; and
a mechanism that displaces the optic assembly by increments of less than 500 µm in a z direction.

2. The device of claim 1, further comprising an imaging element configured to evaluate the target region before, during, and after interaction with the beam.

3. The device of claim 2, wherein said imaging element comprises one or more of the following: a camera; an optical coherent tomography (OCT); a microscope; a spectrometer; an ultrasound imaging member; or a wavefront analyzer.

4. The device of claim 1, wherein the optic assembly comprises a diffractive element that redirects the beam to at least 100 distinct locations within targeted tissue.

5. The device of claim 4, wherein the optic assembly redirects the beam to at least 1000 distinct locations within targeted tissue.

6. The device of claim 1, wherein the optic assembly comprises at least one of the following elements:
a lens;
a mirror;
a concave mirror;
a convex mirror;
an AOM;
an EOM; or
a diffractive element.

7. The device of claim 1, wherein the beam generator has a pulse repetition rate of at least $10^3$ per second.

8. The device of claim 1, wherein the optic assembly produces at least $10^4$ beams in an x,y plane.

9. The device of claim 1, wherein the mechanism that displaces the optic assembly comprises a piezoelectric transducer.

10. The device of claim 1, further comprising a controller configured to control movement of the optic assembly and redirection of the beam.

11. The device of claim 10, wherein the controller is programmed to redirect the beam to create a series of subsurface cavities in the targeted tissue.

12. The device of claim 10, wherein the targeted tissue is a human cornea, and wherein the controller is programmed to redirect the beam to cut a flap in the targeted tissue.

13. The device of claim 10, wherein the controller is programmed to redirect the beam to create cuts in the targeted tissue.

14. A device for treatment of tissue, comprising:
an electromagnetic energy beam generator that produces at least one source beam of electromagnetic energy, wherein the source beam comprises pulses with pulse durations from 10 femtoseconds to 10 nanoseconds;
an optic configured to redirect the source beam in space and to focus the source beam to a spot size having a diameter of 25 micrometers or more;
a mechanism that displaces the optic by increments of less than 500 µm in a z direction; and a controller configured to control movement of the optic to redirect the source beam, the controller programmed to redirect the source beam between pulses to create complex subsurface patterns in targeted tissue;

wherein the beam has sufficient energy to create a disruption in the continuity of the targeted tissue, but the energy of the beam is insufficient to cause tissue damage extending more than 5 micrometer beyond the tissue disruption.

15. The device of claim 14, further comprising an imaging element configured to evaluate the target region before, during, and after interaction with the beam.

16. The device of claim 15, wherein said imaging element comprises one or more of the following: a camera; an optical coherent tomography (OCT); a microscope; a spectrometer; an ultrasound imaging member; or a wavefront analyzer.

17. The device of claim 14, wherein the controller is programmed to redirect the beam to create a series of subsurface cavities in the targeted tissue.

18. The device of claim 14, wherein the targeted tissue is a human cornea, and wherein the controller is programmed to redirect the beam to cut a flap in the targeted tissue.

19. The device of claim 14, wherein the beam has sufficient energy to modify the targeted tissue by mechanical changes to the tissue.

20. The device of claim 14, wherein the beam has sufficient energy and pulse repetition rate to achieve three-dimensional heating in the targeted tissue due to accumulation of heat from a pulse train as well as through multiphoton absorption of each pulse.

21. A device for treatment of tissue, comprising:

an electromagnetic energy beam generator that produces at least one source beam of electromagnetic energy, wherein the source beam comprises pulses with pulse durations from 10 femtoseconds to 10 nanoseconds, wherein the electromagnetic energy beam generator emits the pulses at pulse repetition rates from 0.001 Hz to about 1 MHz, and the pulse energy is from 0.01 microjoule to 10 joule;

an optic configured to redirect the source beam in space and to focus the source beam to a spot size having a diameter of 25 micrometers or more; and a controller configured to control movement of the optic to redirect the source beam, the controller programmed to redirect the source beam between pulses to create complex subsurface patterns in targeted tissue while preventing the coalescence of more than 100 subsurface disruptions into a structural discontinuity;

wherein the beam has sufficient energy to create at least one disruption in the continuity of the targeted tissue.

22. The device of claim 21, wherein the controller is configured to control movement of the optic to redirect the source beam to prevent the coalescence of more than 10 subsurface disruptions into a structural discontinuity.

23. The device of claim 21, wherein the electromagnetic energy beam generator emits the pulses at pulse repetition rates from 1 Hz to 100 kHz.

24. The device of claim 21, wherein the controller is configured to control movement of the optic to redirect the source beam to create subsurface disruptions in targeted tissue at depths from 10 micrometer to 2 cm from a tissue surface.

25. The device of claim 24, wherein the controller is configured to control movement of the optic to redirect the source beam to create subsurface disruptions in targeted tissue at a depth of 1.5 cm from the tissue surface.

26. The device of claim 21, wherein the optic is configured to redirect the source beam in space and to focus the source beam to a spot size having a diameter of 50 micrometers or more.

27. The device of claim 21, wherein the pulse energy is 50 microjoule and above.

* * * * *